US007135556B2

(12) United States Patent
Altmann et al.

(10) Patent No.: US 7,135,556 B2
(45) Date of Patent: Nov. 14, 2006

(54) NPC1L1 (NPC3) AND METHODS OF USE THEREOF

(75) Inventors: Scott W. Altmann, Fanwood, NJ (US); Nicholas J. Murgolo, Millington, NJ (US); Luquan Wang, East Brunswick, NJ (US); Michael P. Graziano, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 292 days.

(21) Appl. No.: 10/736,769

(22) Filed: Dec. 16, 2003

(65) Prior Publication Data

US 2004/0161838 A1     Aug. 19, 2004

Related U.S. Application Data

(63) Continuation-in-part of application No. 10/663,208, filed on Sep. 16, 2003, which is a continuation-in-part of application No. 10/646,301, filed on Aug. 22, 2003, which is a continuation-in-part of application No. 10/621,758, filed on Jul. 17, 2003.

(60) Provisional application No. 60/397,442, filed on Jul. 19, 2002.

(51) Int. Cl.
| A61K 38/47 | (2006.01) |
| C07K 16/24 | (2006.01) |
| C07K 16/26 | (2006.01) |
| G01N 33/58 | (2006.01) |
| G01N 33/531 | (2006.01) |

(52) U.S. Cl. .................. 530/395; 530/350; 530/391.3; 435/449; 424/192.1

(58) Field of Classification Search ................ 530/395, 530/350, 391.3; 435/449; 424/192.1
See application file for complete search history.

(56) References Cited

U.S. PATENT DOCUMENTS

| 5,306,817 A | 4/1994 | Thiruvengadam et al. .. 540/200 |
| 5,561,227 A | 10/1996 | Thiruvengadam et al. .. 540/200 |
| 5,618,707 A | 4/1997 | Homann et al. ............ 435/146 |
| 5,624,920 A | 4/1997 | McKittrick et al. ......... 514/210 |
| 5,627,176 A | 5/1997 | Kirkup et al. ............... 514/210 |
| 5,631,365 A | 5/1997 | Rosenblum et al. ........ 540/200 |
| 5,633,246 A | 5/1997 | McKittrick et al. ......... 514/210 |
| 5,656,624 A | 8/1997 | Vaccaro et al. ............. 540/210 |
| 5,661,145 A | 8/1997 | Davis ......................... 514/210 |
| 5,688,785 A | 11/1997 | Vaccaro ..................... 514/210 |
| 5,688,787 A | 11/1997 | Burnett et al. .............. 514/210 |
| 5,688,990 A | 11/1997 | Shankar ....................... 560/39 |
| 5,698,548 A | 12/1997 | Dugar et al. ................ 514/210 |
| 5,728,827 A | 3/1998 | Thiruvengadam et al. .. 540/200 |
| 5,739,321 A | 4/1998 | Wu et al. .................... 540/200 |
| 5,744,467 A | 4/1998 | McKittrick et al. ......... 514/210 |
| 5,756,470 A | 5/1998 | Yumibe et al. ................ 514/25 |
| 5,767,115 A | 6/1998 | Rosenblum et al. ........ 514/210 |
| 5,846,966 A | 12/1998 | Rosenblum et al. ........ 514/210 |
| 5,856,473 A | 1/1999 | Shankar ...................... 540/200 |
| 5,886,171 A | 3/1999 | Wu et al. .................... 540/200 |
| 5,919,672 A | 7/1999 | Homann et al. ............ 435/121 |
| 6,093,812 A | 7/2000 | Thiruvengadam et al. .. 540/200 |
| 6,096,883 A | 8/2000 | Wu et al. .................... 540/200 |
| 6,133,001 A | 10/2000 | Homann et al. ............ 435/121 |
| 6,207,822 B1 | 3/2001 | Thiruvengadam et al. .. 540/200 |
| RE37,721 E | 5/2002 | Rosenblum et al. ........ 514/210 |
| 6,426,198 B1 | 7/2002 | Cartsea et al. |
| 6,593,078 B1 | 7/2003 | Altmann et al. ................ 435/4 |
| 6,627,757 B1 | 9/2003 | Fu et al. ................... 546/272.4 |
| 6,632,933 B1 | 10/2003 | Altmann et al. ........... 536/17.4 |
| 2002/0151536 A1 | 10/2002 | Davies et al. |
| 2004/0093629 A1 | 5/2004 | Altmann et al. |
| 2004/0132058 A1 | 7/2004 | Altmann et al. |
| 2004/0137467 A1 | 7/2004 | Altmann et al. |

FOREIGN PATENT DOCUMENTS

| WO | WO 00/20623 | 4/2000 |
| WO | WO 00/34240 | 6/2000 |
| WO | WO 00/60107 | 10/2000 |
| WO | WO 00/63703 | 10/2000 |
| WO | WO 01/57190 | 8/2001 |
| WO | WO 01/70974 | 9/2001 |
| WO | WO 01/75067 | 10/2001 |
| WO | WO 02/079174 | 10/2002 |
| WO | WO 03/100094 | 12/2003 |
| WO | WO2004/014947 A1 | 2/2004 |
| WO | WO 2004/32716 A2 | 4/2004 |
| WO | WO2005/69900 | 8/2005 |
| WO | WO2006015365(A1) | 2/2006 |

OTHER PUBLICATIONS

Blom et al. (2003) Defective endocytic trafficking of NPC1 and NPC2 underlying infantile Niemann-Pick type C disease. Hum. Mol. Genet., vol. 12, No. 3, pp. 257-272.*

Erickson et al., "Studies on neuronal death in the mouse model of Niemann-Pick C disease." J. Neurosci. Res. Jun. 15, 2002;68(6):738-44.

Erickson et al., "mdr1a deficiency corrects sterility in Niemann-Pick C1 protein deficient female mice." Mol. Reprod. Dev. Jun. 2002;62(2):167-73.

Altmann et al., "Niemann-Pick C1 Like 1 protein is critical for intestinal cholesterol absorption." Science. Feb. 20, 2004;303(5661):1201-4.

(Continued)

*Primary Examiner*—Karen Cochrane Carlson
*Assistant Examiner*—Samuel Wei Liu

(57) ABSTRACT

We claim an isolated polypeptide having ability of binding with cholesterol. Said polypeptide is useful for investigating regulation of intestinal cholesterol absorption and cholesterol levels. Also, we claim a composition comprising said polypeptide bound to cholesterol or ezetimibe and a fusion protein comprising the polypeptide thereof.

13 Claims, No Drawings

OTHER PUBLICATIONS

Erickson et al., "Pharmacological and genetic modifications of somatic cholesterol do not substantially alter the course of CNS disease in Niemann-Pick C mice." J. Inherit. Metab. Dis. Feb. 2000;23(1):54-62.

International Search Report for International Application No. PCT/US03/40113.

International Search Report for International Application No. PCT/US03/22467.

MGI web page "gene detail" of the NPC1L1 gene.

Altmann et al., "Niemann-Pick C1 Like 1 protein is critical for intestinal cholesterol absorption." Science. Feb. 20, 2004;303(5661):1201-4.

Davies et al., Inactivation of NPC1L1 causes multiple lipid transport defects and protects against diet-induced hypercholesterolemia. J. Biol. Chem. Apr. 1, 2005;280(13):12710-20.

Minhas, Current Progress in Lipid Therapy Br. J. Cardiology 10(1): 59-68 (2003).

Abstracts 1-79 from "The International Conference on Niemann-Pick Type C Disease"; May 29-31, 2003; Tuscon, Arizona.

Carstea et al., Niemann-Pick C1 disease gene: homology to mediators of cholesterol homeostasis Science 277:228-231 (1997).

Polypeptide Sequence ABG22693 disclosed in WO 01/75067.

Genbank Sequence Disclosure; Accession No. AF192522.

Genbank Sequence Disclosure; Accession No. AF002020.

Davies et al., Evidence for a Niemann-pick C (NPC) gene family: identification and characterization of NPC1L1 Genomics 65(2): 137-145 (2000).

Ioannou et al., "The structure and function of the Niemann-Pick C1 protein." Mol. Genet. Metab. 71(1-2): 175-181 (2000).

Genbank Sequence Disclosure, Accession No. AK078947.

Altmann et al., "The identification of intestinal scavenger receptor class B, type I (SR-BI) by expression cloning and its role in cholesterol absorption." Biochim. Biophys. ACTA 1580: 77-93 (2002).

DeNinno et al., "Steroidal glycoside cholesterol absorption inhibitors" J. Med. Chem. 40(16):2547-2554 (1997).

Kramer, et al., "Characterization and identification of the intestinal cholesterol uptake system" Falk Symposium 129, Bile Acids: From Genomics to Disease and Therapy, 147-160 (2003).

Amigo et al., "Relevance of Niemann-Pick Type C1 Protein Expression in Controlling Plasma Cholesterol and Biliary Lipid Secretion in Mice" Hepatology 36(4): 819-828 (2002).

Repa, et al., "Inhibition of cholesterol absorption by SCH 58053 in the mouse is not mediated via changes in the expression of mRNA for ABCA1, ABCG5, or ABCG8 in the enterocyte". Journal of Lipid Research 43:1864-1874 (2002).

Hauser et al., "Identification of a Receptor Mediating Absorption of Dietary Cholesterol in the Intestine" Biochemistry 37(51): 17843-17850 (1998).

Acton et al., "Expression Cloning of SR-BI, a CD36-related Class B Scavenger Receptor" The Journal of Biological Chemistry 269(33): 21003-21009 (1994).

Hernandez et al., "Intestinal absorption of cholesterol is mediated by a saturable, inhibitable transporter" Biochimica et Biophysica Acta 1486: 232-242 (2000).

Detmers et al., "A target for cholesterol absorption inhibitors in the enterocyte brush border membrane" Biochimica et Biophysica Acta 1486: 243-252 (2000).

Smart et al., "Annexin 2-caveolin 1 complex is a target of ezetimibe and regulates intestinal cholesterol transport" Proc. Natl. Acad. Sci. 101(10):3450-3455 (2004).

Dawson et al., "Intestinal cholesterol absorption" Curr Opin Lipidol. 10(4):315-320 (1999).

Allayee et al., "Biochemistry. An absorbing study of cholesterol" Biochemistry. An absorbing study of cholesterol. Science. 290(5497):1709-1711 (2000).

Berge et al., "Accumulation of dietary cholesterol in sitosterolemia caused by mutations in adjacent ABC transporters" Science 290(5497):1771-1775 (2000).

Jourdheuil-Rahmani et al., "Biliary anionic peptide fraction and apoA-I regulate intestinal cholesterol uptake" Biochem Biophys Res Commun 292(2):390-5 (2002).

Werder et al., "Role of scavenger receptors SR-BI and CD36 in selective sterol uptake in the small intestine" Biochemistry 40(38):11643-50 (2001).

Zetia™ Prescribing Information Sheet.

Ioannou, Multidrug permeases and subcellular cholesterol transport, Nat Rev Mol Cell Biol. Sep. 2001;2(9):657-68.

* cited by examiner

NPC1L1 (NPC3) AND METHODS OF USE THEREOF

This application is a continuation-in-part of U.S. patent application Ser. No. 10/663,208; filed Sep. 16, 2003 which is a continuation-in-part of U.S. patent application Ser. No. 10/646,301; filed Aug. 22, 2003 which is a continuation-in-part of U.S. patent application Ser. No. 10/621,758; filed Jul. 17, 2003 which claims the benefit of U.S. Provisional Patent Application No. 60/397,442; filed Jul. 19, 2002 each of which is herein incorporated by reference in its entirety.

FIELD OF THE INVENTION

The present invention includes NPC1L1 polypeptides and polynucleotides which encode the polypeptides along with methods of use thereof.

BACKGROUND OF THE INVENTION

A factor leading to development of vascular disease, a leading cause of death in industrialized nations, is elevated serum cholesterol. It is estimated that 19% of Americans between the ages of 20 and 74 years of age have high serum cholesterol. The most prevalent form of vascular disease is arteriosclerosis, a condition associated with the thickening and hardening of the arterial wall. Arteriosclerosis of the large vessels is referred to as atherosclerosis. Atherosclerosis is the predominant underlying factor in vascular disorders such as coronary artery disease, aortic aneurysm, arterial disease of the lower extremities and cerebrovascular disease.

Cholesteryl esters are a major component of atherosclerotic lesions and the major storage form of cholesterol in arterial wall cells. Formation of cholesteryl esters is also a step in the intestinal absorption of dietary cholesterol. Thus, inhibition of cholesteryl ester formation and reduction of serum cholesterol can inhibit the progression of atherosclerotic lesion formation, decrease the accumulation of cholesteryl esters in the arterial wall, and block the intestinal absorption of dietary cholesterol.

The regulation of whole-body cholesterol homeostasis in mammals and animals involves the regulation of intestinal cholesterol absorption, cellular cholesterol trafficking, dietary cholesterol and modulation of cholesterol biosynthesis, bile acid biosynthesis, steroid biosynthesis and the catabolism of the cholesterol-containing plasma lipoproteins. Regulation of intestinal cholesterol absorption has proven to be an effective means by which to regulate serum cholesterol levels. For example, a cholesterol absorption inhibitor, ezetimibe

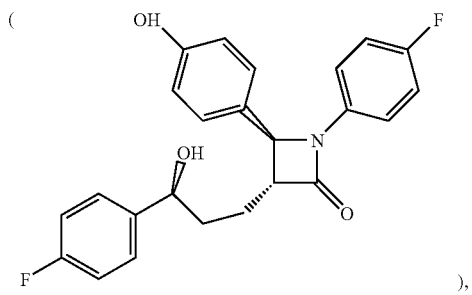

has been shown to be effective in this regard. A pharmaceutical composition containing ezetimibe is commercially available from Merck/Schering-Plough Pharmaceuticals, Inc. under the tradename Zetia®. Identification of a gene target through which ezetimibe acts is important to understanding the process of cholesterol absorption and to the development of other, novel absorption inhibitors. The present invention addresses this need by providing a rat and a mouse homologue of human NPC1L1 (also known as NPC3; Genbank Accession No. AF192522; Davies, et al., (2000) Genomics 65(2):137–45 and Ioannou, (2000) Mol. Genet. Metab. 71(1–2):175–81), an ezetimibe target.

NPC1L1 is an N-glycosylated protein comprising a YQRL (SEQ ID NO: 38) motif (i.e., a trans-golgi network to plasma membrane transport signal; see Bos, et al., (1993) EMBO J. 12:2219–2228; Humphrey, et al., (1993) J. Cell. Biol. 120:1123–1135; Ponnambalam, et al., (1994) J. Cell. Biol. 125:253–268 and Rothman, et al., (1996) Science 272:227–234) which exhibits limited tissue distribution and gastrointestinal abundance. Also, the human NPC1L1 promoter includes a Sterol Regulated Element Binding Protein 1 (SREBP1) binding consensus sequence (Athanikar, et al., (1998) Proc. Natl. Acad. Sci. USA 95:4935–4940; Ericsson, et al., (1996) Proc. Natl. Acad. Sci. USA 93:945–950; Metherall, et al., (1989) J. Biol. Chem. 264:15634–15641; Smith, et al., (1990) J. Biol. Chem. 265:2306–2310; Bennett, et al., (1999) J. Biol. Chem. 274:13025–13032 and Brown, et al., (1997) Cell 89:331–340). NPC1L1 has 42% amino acid sequence homology to human NPC1 (Genbank Accession No. AF002020), a receptor responsible for Niemann-Pick C1 disease (Carstea, et al., (1997) Science 277:228–231). Niemann-Pick C1 disease is a rare genetic disorder in humans which results in accumulation of low density lipoprotein (LDL)-derived unesterified cholesterol in lysosomes (Pentchev, et al., (1994) Biochim. Biophys. Acta. 1225: 235–243 and Vanier, et al., (1991) Biochim. Biophys. Acta. 1096:328–337). In addition, cholesterol accumulates in the trans-golgi network of npc1⁻ cells, and relocation of cholesterol, to and from the plasma membrane, is delayed. NPC1 and NPC1L1 each possess 13 transmembrane spanning segments as well as a sterol-sensing domain (SSD). Several other proteins, including HMG-CoA Reductase (HMG-R), Patched (PTC) and Sterol Regulatory Element Binding Protein Cleavage-Activation Protein (SCAP), include an SSD which is involved in sensing cholesterol levels possibly by a mechanism which involves direct cholesterol binding (Gil, et al., (1985) Cell 41:249–258; Kumagai, et al., (1995) J. Biol. Chem. 270:19107–19113 and Hua, et al., (1996) Cell 87:415–426).

SUMMARY OF THE INVENTION

The present invention includes an isolated polypeptide comprising 42 or more contiguous amino acids from an amino acid sequence selected from SEQ ID NOs: 2 and 12, preferably comprising the amino acid sequence selected from SEQ ID NOs: 2 and 12. The present invention also comprises an isolated polypeptide comprising the amino acid sequence of SEQ ID NO: 4. The invention also includes an isolated polynucleotide encoding a polypeptide of SEQ ID NO: 2, 4 or 12, preferably comprising a nucleotide sequence selected from SEQ ID NOs: 1, 3, 5–10, 11 and 13. A recombinant vector comprising a polynucleotide of the invention is also provided along with a host cell comprising the vector.

The present invention also provides an isolated antibody which specifically binds to or was raised against NPC1L1 (e.g., rat NPC1L1, mouse NPC1L1 or human NPC1L1) or any antigenic fragment thereof, preferably rat NPC1L1, more preferably a polypeptide comprising an amino acid sequence selected from SEQ ID NO: 39–42. Preferably, the antibody is an isolated polyclonal or monoclonal antibody. In one embodiment, the antibody is obtained from a rabbit.

The present invention also includes a method for making an NPC1L1 polypeptide of the invention comprising culturing a host cell of the invention under conditions in which the nucleic acid in the cell which encodes the NPC1L1 polypeptide is expressed. Preferably, the method includes the step of isolating the polypeptide from the culture.

The present invention includes methods for identifying an agonist or antagonist of NPC1L1 comprising (a) contacting a host cell (e.g., chinese hamster ovary (CHO) cell, a J774 cell, a macrophage cell or a Caco2 cell) expressing a polypeptide comprising the amino acid sequence of SEQ ID NO: 2 or SEQ ID NO: 4 or SEQ ID NO: 12 or a functional fragment thereof on a cell surface, in the presence of a known amount of a detectably labeled (e.g., with $^3$H, $^{14}$C or $^{125}$I) substituted azetidinone (e.g., ezetimibe), with a sample to be tested for the presence of an NPC1L1 agonist or antagonist; and (b) measuring the amount of detectably labeled substituted azetidinone (e.g., ezetimibe) specifically bound to the polypeptide; wherein an NPC1L1 agonist or antagonist in the sample is identified by measuring substantially reduced binding of the detectably labeled substituted azetidinone (e.g., ezetimibe) to the polypeptide, compared to what would be measured in the absence of such an agonist or antagonist.

Another method for identifying an agonist or antagonist of NPC1L1 is also provided. The method comprises (a) placing, in an aqueous suspension, a plurality of support particles, impregnated with a fluorescer (e.g., yttrium silicate, yttrium oxide, diphenyloxazole and polyvinyltoluene), to which a host cell (e.g., chinese hamster ovary (CHO) cell, a J774 cell, a macrophage cell or a Caco2 cell) expressing a polypeptide comprising the amino acid sequence of SEQ ID NO: 2 or SEQ ID NO: 4 or SEQ ID NO: 12 or a functional fragment thereof on a cell surface are attached; (b) adding, to the suspension, a radiolabeled (e.g., with $^3$H, $^{14}$C or $^{251}$I) substituted azetidinone (e.g., ezetimibe) and a sample to be tested for the presence of an antagonist or agonist, wherein the radiolabel emits radiation energy capable of activating the fluorescer upon the binding of the substituted azetidinone (e.g., ezetimibe) to the polypeptide to produce light energy, whereas radiolabeled substituted azetidinone (e.g., ezetimibe) that does not bind to the polypeptide is, generally, too far removed from the support particles to enable the radioactive energy to activate the fluorescer; and (c) measuring the light energy emitted by the fluorescer in the suspension; wherein an NPC1L1 agonist or antagonist in the sample is identified by measuring substantially reduced light energy emission, compared to what would be measured in the absence of such an agonist or antagonist.

Also provided is a method for identifying an agonist or antagonist of NPC1L1 comprising (a) contacting a host cell (e.g., chinese hamster ovary (CHO) cell, a J774 cell, a macrophage cell or a Caco2 cell) expressing an polypeptide comprising an amino acid sequence of SEQ ID NO: 2 or SEQ ID NO: 4 or SEQ ID NO: 12 or a functional fragment thereof on a cell surface with detectably labeled (e.g., with $^3$H, $^{14}$C or $^{125}$I) sterol (e.g., cholesterol) or 5α-stanol and with a sample to be tested for the presence of an antagonist or agonist; and (b) measuring the amount of detectably labeled sterol (e.g., cholesterol) or 5α-stanol in the cell; wherein an NPC1L1 antagonist in the sample is identified by measuring substantially reduced detectably labeled sterol (e.g., cholesterol) or 5α-stanol within the host cell, compared to what would be measured in the absence of such an antagonist and wherein an NPC1L1 agonist in the sample is identified by measuring substantially increased detectably labeled sterol (e.g., cholesterol) or 5α-stanol within the host cell, compared to what would be measured in the absence of such an agonist.

The present invention includes methods for inhibiting NPC1L1-mediated intestinal sterol (e.g., cholesterol) or 5α-stanol uptake, in a subject, by administering a substance identified by the screening methods described herein to the subject. Such substances include compounds such as small molecule antagonists of NPC1L1 other than ezetimibe. Also contemplated are methods for antagonizing NPC1L1-mediated sterol (e.g., cholesterol) or 5α-stanol absorption by administering anti-NPC1L1 antibodies. NPC1L1-mediated absorption of sterol (e.g., cholesterol) or 5α-stanol can also be antagonized by any method which reduces expression of NPC1L1 in an organism. For example, NPC1L1 expression can be reduced by introduction of anti-sense NPC1L1 mRNA into a cell of an organism or by genetic mutation of the NPC1L1 gene in an organism (e.g., by complete knock-out, disruption, truncation or by introduction of one or more point mutations).

Also included in the present invention is a mutant transgenic mammal (e.g., mouse, rat, dog, rabbit, pig, guinea pig, cat, horse), preferably a mouse comprising a homozygous or heterozygous mutation (e.g., disruption, truncation, one or more point mutations, knock out) of endogenous, chromosomal NPC1L1 wherein, preferably, the mouse does not produce any functional NPC1L1 protein. Preferably, the mutant mouse, lacking functional NPC1L1, exhibits a reduced level of intestinal sterol (e.g., cholesterol) or 5α-stanol absorption and/or a reduced level of serum sterol (e.g., cholesterol) or 5α-stanol and/or a reduced level of liver sterol (e.g., cholesterol) or 5α-stanol as compared to that of a non-mutant mouse comprising functional NPC1L1. Preferably, in the mutant mouse chromosome, the region of NPC1L1 (SEQ ID NO: 45) deleted is from nucleotide 790 to nucleotide 998. In one embodiment, NPC1L1 (SEQ ID NO: 11) is deleted from nucleotide 767 to nucleotide 975. Any offspring or progeny of a parent NPC1L1 mutant mouse (i.e., npcl11) of the invention which has inherited an npcl11 mutant allele is also part of the present invention.

The scope of the present invention also includes a method for screening a sample for an intestinal sterol (e.g., cholesterol) or 5α-stanol absorption antagonist comprising (a) feeding a sterol (e.g., cholesterol) or 5α-stanol-containing substance (e.g., comprising radiolabeled cholesterol, such as $^{14}$C-cholesterol or $^3$H-cholesterol) to a first and second mouse comprising a functional NPC1L1 gene and to a third, mutant mouse lacking a functional NPC1L1; (b) administering the sample to the first mouse comprising a functional NPC1L1 but not to the second mouse; (c) measuring the amount of sterol (e.g., cholesterol) or 5α-stanol absorption in the intestine of said first, second and third mouse (e.g., by measuring serum cholesterol); and (d) comparing the levels of intestinal sterol (e.g., cholesterol) or 5α-stanol absorption in each mouse; wherein the sample is determined to contain the intestinal sterol (e.g., cholesterol) or 5α-stanol absorption antagonist when the level of intestinal sterol (e.g., cholesterol) or 5α-stanol absorption in the first mouse and third mouse are less than the amount of intestinal sterol (e.g., cholesterol) or 5α-stanol absorption in the second mouse.

The present invention also encompasses a kit comprising (a) a substituted azetidinone (e.g., ezetimibe) in a pharmaceutical dosage form (e.g., a pill or tablet comprising 10 mg substituted azetidinone (e.g., ezetimibe)); and (b) information, for example in the form of an insert, indicating that NPC1L1 is a target of ezetimibe. The kit may also include simvastatin in a pharmaceutical dosage form (e.g., a pill or tablet comprising 5 mg, 10 mg, 20 mg, 40 mg or 80 mg simvastatin). The simvastatin in pharmaceutical dosage form and the ezetimibe in pharmaceutical dosage form can be associated in a single pill or tablet or in separate pills or tablets.

The present invention also provides any isolated mammalian cell (e.g., isolated mouse cell, isolated rat cell or isolated human cell) which lacks a gene which encodes or can produce a functional NPC1L1 polypeptide. The isolated cell can be isolated from a mutant mouse comprising a homozygous mutation of endogenous, chromosomal NPC1L1 wherein the mouse does not produce any functional NPC1L1 protein. Further, the mutation can be in a gene which when un-mutated encodes an amino acid sequence of SEQ ID NO: 12 (e.g., comprising a nucleotide sequence of SEQ ID NO: 11). The cell can be isolated or derived from duodenum, gall bladder, liver, small intestine or stomach tissue. The cell can be an enterocyte.

DETAILED DESCRIPTION OF THE INVENTION

The present invention includes an NPC1L1 polypeptide from rat, human and from mouse along with polynucleotides encoding the respective polypeptides. Preferably, the rat NPC1L1 polypeptide comprises the amino acid sequence set forth in SEQ ID NO: 2, the human NPC1L1 comprises the amino acid sequence set forth in SEQ ID NO: 4 and the mouse NPC1L1 polypeptide comprises the amino acid sequence set forth in SEQ ID NO.12. The rat NPC1L1 polynucleotide of SEQ ID NO:1 or 10 encodes the rat NPC1L1 polypeptide. The human NPC1L1 polynucleotide of SEQ ID NO:3 encodes the human NPC1L1 polypeptide. The mouse NPC1L1 polynucleotide of SEQ ID NO: 11 or 13 encodes the mouse NPC1L1 polypeptide.

The present invention includes any isolated polynucleotide or isolated polypeptide comprising a nucleotide or amino acid sequence referred to, below, in Table 1.

TABLE 1

Polynucleotides and Polypeptides of the Invention.

| Polynucleotide or Polypeptide | Sequence Identifier |
|---|---|
| Rat NPC1L1 polynucleotide | SEQ ID NO: 1 |
| Rat NPC1L1 polypeptide | SEQ ID NO: 2 |
| Human NPC1L1 polynucleotide | SEQ ID NO: 3 |
| Human NPC1L1 polypeptide | SEQ ID NO: 4 |
| Rat NPC1L1 expressed sequence tag 603662080F1 (partial sequence) | SEQ ID NO: 5 |
| Rat NPC1L1 expressed sequence tag 603665037F1 (partial sequence) | SEQ ID NO: 6 |
| Rat NPC1L1 expressed sequence tag 604034587F1 (partial sequence) | SEQ ID NO: 7 |
| EST 603662080F1 with downstream sequences added | SEQ ID NO: 8 |
| EST 603662080F1 with upstream and downstream sequences added | SEQ ID NO: 9 |
| Back-translated polynucleotide sequence of rat NPC1L1 | SEQ ID NO: 10 |
| Mouse NPC1L1 polynucleotide | SEQ ID NO: 11 |
| Mouse NPC1L1 polypeptide | SEQ ID NO: 12 |
| Back-translated polynucleotide sequence of mouse NPC1L1 | SEQ ID NO: 13 |

TABLE 1-continued

Polynucleotides and Polypeptides of the Invention.

| Polynucleotide or Polypeptide | Sequence Identifier |
|---|---|
| Back-translated polynucleotide sequence of human NPC1L1 | SEQ ID NO: 51 |

A human NPC1L1 is also disclosed under Genbank Accession Number AF192522. As discussed below, the nucleotide sequence of the rat NPC1L1 set forth in SEQ ID NO: 1 was obtained from an expressed sequence tag (EST) from a rat jejunum enterocyte cDNA library. SEQ ID NOs: 5–7 include partial nucleotide sequences of three independent cDNA clones. The downstream sequence of the SEQ ID NO: 5 EST (603662080F1) were determined; the sequencing data from these experiments are set forth in SEQ ID NO: 8. The upstream sequences were also determined; these data are set forth in SEQ ID NO: 9.

SEQ ID NOs: 43 and 44 are the nucleotide and amino acid sequence, respectively, of human NPC1L1 which is disclosed under Genbank Accession No.: AF 192522 (see Davies, et al., (2000) Genomics 65(2):137–45).

SEQ ID NO: 45 is the nucleotide sequence of a mouse NPC1L1 which is disclosed under Genbank Accession No. AK078947.

NPC1L1 mediates intestinal sterol (e.g., cholesterol) or 5α-stanol absorption. Inhibition of NPC1L1 in a patient is a useful method for reducing intestinal sterol (e.g., cholesterol) or 5α-stanol absorption and serum sterol (e.g., cholesterol) or 5α-stanol in the patient. Reducing the level of intestinal sterol (e.g., cholesterol) or 5α-stanol absorption and serum sterol (e.g., cholesterol) or 5α-stanol in a patient is a useful way in which to treat or prevent the occurrence of atherosclerosis, particularly diet-induced atherosclerosis.

As used herein, the term "sterol" includes, but is not limited to, cholesterol and phytosterols (including, but not limited to, sitosterol, campesterol, stigmasterol and avenosterol)).

As used herein, the term "5α-stanol" includes, but is not limited to, cholestanol, 5α-campestanol and 5α-sitostanol.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

The back-translated sequences of SEQ ID NO: 10 and of SEQ ID NO: 13 uses the single-letter code shown in Table 1 of Annex C, Appendix 2 of the PCT Administrative Instruction in the Manual of Patent Examination Procedure.

A "polynucleotide", "nucleic acid" or "nucleic acid molecule" may refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

The present invention includes nucleic acid fragments of any of SEQ ID NOs: 1, 5–11 or 13. A nucleic acid "fragment" includes at least about 30 (e.g., 31, 32, 33, 34), preferably at least about 35 (e.g, 25, 26, 27, 28, 29, 30, 31, 32, 33 or 34), more preferably at least about 45 (e.g., 35, 36, 37, 38, 39, 40, 41, 42, 43 or 44), and most preferably at least about 126 or more contiguous nucleotides (e.g., 130, 131, 132, 133, 134, 135, 136, 137, 138, 139, 140, 150, 160, 170, 180, 190, 200, 300, 400, 500, 1000 or 1200) from any of SEQ ID NOs: 1, 5–11 or 13.

The present invention also includes nucleic acid fragments consisting of at least about 7 (e.g., 9, 12, 17, 19), preferably at least about 20 (e.g., 30, 40, 50, 60), more preferably about 70 (e.g., 80, 90, 95), yet more preferably at least about 100 (e.g., 105, 110, 114) and even more preferably at least about 115 (e.g., 117, 119, 120, 122, 124, 125, 126) contiguous nucleotides from any of SEQ ID NOs: 1, 5–11 or 13.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" may refer to a series of two or more amino acids in a protein, peptide or polypeptide.

"Protein", "peptide" or "polypeptide" includes a contiguous string of two or more amino acids. Preferred peptides of the invention include those set forth in any of SEQ ID NOs: 2 or 12 as well as variants and fragments thereof. Such fragments preferably comprise at least about 10 (e.g., 11, 12, 13, 14, 15, 16,.17, 18 or 19), more preferably at least about 20 (e.g., 21, 22, 23, 24, 25, 26, 27, 28, 29, 30, 35, 40), and yet more preferably at least about 42 (e.g., 43, 44, 45, 46, 47, 48, 49, 50, 60, 70, 80, 90, 100, 110, 120 or 130) or more contiguous amino acid residues from any of SEQ ID NOs: 2 or 12.

The present invention also includes polypeptides, preferably antigenic polypeptides, consisting of at least about 7 (e.g., 9, 10, 13, 15, 17, 19), preferably at least about 20 (e.g., 22, 24, 26, 28), yet more preferably at least about 30 (e.g., 32, 34, 36, 38) and even more preferably at least about 40 (e.g., 41, 42) contiguous amino acids from any of SEQ ID NOs: 2 or 12.

The polypeptides of the invention can be produced by proteolytic cleavage of an intact peptide, by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies and fragments thereof. The antibodies can be used, e.g., in immunoassays for immunoaffinity purification or for inhibition of NPC1L1, etc.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used herein may denote the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Preferred host cells include chinese hamster ovary (CHO) cells, murine macrophage J774 cells or any other macrophage cell line and human intestinal epithelial Caco2 cells.

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304–310), the promoter contained in the 3' long terminal repeat of Rous sarcoma virus (Yamamoto, et al., (1980) Cell 22:787–797), the herpes thymidine kinase promoter (Wagner, et al., (1981) Proc. Natl. Acad. Sci. USA 78:1441–1445), the regulatory sequences of the metallothionein gene (Brinster, et al., (1982) Nature 296:39–42); prokaryotic expression vectors such as the β-lactamase promoter (Villa-Komaroff, et al., (1978) Proc. Natl. Acad. Sci. USA 75:3727–3731), or the tac promoter (DeBoer, et al., (1983) Proc. Natl. Acad. Sci. USA 80:21–25); see also "Useful proteins from recombinant bacteria" in Scientific American (1980) 242:74–94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., Cloning Vectors: A Laboratory Manual, 1985 and Supplements, Elsevier, N.Y., and Rodriguez et al. (eds.), Vectors: A Survey of Molecular Cloning Vectors and Their Uses, 1988, Buttersworth, Boston, Mass.

The term "expression system" means a host cell and compatible vector which, under suitable conditions, can express a protein or nucleic acid which is carried by the vector and introduced to the host cell. Common expression systems include E. coli host cells and plasmid vectors, insect host cells and Baculovirus vectors, and mammalian host cells and vectors.

Expression of nucleic acids encoding the NPC1L1 polypeptides of this invention can be carried out by conventional methods in either prokaryotic or eukaryotic cells. Although E. coli host cells are employed most frequently in prokaryotic systems, many other bacteria, such as various strains of Pseudomonas and Bacillus, are known in the art and can be used as well. Suitable host cells for expressing nucleic acids encoding the NPC1L1 polypeptides include prokaryotes and higher eukaryotes. Prokaryotes include both gram-negative and gram-positive organisms, e.g., E. coli and B. subtilis. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC18 or 19). Vectors that can be used to express the NPC1L1 polypeptides include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) Vectors: A Survey of Molecular Cloning Vectors and Their Uses, 1988, Buttersworth, Boston, pp. 205–236. Many polypeptides can be expressed, at high levels, in an E.coli/T7 expression system as disclosed in U.S. Pat. Nos. 4,952,496, 5,693,489 and 5,869,320 and in Davanloo, P., et al., (1984) Proc. Natl. Acad. Sci. USA 81: 2035–2039; Studier, F. W., et al., (1986) J. Mol. Biol. 189: 113–130; Rosenberg, A. H., et al., (1987) Gene 56: 125–135; and Dunn, J. J., et al., (1988) Gene 68: 259.

Higher eukaryotic tissue culture cells may also be used for the recombinant production of the NPC1L1 polypeptides of the invention. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, chinese hamster ovary (CHO) cell lines, J774 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pCDNA1, pCD (Okayama, et al., (1985) Mol. Cell Biol. 5:1136), pMC1neo Poly-A (Thomas, et al., (1987) Cell 51:503), pREP8, pSVSPORT and derivatives thereof, and baculovirus vectors such as pAC373 or pAC610. One embodiment of the invention includes membrane bound NPC1L1. In this embodiment, NPC1L1 can be expressed in the cell membrane of a eukaryotic cell and the membrane bound protein can be isolated from the cell by conventional methods which are known in the art.

The present invention also includes fusions which include the NPC1L1 polypeptides and NPC1L1 polynucleotides of the present invention and a second polypeptide or polynucleotide moiety, which may be referred to as a "tag". The fusions of the present invention may comprise any of the polynucleotides or polypeptides set forth in Table 1 or any subsequence or fragment thereof (discussed above). The fused polypeptides of the invention may be conveniently constructed, for example, by insertion of a polynucleotide of the invention or fragment thereof into an expression vector. The fusions of the invention may include tags which facilitate purification or detection. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, 123I, $^{111}In$ and $^{68}Ga$ may also be used to label the polypeptides and polynucleotides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. An insect cell which may be used in this invention is any cell derived from an organism of the class Insecta. Preferably, the insect is *Spodoptera fruigiperda* (Sf9 or Sf21) or *Trichoplusia ni* (High 5). Examples of insect expression systems that can be used with the present invention, for example to produce NPC1L1 polypeptide, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

Other modifications may also include addition of aliphatic esters or amides to the polypeptide carboxyl terminus. The present invention also includes analogs of the NPC1L1 polypeptides which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties. For example, the NPC1L1 polypeptides of the invention may be appended with a polymer which increases the half-life of the peptide in the body of a subject. Preferred polymers include polyethylene glycol (PEG) (e.g., PEG with a molecular weight of 2 kDa, 5 kDa, 10 kDa, 12 kDa, 20 kDa, 30 kDa and 40 kDa), dextran and monomethoxypolyethylene glycol (mPEG).

The peptides of the invention may also be cyclized. Specifically, the amino- and carboxy-terminal residues of an NPC1L1 polypeptide or two internal residues of an NPC1L1 polypeptide of the invention can be fuised to create a cyclized peptide. Methods for cyclizing peptides are conventional and very well known in the art; for example see Gurrath, et al., (1992) Eur. J. Biochem. 210:911–921.

The present invention contemplates any superficial or slight modification to the amino acid or nucleotide sequences which correspond to the polypeptides of the invention. In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes polynucleotides encoding rat, human or mouse NPC1L1 and fragments thereof as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5×or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50–9.51). For hybridization with shorter nucleic acids, i.e., oligonucleotides, the position of mismatches becomes more important, and the length of the oligonucleotide determines its specificity (see Sambrook, et al., supra).

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference rat NPC1L1 nucleotide (e.g., any of SEQ ID NOs: 1 or 5–10) and amino acid sequences (e.g., SEQ ID NO: 2), reference human NPC1L1 nucleotide (e.g., SEQ ID NO: 3) and amino acid sequences (e.g., SEQ ID NO: 4) or the reference mouse NPC1L1 nucleotide (e.g., any of SEQ ID NOs: 11 or 13) and amino acids sequences (e.g., SEQ ID NO: 12), when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference rat NPC1L1 amino acid sequence of SEQ ID NO: 2, reference human NPC1L1 amino acid sequence of SEQ ID NO: 4 or the reference mouse NPC1L1 amino acid sequence of SEQ ID NO: 12, when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between non-identical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215: 403–410; Gish, W., et al., (1993) Nature Genet. 3:266–272; Madden, T. L., et al., (1996) Meth. Enzymol. 266:131–141; Altschul, S. F., et al., (1997) Nucleic Acids Res. 25:3389–3402; Zhang, J., et al., (1997) Genome Res. 7:649–656; Wootton, J. C., et al., (1993) Comput. Chem. 17:149–163; Hancock, J. M., et al., (1994) Comput. Appl. Biosci. 10:67–70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345–352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353–358, Natl. Biomed. Res. Found., Washington, D.C.; Altschul, S. F., (1991) J. Mol. Biol. 219:555–565; States, D. J., et al., (1991) Methods 3:66–70; Henikoff, S., et al., (1992) Proc. Natl. Acad. Sci. USA 89:10915–10919; Altschul, S. F., et al., (1993) J. Mol. Evol. 36:290–300; ALIGNMENT STATISTICS: Karlin, S., et al., (1990) Proc. Natl. Acad. Sci. USA 87:2264–2268; Karlin, S., et al., (1993) Proc. Natl. Acad. Sci. USA 90:5873–5877; Dembo, A., et al., (1994) Ann. Prob. 22:2022–2039; and Altschul, S. F. "Evaluating the statistical significance of multiple distinct local alignments." in *Theoretical and Computational Methods in Genome Research* (S. Suhai, ed.), (1997) pp. 1–14, Plenum, N.Y.

Protein Purification

The proteins, polypeptides and antigenic fragments of this invention can be purified by standard methods, including, but not limited to, salt or alcohol precipitation, affinity chromatography (e.g., used in conjunction with a purification tagged NPC1L1 polypeptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "*Guide to Protein Purification*", *Methods in Enzynology*, Vol. 182, M. Deutscher, Ed., 1990, Academic Press, New York, N.Y.

Purification steps can be followed by performance of assays for receptor binding activity as described below. Particularly where an NPC1L1 polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Antibody Molecules

Antigenic (including immunogenic) fragments of the NPC1L1 polypeptides of the invention are within the scope of the present invention (e.g., 42 or more contiguous amino acids from SEQ ID NO: 2, 4 or 12). The antigenic peptides may be useful, inter alia, for preparing isolated antibody molecules which recognize NPC1L1. Isolated anti-NPC1L1 antibody molecules are usefuil NPC1L1 antagonists.

An antigen is any molecule that can bind specifically to an antibody. Some antigens cannot, by themselves, elicit antibody production. Those that can induce antibody production are immunogens.

Preferably, isolated anti-NPC1L1 antibodies recognize an antigenic peptide comprising an amino acid sequence selected from SEQ ID NOs: 39–42 (e.g., an antigen derived from rat NPC1L1). More preferably, the antibody is A0715, A0716, A0717, A0718, A0867, A0868, A1801 or A1802.

The term "antibody molecule" includes, but is not limited to, antibodies and fragments (preferably antigen-binding fragments) thereof. The term includes monoclonal antibodies, polyclonal antibodies, bispecific antibodies, Fab antibody fragments, F(ab)$_2$ antibody fragments, Fv antibody fragments (e.g., $V_H$ or $V_L$), single chain Fv antibody fragments and dsFv antibody fragments. Furthermore, the antibody molecules of the invention may be fuilly human antibodies, mouse antibodies, rat antibodies, rabbit antibodies, goat antibodies, chicken antibodies, humanized antibodies or chimeric antibodies.

Although it is not always necessary, when NPC1L1 polypeptides are used as antigens to elicit antibody production in an immunologically competent host, smaller antigenic fragments are, preferably, first rendered more immunogenic by cross-linking or concatenation, or by coupling to an immunogenic carrier molecule (i.e., a macromolecule having the property of independently eliciting an immunological response in a host animal, such as diptheria toxin or tetanus). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Carrier molecules include, e.g., proteins and natural or synthetic polymeric compounds such as polypeptides, polysaccharides, lipopolysaccharides etc. Protein carrier molecules are especially preferred, including, but not limited to, keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water-soluble carboduimides such as dicyclohexylcarbodiimide or glutaraldehyde.

Coupling agents, such as these, can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Adjuvants for the vaccination of animals include, but are not limited to, Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays*, 3rd Edition, 1987, Elsevier, N.Y. Other useful references covering methods for preparing polyclonal antisera include *Microbiology*, 1969, Hoeber Medical Division, Harper and Row; Landsteiner, *Specificity of Serological Reactions*, 1962, Dover Publications, New York, and Williams, et al., *Methods in Immunology and Immunochemistry*, Vol. 1, 1967, Academic Press, New York.

The anti-NPC1L1 antibody molecules of the invention preferably recognize human, mouse or rat NPC1L1; however, the present invention includes antibody molecules which recognize NPC1L1 from any species, preferably mammals (e.g., cat, sheep or horse). The present invention also includes complexes comprising an NPC1L1 polypeptide of the invention and an anti-NPC1L1 antibody molecule. Such complexes can be made by simply contacting the antibody molecule with its cognate polypeptide.

Various methods may be used to make the antibody molecules of the invention. Human antibodies can be made, for example, by methods which are similar to those disclosed in U.S. Pat. Nos. 5,625,126; 5,877,397; 6,255,458; 6,023,010 and 5,874,299.

Hybridoma cells which produce the monoclonal anti-NPC1L1 antibodies may be produced by methods which are commonly known in the art. These methods include, but are not limited to, the hybridoma technique originally developed by Kohler, et al., (1975) (Nature 256:495–497), as well as the trioma technique (Hering, et al., (1988) Biomed. Biochim. Acta. 47:211–216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026–2030), and the EBV-hybridoma technique (Cole, et al., in *Monoclonal Antibodies and Cancer Therapy*, Alan R. Liss, Inc., pp. 77–96, 1985). ELISA may be used to determine if hybridoma cells are expressing anti-NPC1L1 antibodies.

The anti-NPC1L1 antibody molecules of the present invention may also be produced recombinantly (e.g., in an *E.coli*/T7 expression system as discussed above). In this embodiment, nucleic acids encoding the antibody molecules of the invention (e.g., $V_H$ or $V_L$) may be inserted into a pet-based plasmid and expressed in the *E.coli*/T7 system. There are several methods by which to produce recombinant antibodies which are known in the art. An example of a method for recombinant production of antibodies is disclosed in U.S. Pat. No. 4,816,567. See also Skerra, A., et al., (1988) Science 240:1038–1041; Better, M., et al., (1988) Science 240:1041–1043 and Bird, R. E., et al., (1988) Science 242:423–426.

The term "monoclonal antibody," includes an antibody obtained from a population of substantially homogeneous antibodies, i.e., the individual antibodies comprising the population are identical except for possible, naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies to be used in accordance with the present invention may be made by the hybridoma method as described by Kohler, et al., (1975) Nature 256:495.

The term "polyclonal antibody" includes an antibody which was produced among or in the presence of one or more other, non-identical antibodies. In general, polyclonal antibodies are produced from a B-lymphocyte in the presence of several other B-lymphocytes which produced non-identical antibodies. Typically, polyclonal antibodies are obtained directly from an immunized animal (e.g., a rabbit).

A "bispecific antibody" comprises two different antigen binding regions which bind to distinct antigens. Bispecific antibodies, as well as methods of making and using the antibodies, are conventional and very well known in the art.

Anti-idiotypic antibodies or anti-idiotypes are antibodies directed against the antigen-combining region or variable region (called the idiotype) of another antibody molecule. As disclosed by Jerne (Jerne, N. K., (1974) Ann. Immunol.

(Paris) 125c:373 and Jerne, N. K., et al., (1982) EMBO 1:234), immunization with an antibody molecule expressing a paratope (antigen-combining site) for a given antigen (e.g., NPC1L1) will produce a group of anti-antibodies, some of which share, with the antigen, a complementary structure to the paratope. Immunization with a subpopulation of the anti-idiotypic antibodies will, in turn, produce a subpopulation of antibodies or immune cell subsets that are reactive to the initial antigen.

The term "fully human antibody" refers to an antibody which comprises human immunoglobulin sequences only. Similarly, "mouse antibody" refers to an antibody which comprises mouse immunoglobulin sequences only.

"Human/mouse chimeric antibody" refers to an antibody which comprises a mouse variable region ($V_H$ and $V_L$) fused to a human constant region.

"Humanized" anti-NPC1L1 antibodies are also within the scope of the present invention. Humanized forms of non-human (e.g., murine) antibodies are chimeric immunoglobulins, which contain minimal sequence derived from non-human immunoglobulin. For the most part, humanized antibodies are human immunoglobulins (recipient antibody) in which residues from a complementary determining region of the recipient are replaced by residues from a complementary determining region of a nonhuman species (donor antibody), such as mouse, rat or rabbit, having a desired specificity, affinity and capacity. In some instances, Fv framework residues of the human immunoglobulin are also replaced by corresponding non-human residues.

"Single-chain Fv" or "sFv" antibody fragments include the $V_H$ and/or $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786; 5,132,405 and 4,946,778) can be adapted to produce anti-NPC1L1 specific, single chain antibodies. For a review of sFv see Pluckthun in *The Pharmacology of Monoclonal Antibodies*, vol. 113, Rosenburg and Moore eds. Springer-Verlag, N.Y., pp. 269–315 (1994).

"Disulfide stabilized Fv fragments" and "dsFv" include molecules having a variable heavy chain ($V_H$) and/or a variable light chain ($V_L$) which are linked by a disulfide bridge.

Antibody fragments within the scope of the present invention also include $F(ab)_2$ fragments which may be produced by enzymatic cleavage of an IgG by, for example, pepsin. Fab fragments may be produced by, for example, reduction of $F(ab)_2$ with dithiothreitol or mercaptoethylamine.

An $F_V$ fragment is a $V_L$ or $V_H$ region.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g., IgG-1, IgG-2, IgG-3 and IgG-4; IgA-1 and IgA-2.

The anti-NPC1L1 antibody molecules of the invention may also be conjugated to a chemical moiety. The chemical moiety may be, inter alia, a polymer, a radionuclide or a cytotoxic factor. Preferably, the chemical moiety is a polymer which increases the half-life of the antibody molecule in the body of a subject. Suitable polymers include, but are by no means limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxy-polyethylene glycol (mPEG). Methods for producing PEGylated anti-IL8 antibodies which are described in U.S. Pat. No. 6,133,426 can be applied to the production of PEGylated anti-NPC1L1 antibodies of the invention. Lee, et al., (1999) (Bioconj. Chem. 10:973–981) discloses PEG conjugated single-chain antibodies. Wen, et al., (2001) (Bioconj. Chem. 12:545–553) discloses conjugating antibodies with PEG which is attached to a radiometal chelator (diethylenetriaminpentaacetic acid (DTPA)).

The antibody molecules of the invention may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, $^{40}K$, $^{157}Gd$, $^{55}Mn$, $^{52}Tr$ or $^{56}Fe$.

The antibody molecules of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407.

Methods for conjugating antibodies are conventional and very well known in the art.

Screening Assays

The invention allows the discovery of selective agonists and antagonists of NPC1L1 (e.g., SEQ ID NO: 2, 4 or 12) that may be useful in treatment and management of a variety of medical conditions including elevated serum sterol (e.g., cholesterol) or 5α-stanol. Thus, NPC1L1 of this invention can be employed in screening systems to identify agonists or antagonists. Essentially, these systems provide methods for bringing together NPC1L1, an appropriate, known ligand or agonist or antagonist, including a sterol (e.g., cholesterol, phytosterols (including, but not limited to, sitosterol, campesterol, stigmasterol and avenosterol)), a cholesterol oxidation product, a 5α-stanol (including but not limited to cholestanol, 5α-campestanol and 5α-sitostanol), a substituted azetidinone (e.g., ezetimibe), BODIPY-ezetimibe (N-(4,4-difluoro-5.7-dimethyl-4-bora-3a.4a-diaza-s-indacene-3-vl)methyl iodoacetamide/ezetimibe) (Altmann, et al., (2002) Biochim. Biophys. Acta 1580(1):77–93) or 4", 6"-bis [(2-fluorophenyl)carbamoyl]-beta-D-cellobiosyl derivative of 11-ketotigogenin as described in DeNinno, et al., (1997) (J. Med. Chem. 40(16):2547–54) (Merck; L-166,143) or any substituted azetidinone, and a sample to be tested for the presence of an NPC1L1 agonist or antagonist.

The term "specific" when used to describe binding of, for example, a ligand or antagonist of NPC1L1 in a screening assay is a term of art which refers to the extent by which the ligand or antagonist (e.g., detectably labeled substituted azetidinone, detectably labeled ezetimibe, detectably labeled sterol (e.g., cholesterol) or detectably labeled 5α-stanol) binds preferentially to NPC1L1 over that of other proteins in the assay system. For example, an antagonist or ligand of NPC1L1 binds specifically to NPC1L1 when the signal generated in the assay to indicate such binding exceeds, to any extent, a background signal in a negative control experiment wherein, for example, NPC1L1 or the antagonist or ligand is absent. Furthermore, "specific binding" includes binding of an antagonist or ligand either directly to NPC1L1 or indirectly, for example via another moiety, in a complex of which NPC1L1 is a part. The moiety to which an NPC1L1 ligand or antagonist binds can be another protein or a post-translational modification of NPC1L1 (e.g., a lipid chain or a carbohydrate chain).

Non-limiting examples of suitable azetidinones include those disclosed in U.S. Pat. Nos. RE37,721; 5,631,365; 5,767,115; 5,846,966; 5,688,990; 5,656,624; 5,624,920; 5,698,548 and 5,756,470 and U.S. Patent Application Publication No. 2003/0105028-each of which is herein incorporated by reference in its entirety.

A convenient method by which to evaluate whether a sample contains an NPC1L1 agonist or antagonist is to determine whether the sample contains a substance which competes for binding between the known agonist or antagonist (e.g., ezetimibe) and NPC1L1.

Ezetimibe can be prepared by a variety of methods well know to those skilled in the art, for example such as are disclosed in U.S. Pat. Nos. 5,631,365, 5,767,115, 5,846,966, 6,207,822, U.S. Patent Application Publication No. 2002/0193607 and PCT Patent Application WO 93/02048, each of which is incorporated herein by reference in its entirety.

"Sample", "candidate compound" or "candidate substance" refers to a composition which is evaluated in a test or assay, for example, for the ability to agonize or antagonize NPC1L1 (e.g., SEQ ID NO: 2, 4 or 12) or a functional fragment thereof. The composition may small molecules, peptides, nucleotides, polynucleotides, subatomic particles (e.g., α particles, β particles) or antibodies.

Two basic types of screening systems that can be used include, a labeled-ligand binding assay (e.g., direct binding assay or scintillation proximity assay (SPA)) and a "sterol (e.g., cholesterol) or 5α-stanol uptake" assay. A labeled ligand, for use in the binding assay, can be obtained by labeling a sterol (e.g., cholesterol) or a 5α-stanol or a known NPC1L1 agonist or antagonist with a measurable group (e.g., $^{125}$I or $^3$H). Various labeled forms of sterols (e.g., cholesterol) or 5α-stanols are available commercially or can be generated using standard techniques (e.g., Cholesterol-[1,2-$^3$H(N)], Cholesterol-[1,2,6,7-$^3$H(N)] or Cholesterol-[7-$^3$H(N)]; American Radiolabeled Chemicals, Inc; St. Louis, Mo.). In a preferred embodiment, ezetimibe is fluorescently labeled with a BODIPY group (Altmann, et al., (2002) Biochim. Biophys. Acta 1580(1):77–93) or labeled with a detectable group such as $^{125}$I or $^3$H.

Direct Binding Assay. Typically, a given amount of NPC1L1 of the invention (e.g., SEQ ID NO: 2, 4 or 12) or a complex including NPC1L1 is contacted with increasing amounts of labeled ligand or known antagonist or agonist (discussed above) and the amount of the bound, labeled ligand or known antagonist or agonist is measured after removing unbound, labeled ligand or known antagonist or agonist by washing. As the amount of the labeled ligand or known agonist or antagonist is increased, a point is eventually reached at which all receptor binding sites are occupied or saturated. Specific receptor binding of the labeled ligand or known agonist or antagonist is abolished by a large excess of unlabeled ligand or known agonist or antagonist.

Preferably, an assay system is used in which non-specific binding of the labeled ligand or known antagonist or agonist to the receptor is minimal. Non-specific binding is typically less than 50%, preferably less than 15%, and more preferably less than 10% of the total binding of the labeled ligand or known antagonist or agonist.

A nucleic acid encoding an NPC1L1 polypeptide of the invention (e.g., SEQ ID NO: 2, 4 or 12) can be transfected into an appropriate host cell, whereby the receptor will become incorporated into the membrane of the cell. A membrane fraction can then be isolated from the cell and used as a source of the receptor for assay. Alternatively, the whole cell expressing the receptor in the cell surface can be used in an assay. Preferably, specific binding of the labeled ligand or known antagonist or agonist to an untransfected/untransforned host cell or to a membrane fraction from an untransfected/untransformed host cell will be negligible.

In principle, a binding assay of the invention could be carried out using a soluble NPC1L1 polypeptide of the invention, e.g., following production and refolding by standard methods from an *E. coli* expression system, and the resulting receptor-labeled ligand complex could be precipitated, e.g., using an antibody against the receptor. The precipitate could then be washed and the amount of the bound, labeled ligand or antagonist or agonist could be measured.

In the basic binding assay, the method for identifying an NPC1L1 agonist or antagonist includes:
  (a) contacting NPC1L1 (e.g., SEQ ID NO: 2 or 4 or 12), a subsequence thereof or a complex including NPC1L1, in the presence of a known amount of labeled sterol (e.g., cholesterol) or 5α-stanol or known antagonist or agonist (e.g., labeled ezetimibe or labeled L-166, 143) with a sample to be tested for the presence of an NPC1L1 agonist or antagonist; and
  (b) measuring the amount of labeled sterol (e.g., cholesterol) or 5α-stanol or known antagonist or agonist directly or indirectly bound to NPC1L1.

An NPC1L1 antagonist or agonist in the sample is identified by measuring substantially reduced direct or indirect binding of the labeled sterol (e.g., cholesterol) or 5α-stanol or known agonist or antagonist to NPC1L1, compared to what would be measured in the absence of such an antagonist or agonist. For example, reduced direct or indirect binding between [$^3$H]-cholesterol and NPC1L1 in the presence of a sample might suggest that the sample contains a substance which is competing against [$^3$H]-cholesterol for NPC1L1 binding.

This assay can include a control experiment lacking any NPC1L1-dependent ligand (e.g., sterol such as cholesterol or 5α-stanol) binding. In this assay, for example, a whole cell or cell membrane lacking any functional NPC1L1, for example, a cell or membrane isolated or derived from a transgenic mutant npc1l1⁻ mouse of the invention, is assayed for ligand binding. When screening a sample for the presence of an NPC1L1 antagonist, it is useful to compare the level of binding observed in the presence of a sample being tested with that of a control experiment, as described herein, which completely lacks NPC1L1-dependent binding. Ideally, though by no means necessarily, the level of binding seen in the presence of a sample containing an antagonist will be similar to that of the control experiment.

Alternatively, a sample can be tested directly for binding to NPC1L1 (e.g., SEQ ID NO: 2, 4 or 12). A basic assay of this type may include the following steps:

(a) contacting NPC1L1 (e.g., SEQ ID NO: 2 or 4 or 12), a subsequence thereof or a complex including NPC1L1 with a labeled candidate compound (e.g., [$^3$H]-ezetimibe); and (b) detecting direct or indirect binding between the labeled candidate compound and NPC1L1.

Again, these experiment can be performed along with a control experiment wherein NPC1L1-dependent binding is completely lacking. For example, the assay can be performed using a whole cell or cell membrane lacking any functional NPC1L1 (e.g., cell or cell membrane derived from a transgenic, mutant npc1l1$^-$ mouse as described herein).

A candidate compound which is found to bind to NPC1L1 may function as an agonist or antagonist of NPC1L1 (e.g., by inhibition of sterol (e.g., cholesterol) or 5α-stanol uptake).

SPA Assay. NPC1L1 antagonists or agonists may also be measured using scintillation proximity assays (SPA). SPA assays are conventional and very well known in the art; see, for example, U.S. Pat. No. 4,568,649. In SPA, the target of interest is immobilised to a small microsphere approximately 5 microns in diameter. The microsphere, typically, includes a solid scintillant core which has been coated with a polyhydroxy film, which in turn contains coupling molecules, which allow generic links for assay design. When a radioisotopically labeled molecule binds to the microsphere, the radioisotope is brought into close proximity to the scintillant and effective energy transfer from electrons emitted by the isotope will take place resulting in the emission of light. While the radioisotope remains in free solution, it is too distant from the scintillant and the electron will dissipate the energy into the aqueous medium and therefore remain undetected. Scintillation may be detected with a scintillation counter. In general, $^3$H and $^{125}$I labels are well suited to SPA.

For the assay of receptor-mediated binding events, the lectin wheat germ agglutinin (WGA) may be used as the SPA bead coupling molecule (Amersham Biosciences; Piscataway, N.J.). The WGA coupled bead captures glycosylated, cellular membranes and glycoproteins and has been used for a wide variety of receptor sources and cultured cell membranes. The receptor is immobilized onto the WGA-SPA bead and a signal is generated on binding of an isotopically labeled ligand. Other coupling molecules which may be useful for receptor binding SPA assays include poly-L-lysine and WGA/polyethyleneimine (Amersham Biosciences; Piscataway, N.J.). See, for example, Berry, J. A., et al., (1991) Cardiovascular Pharmacol. 17 (Suppl.7): S143–S145; Hoffman, R., et al., (1992) Anal. Biochem. 203: 70–75; Kienhus, et al., (1992) J. Receptor Research 12: 389–399; Jing, S., et al., (1992) Neuron 9: 1067–1079.

The scintillant contained in SPA beads may include, for example, yttrium silicate (YSi), yttrium oxide (YOx), diphenyloxazole or polyvinyltoluene (PVT) which acts as a solid solvent for diphenylanthracine (DPA).

SPA assays may be used to analyze whether a sample contains an NPC1L1 antagonist or agonist. In these assays, a host cell which expresses NPC1L1 (e.g., SEQ ID NO: 2 or 4 or 12) on the cell surface or a membrane fraction thereof is incubated with and captured by SPA beads (e.g., WGA coated YOx beads or WGA coated YSi beads). The beads bearing the NPC1L1 are incubated with labeled, known ligand or agonist or antagonist (e.g., $^3$H-cholesterol, $^3$H-ezetimibe or $^{125}$I-ezetimibe). The assay mixture further includes either the sample to be tested or a blank (e.g., water). After an optional incubation, scintillation is measured using a scintillation counter. An NPC1L1 agonist or antagonist may be identified in the sample by measuring substantially reduced fluorescence, compared to what would be measured in the absence of such agonist or antagonist (blank). Measuring substantially reduced fluorescence may suggest that the sample contains a substance which competes for direct or indirect NPC1L1 binding with the known ligand, agonist or antagonist.

Alternatively, a sample may be identified as an antagonist or agonist of NPC1L1 by directly detecting binding in a SPA assay. In this assay, a labeled version of a candidate compound to be tested may be put in contact with the host cell expressing NPC1L1 or a membrane fraction thereof which is bound to the SPA bead. Fluorescence may then be assayed to detect the presence of a complex between the labeled candidate compound and the host cell or membrane fraction expressing NPC1L1 or a complex including NPC1L1. A candidate compound which binds directly or indirectly to NPC1L1 may possess NPC1L1 agonistic or antagonistic activity.

SPA Assays can also be performed along with a control experiment lacking any NPC1L1-dependent binding. The control experiment can be performed, for example, with a cell or cell membrane lacking any functional NPC1L1 (e.g., cell or cell membrane derived from a transgenic, mutant npc1l1$^-$ mouse as described herein). When the control experiment is performed, the level of binding observed in the presence of sample being tested for the presence of an antagonist can be compared with that observed in the control experiment.

Host cells expressing NPC1L1 may be prepared by transforming or transfecting a nucleic acid encoding an NPC1L1 of the invention into an appropriate host cell, whereby the receptor becomes incorporated into the membrane of the cell. A membrane fraction can then be isolated from the cell and used as a source of the receptor for assay. Alternatively, the whole cell expressing the receptor on the cell surface can be used in an assay. Preferably, specific binding of the labeled ligand or known antagonist or agonist to an untransfected/untransformed host cell or membrane fraction from an untransfected/untransformed host cell will be negligible. Preferred host cells include Chinese Hamster Ovary (CHO) cells, murine macrophage J774 cells or any other macrophage cell line and human intestinal epithelial Caco2 cells.

Sterol/5α-stanol Uptake Assay. Assays may also be performed to determine if a sample can agonize or antagonize NPC1L1 mediated sterol (e.g., cholesterol) or 5α-stanol uptake. In these assays, a host cell expressing NPC1L1 (e.g., SEQ ID NO: 2 or 4 or 12) on the cell surface (discussed above) can be contacted with detectably labeled sterol (e.g., $^3$H-cholesterol or $^{125}$I-cholesterol)) or 5α-stanol along with either a sample or a blank. After an optional incubation, the cells can be washed to remove unabsorbed sterol or 5α-stanol. Sterol or 5α-stanol uptake can be determined by detecting the presence of labeled sterol or 5α-stanol in the host cells. For example, assayed cells or lysates or fractions thereof (e.g., fractions resolved by thin-layer chromatography) can be contacted with a liquid scintillant and scintillation can be measured using a scintillation counter.

In these assays, an NPC1L1 antagonist in the sample may be identified by measuring substantially reduced uptake of labeled sterol (e.g., $^3$H-cholesterol) or 5α-stanol, compared to what would be measured in the absence of such an antagonist and an agonist may be identified by measuring substantially increased uptake of labeled sterol (e.g., $^3$H-cholesterol) or 5α-stanol, compared to what would be measured in the absence of such an agonist.

Uptake assays can also be performed along with a control experiment lacking any NPC1L1-dependent uptake. The control experiment can be performed, for example, with a cell lacking any functional NPC1L1 (e.g., cell derived from a transgenic, mutant npc1l1⁻ mouse as described herein). When the control experiment is performed, the level of uptake observed in the presence of sample being tested for the presence of an antagonist can be compared with that observed in the control experiment.

Mouse Assay. The present invention comprises a mutant, transgenic mouse which lacks any functional NPC1L1. This mouse may serve as a convenient control experiment in screening assays for identifying inhibitors of intestinal sterol (e.g., cholesterol) or 5α-stanol absorption, preferably inhibitors of NPC1L1. Preferably, a mouse assay of the present invention would comprise the following steps:

(a) feeding a sterol (e.g., cholesterol) or 5α-stanol-containing substance (e.g., comprising radiolabeled cholesterol, such as $^{14}$C-cholesterol or $^3$H-cholesterol) to a first and second mouse comprising a functional NPC1L1 gene and to a third, mutant mouse lacking a functional NPC1L1;

The sterol (e.g., cholesterol) or 5α-stanol containing substance preferably contains labeled cholesterol, such as a radiolabeled cholesterol, for example, $^3$H or $^{14}$C labeled cholesterol. The sterol (e.g., cholesterol) or 5α-stanol containing substance may also include cold, unlabeled sterol (e.g., cholesterol) or 5α-stanol such as in corn oil.

In these assays, the third npc1l1 mutant mouse serves as a (+)-control experiment which exhibits low levels of intestinal sterol (e.g., cholesterol) or 5α-stanol absorption and the second mouse serves as a (−)-control experiment which exhibits normal, uninhibited levels of intestinal sterol (e.g., cholesterol) or 5α-stanol absorption. The second mouse is not administered the sample to be tested for an NPC1L1 antagonist. The first mouse is the experiment.

(b) administering the sample to the first mouse comprising a functional NPC1L1 but not to the second mouse;

(c) measuring the amount of sterol (e.g., cholesterol) or 5α-stanol absorption in the intestine of said first, second and third mouse;

Intestinal sterol (e.g., cholesterol) or 5α-stanol absorption may be measured by any method known in the art. For example, the level intestinal absorption can be assayed by measuring the level of serum sterol (e.g., cholesterol) or 5α-stanol.

(d) comparing the levels of intestinal sterol (e.g., cholesterol) or 5α-stanol absorption in each mouse;

wherein the sample is determined to contain the intestinal sterol (e.g., cholesterol) or 5α-stanol absorption antagonist when the level of intestinal sterol (e.g., cholesterol) or 5α-stanol absorption in the first mouse and in the third mouse are less than the amount of intestinal sterol (e.g., cholesterol) or 5α-stanol absorption in the second mouse.

Preferably, if the sample contains an intestinal sterol (e.g., cholesterol) or 5α-stanol absorption inhibitor (e.g., an NPC1L1 inhibitor), the level of sterol (e.g., cholesterol) or 5α-stanol absorption in the first mouse will be similar to that of the third, npc1l1 mutant mouse.

An alternative, (+)-control experiment which may be used in these screening assays is a mouse comprising functional NPC1L1 which is administered a known antagonist of NPC1L1, such as ezetimibe.

Pharmaceutical Compositions

NPC1L1 agonists and antagonists discovered, for example, by the screening methods described above may be used therapeutically (e.g., in a pharmaceutical composition) to stimulate or block the activity of NPC1L1 and, thereby, to treat any medical condition caused or mediated by NPC1L1. In addition, the antibody molecules of the invention may also be used therapeutically (e.g., in a pharmaceutical composition) to bind NPC1L1 and, thereby, block the ability of NPC1L1 to bind a sterol (e.g., cholesterol) or 5α-stanol. Blocking the binding of a sterol (e.g., cholesterol) or 5α-stanol would prevent absorption of the molecule (e.g., by intestinal cells such as enterocytes). Blocking absorption of sterol (e.g., cholesterol) or 5α-stanol would be a useful way to lower serum sterol (e.g., cholesterol) or 5α-stanol levels in a subject and, thereby, reduce the incidence of, for example, hyperlipidemia, atherosclerosis, coronary heart disease, stroke or arteriosclerosis.

The term "subject" or "patient" includes any organism, preferably animals, more preferably mammals (e.g., mice, rats, rabbits, dogs, horses, primates, cats) and most preferably humans.

The term "pharmaceutical composition" refers to a composition including an active ingredient and a pharmaceutically acceptable carrier and/or adjuvant.

Although the compositions of this invention could be administered in simple solution, they are more typically used in combination with other materials such as carriers, preferably pharmaceutically acceptable carriers. Useful, pharmaceutically acceptable carriers can be any compatible, non-toxic substances suitable for delivering the compositions of the invention to a subject. Sterile water, alcohol, fats, waxes, and inert solids may be included in a pharmaceutically acceptable carrier. Pharmaceutically acceptable adjuvants (buffering agents, dispersing agents) may also be incorporated into the pharmaceutical composition.

Preferably, the pharmaceutical compositions of the invention are in the form of a pill or capsule. Methods for formulating pills and capsules are very well known in the art. For example, for oral administration in the form of tablets or capsules, the active drug component may be combined with any oral, non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

The pharmaceutical compositions of the invention may be administered in conjunction with a second pharmaceutical composition or substance. In preferred embodiments, the second composition includes a cholesterol-lowering drug. When a combination therapy is used, both compositions may be formulated into a single composition for simultaneous delivery or formulated separately into two or more compositions (e.g., a kit).

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Penn.; Avis et al. (eds.) (1993) *Pharmaceutical Dosage Forms: Parenteral Medications* Dekker, N.Y.; Lieberman et al. (eds.) (1990) *Pharmaceutical Dosage Forms: Tablets* Dekker, N.Y.; and Lieberman et al. (eds.) (1990), *Pharmaceutical Dosage Forms: Disperse Systems* Dekker, N.Y.

The dosage regimen involved in a therapeutic application may be determined by a physician, considering various factors which may modify the action of the therapeutic substance, e.g., the condition, body weight, sex and diet of the patient, the severity of any infection, time of administration, and other clinical factors. Often, treatment dosages are titrated upward from a low level to optimize safety and efficacy. Dosages may be adjusted to account for the smaller molecular sizes and possibly decreased half-lives (clearance times) following administration.

An "effective amount" of an antagonist of the invention may be an amount that will detectably reduce the level of intestinal sterol (e.g., cholesterol) or 5α-stanol absorption or detectably reduce the level of serum sterol (e.g., cholesterol) or 5α-stanol in a subject administered the composition.

Typical protocols for the therapeutic administration of such substances are well known in the art. Pharmaceutical composition of the invention may be administered, for example, by any parenteral or non-parenteral route.

Pills and capsules of the invention can be administered orally. Injectable compositions can be administered with medical devices known in the art; for example, by injection with a hypodermic needle.

Injectable pharmaceutical compositions of the invention may also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

Anti-Sense

The present invention also encompasses anti-sense oligonucleotides capable of specifically hybridizing to mRNA encoding NPC1L1 (e.g., any of SEQ ID NOs: 1, 3, 5–11 or 13) having an amino acid sequence defined by, for example, SEQ ID NO: 2 or 4 or 12 or a subsequence thereof so as to prevent translation of the mRNA. Additionally, this invention contemplates anti-sense oligonucleotides capable of specifically hybridizing to the genomic DNA molecule encoding NPC1L1, for example, having an amino acid sequence defined by SEQ ID NO: 2 or 4 or 12 or a subsequence thereof.

This invention further provides pharmaceutical compositions comprising (a) an amount of an oligonucleotide effective to reduce NPC1L1-mediated sterol (e.g., cholesterol) or 5α-stanol absorption by passing through a cell membrane and binding specifically with mRNA encoding NPC1L1 in the cell so as to prevent its translation and (b) a pharmaceutically acceptable carrier capable of passing through a cell membrane. In an embodiment, the oligonucleotide is coupled to a substance that inactivates mRNA. In another embodiment, the substance that inactivates mRNA is a ribozyme.

Reducing the level of NPC1L1 expression by introducing anti-sense NPC1L1 RNA into the cells of a patient is a useful method reducing intestinal sterol (e.g., cholesterol) or 5α-stanol absorption and serum cholesterol in the patient.

Kits

Kits of the present invention include ezetimibe, preferably combined with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. See for example, Gilman et al. (eds.) (1990), *The Pharmacological Bases of Therapeutics*, 8th Ed., Pergamon Press; and *Remington's Pharmaceutical Sciences*, supra, Easton, Penn.; Avis et al. (eds.) (1993) *Pharmaceutical Dosage Forms: Parenteral Medications* Dekker, N.Y.; Lieberman et al. (eds.) (1990) *Pharmaceutical Dosage Forms: Tablets* Dekker, N.Y.; and Lieberman et al. (eds.) (1990), *Pharmaceutical Dosage Forms: Disperse Systems* Dekker, N.Y. Preferably, the dosage form is a Zetia® tablet (Merck/Schering-Plough Corp.). Ezetimibe may be supplied in any convenient form. For example, tablets including ezetimibe may be supplied in bottles of 30, 90 or 500.

The kits of the present invention also include information, for example in the form of a package insert, indicating that the target of ezetimibe is NPC1L1 (NPC3). The term "target of ezetimibe" indicates that ezetimibe reduces intestinal sterol (e.g., cholesterol) or 5α-stanol absorption, either directly or indirectly, by antagonizing NPC1L1. The form of the insert may take any form, such as paper or on electronic media such as a magnetically recorded medium (e.g., floppy disk) or a CD-ROM.

The package insert may also include other information concerning the pharmaceutical compositions and dosage forms in the kit. Generally, such information aids patients and physicians in using the enclosed pharmaceutical compositions and dosage forms effectively and safely. For example, the following information regarding ezetimibe (e.g., Zetia®) and/or simvastatin (e.g., Zocor®) may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

The kits of the invention may also include simvastatin

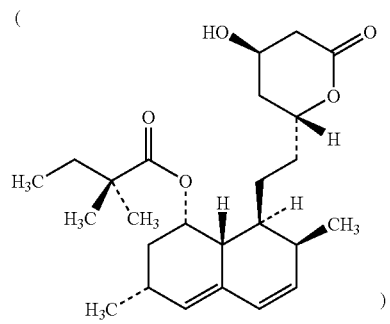

preferably combined with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. Preferably, the dosage form of simvastatin is a Zocor® tablet (Merck & Co.; Whitehouse Station, N.J.).

Tablets or pills comprising simvastatin may be supplied in any convenient form. For example, pills or tablets comprising 5 mg simvastatin can be supplied as follows: bottles of 30, 60, 90, 100 or 1000. Pills or tablets comprising 10 mg simvastatin may be supplied as follows: bottles of 30, 60, 90, 100, 1000 or 10,000. Pills or tablets comprising 20 mg simvastatin may be supplied as follows: bottles of 30, 60, 90, 100, 1000 or 10,000. Pills or tablets comprising 40 mg simvastatin may be supplied as follows: bottles of 30, 60, 90, 100 or 1000. Pills or tablets comprising 80 mg simvastatin may be supplied as follows: bottles of 30, 60, 90, 100, 1000 or 10,000.

Ezetimibe and simvastatin may be supplied, in the kit, as separate compositions or combined into a single composition. For example, ezetimibe and simvastatin may be supplied within a single, common pharmaceutical dosage form (e.g., pill or tablet) as in separate pharmaceutical dosage forms (e.g., two separate pills or tablets).

npc1l1⁻ Cells

The present invention provides any isolated mammalian cell, (e.g., an isolated mouse cell, an isolated rat cell or an isolated human cell) which lacks an NPC1L1 gene which encodes or can produce a functional NPC1L1 protein. Included within this embodiment are mutant npc1l1 genes comprising a point mutation, truncation or deletion of the genetic coding region or of any regulatory element (e.g., a promoter).

For example, the cell can be isolated from a mutant mouse comprising a homozygous mutation of endogenous, chromosomal NPC1L1 wherein the mouse does not produce any functional NPC1L1 protein (e.g., the mouse described below in Example 22). Moreover, the present invention comprises any cell, tissue, organ, fluid, nucleic acid, peptide or other biological substance derived or isolated from such a mutant mouse, particularly a mutant, transgenic mouse which does not produce any functional NPC1L1, wherein the region of endogenous, chromosomal NPC1L1 deleted, in the mouse, corresponds to nucleotides 790–998 of the nucleotide sequence set forth in SEQ ID NO: 45.

The isolated cell can be isolated or derived, for example, from the duodenum, gall bladder, liver, small intestine or stomach of the mutant mouse. Further, the cell can be an enterocyte.

The npc1l1⁻ mutant cells are useful, for example, for use in control experiments in screening assays (see e.g., supra) since they lack any NPC1L1-dependent uptake or binding of sterol, 5α-stanol or ezetimibe. The level of inhibition caused by a particular sample, in a screening assay, can be compared to that of an assay performed with the mutant cell. Ideally, though by no means necessarily, in a screening assay, for example, as described herein, the same amount of binding will be observed by a non-mutant cell or cell membrane, in the presence of an antagonist, as is observed in connection with a mutant npc1l1⁻ cell or cell membrane alone.

EXAMPLES

The following examples are provided to more clearly describe the present invention and should not be construed to limit the scope of the invention in any way.

Example 1

Cloning and Expression of Rat, Mouse and Human NPC1L1.

Rat NPC, mouse NPC1L1 or human NPC1L1 can all conveniently be amplified using polymerase chain reaction (PCR). In this approach, DNA from a rat, mouse or human cDNA library can be amplified using appropriate primers and standard PCR conditions. Design of primers and optimal amplification conditions constitute standard techniques which are commonly known in the art.

An amplified NPC1L1 gene may conveniently be expressed, again, using methods which are commonly known in the art. For example, NPC1L1 may be inserted into a pET-based plasmid vector (Stratagene; La Joola, Calif.), downstream of the T7 RNA polymerase promoter. The plasmid may then be transformed into a T7 expression system (e.g., BL21DE3 $E.coli$ cells), grown in a liquid culture and induced (e.g., by adding IPTG to the bacterial culture).

Example 2

Direct Binding Assay.

Membrane preparation: Caco2 cells transfected with an expression vector containing a polynucleotide encoding NPC1L1 (e.g., SEQ ID NO: 2, 4 or 12) are harvested by incubating in 5 mM EDTA/phosphate-buffered saline followed by repeated pipeting. The cells are centrifuged 5 min at 1000×g. The EDTA/PBS is decanted and an equal volume of ice-cold 50 mM Tris-HCl, pH 7.5 is added and cells are broken up with a Polytron (PT10 tip, setting 5, 30 sec). Nuclei and unbroken cells are sedimented at 1000×g for 10 min and then the supernatant is centrifuged at 50,000×g for 10 min. The supernatant is decanted, the pellet is resuspended by Polytron, a sample is taken for protein assay (bicinchoninic acid, Pierce), and the tissue is again centrifuiged at 50,000×g. Pellets are stored frozen at −20° C.

Binding assay: For saturation binding, four concentrations of [$^3$H]-ezetimibe (15 Ci/mmol) are incubated without and with $10^{-5}$ M ezetimibe in triplicate with 50 µg of membrane protein in a total volume of 200 µl of 50 mM Tris-HCl, pH 7.5, for 30 min at 30° C. Samples are filtered on GF/B filters and washed three times with 2 ml of cold Tris buffer. Filters are dried in a microwave oven, impregnated with Meltilex wax scintillant, and counted at 45% efficiency. For competition binding assays, five concentrations of a sample are incubated in triplicate with 18 nM [$^3$H]-ezetimibe and 70 µg of membrane protein under the conditions described above. Curves are fit to the data with Prism (GraphPad Software) nonlinear least-squares curve-fitting program and $K_i$ values are derived from $IC_{50}$ values according to Cheng and Prusoff (Cheng, Y. C., et al., (1973) Biochem. Pharmacol. 22:3099–3108).

Example 3

SPA Assay.

For each well of a 96 well plate, a reaction mixture of 10 µg human, mouse or rat NPC1L1-CHO overexpressing membranes (Biosignal) and 200 µg/well YSi-WGA-SPA beads (Amersham) in 100 µl is prepared in NPC1L1 assay buffer (25 mM HEPES, pH 7.8, 2 mM $CaCl_2$, 1 mM $MgCl_2$, 125 mM NaCl, 0.1% BSA). A 0.4 nM stock of ligand-[$^{125}$I]- ezetimibe- is prepared in the NPC1L1 assay buffer. The above solutions are added to a 96-well assay plate as follows: 50 μl NPC1L1 assay buffer, 100 μl of reaction mixture, 50 μl of ligand stock (final ligand concentration is 0.1 nM). The assay plates are shaken for 5 minutes on a plate shaker, then incubated for 8 hours before cpm/well are determined in Microbeta Trilux counter (PerkinElmer).

These assays will indicate that [$^{125}$I]-ezetimibe binds to the cell membranes expressing human, mouse or rat NPC1L1. Similar results will be obtained if the same experiment is performed with radiolabeled cholesterol (e.g., $^{125}$I-cholesterol).

Example 4

Cholesterol Uptake Assay.

CHO cells expressing either SR-B1 or three different clones of rat NPC1L1 or one clone of mouse NPC1L1 were starved overnight in cholesterol free media then dosed with [$^3$H]-cholesterol in a mixed synthetic micelle emulsion for 4 min, 8 min, 12 min or 24 min in the absence or presence of 10 μM ezetimibe. The cells were harvested and the lipids were organically extracted. The extracted lipids were spotted on thin-layer chromatography (TLC) plates and resolved within an organic vapor phase. The free cholesterol bands for each assay were isolated and counted in a scintillation counter.

The SR-B1 expressing cells exhibited an increase in [$^3$H]-cholesterol uptake as early as 4 min which was also inhibited by ezetimibe. The three rat clones and the one mouse clone appeared to give background levels of [$^3$H]-cholesterol uptake which was similar to that of the untransformed CHO cell.

These experiments will yield data demonstrating that CHO cells can perform mouse, rat and human NPC1L1-dependent uptake of [$^3$H]-cholesterol when more optimal experimental conditions are developed.

Example 5

Expression of Rat NPC1L1 in Wistar Rat Tissue.

In these experiments, the expression of rat NPC1L1 mRNA, in several rat tissues, was evaluated. The tissues evaluated were esophagus, stomach, duodenum, jejunum, ileum, proximal colon, distal colon, liver, pancreas, heart, aorta, spleen, lung, kidney, brain, muscle, testes, ovary, uterus, adrenal gland and thyroid gland. Total RNA samples were isolated from at least 3 male and 3 female animals and pooled. The samples were then subjected to real time quantitative PCR using Taqman analysis using standard dual-labeled fluorogenic oligonucleotide probes. Typical probe design incorporated a 5' reporter dye (e.g., 6FAM (6-carboxyfluorescein) or VIC) and a 3' quenching dye (e.g., TAMRA (6-carboxytetramethyl-rhodamine)).

rat NPC1L1:

Forward:
TCTTCACCCTTGCTCTTTGC                        (SEQ ID NO: 14)

Reverse:
AATGATGGAGAGTAGGTTGAGGAT                    (SEQ ID NO: 15)

Probe:
[6FAM]TGCCCACCTTTGTTGTCTGCTACC              (SEQ ID NO: 16)

[TAMRA]

rat β-actin:

Forward:
ATCGCTGACAGGATGCAGAAG                       (SEQ ID NO: 17)

Reverse:
TCAGGAGGAGCAATGATCTTGA                      (SEQ ID NO: 18)

Probe:
[VIC]AGATTACTGCCCTGGCTCCTAGCACCAT           (SEQ ID NO: 19)

[TAMRA]

PCR reactions were run in 96-well format with 25 μl reaction mixture in each well containing: Platinum Super-Mix (12.5 μl), ROX Reference Dye (0.5 μl), 50 mM magnesium chloride (2 μl), cDNA from RT reaction (0.2 μl). Multiplex reactions contained gene specific primers at 200 nM each and FAM labeled probe at 100 nM and gene specific primers at 100 nM each and VIC labeled probe at 50 nM. Reactions were run with a standard 2-step cycling program, 95° C. for 15 sec and 60° C. for 1 min, for 40 cycles.

The highest levels of expression were observed in the duodenum, jejunum and ileum tissue. These data indicate that NPC1L1 plays a role in cholesterol absorption in the intestine.

Example 6

Expression of Mouse NPC1L1 in Mouse Tissue.

In these experiments, the expression of mouse NPC1L1 mRNA, in several tissues, was evaluated. The tissues evaluated were adrenal gland, BM, brain, heart, islets of langerhans, LI, small intestine, kidney, liver, lung, MLN, PLN, muscle, ovary, pituitary gland, placenta, Peyers Patch, skin, spleen, stomach, testes, thymus, thyroid gland, uterus and trachea. Total RNA samples were isolate from at least 3 male and 3 female animals and pooled. The samples were then subjected to real time quantitative PCR using Taqman analysis using the following primers and probes:

mouse NPC1L1:

Forward:
ATCCTCATCCTGGGCTTTGC                        (SEQ ID NO: 20)

Reverse:
GCAAGGTGATCAGGAGGTTGA                       (SEQ ID NO: 21)

Probe:
[6FAM]CCCAGCTTATCCAGATTTTCTTCTTCCG          (SEQ ID NO: 22)

C[TAMRA]

The highest levels of expression were observed in the Peyer's Patch, small intestine, gall bladder and stomach tissue. These data are consistent with a cholesterol absorption role for NPC1L1 which takes place in the digestive system.

Example 7

Expression of Human NPC1L1 in Human Tissue.

In these experiments, the expression level of human NPC1L1 mRNA was evaluated in 2045 samples representing 46 normal tissues. Microarray-based gene expression analysis was performed on the Affymetrix HG-U95 GeneChip using a cRNA probe corresponding to base pairs 4192–5117 (SEQ ID NO: 43) in strict accordance to Affymetrix's established protocols. Gene Chips were scanned under low photo multiplier tube (PMT), and data were normalized using either Affymetrix MAS 4.0 or MAS 5.0 algorithms. In addition "spike ins" for most samples were used to construct a standard curve and obtain RNA concentration values according Gene Logic algorithms and procedures. A summary of these results are indicated, below, in Table 2.

TABLE 2

Expression level of NPC1L1 mRNA in various human tissues.

| Tissue | Present | Absent | Lower 25% | Median | Upper 75% |
| --- | --- | --- | --- | --- | --- |
| Adipose | 2 of 32 | 30 of 32 | −2.45 | 1.16 | 12.23 |
| Adrenal Gland | 0 of 12 | 12 of 12 | −23.54 | −4.47 | 10.51 |
| Appendix | 0 of 3 | 3 of 3 | −8.02 | −6.69 | 38.19 |
| Artery | 0 of 3 | 3 of 3 | −6.59 | −4.67 | 9.68 |
| Bladder | 1 of 5 | 4 of 5 | −22 | −7.95 | −1.99 |
| Bone | 0 of 3 | 3 of 3 | −1.64 | 3.3 | 19.53 |
| Breast | 4 of 80 | 76 of 80 | −4.07 | 3.13 | 14.67 |
| Cerebellum | 0 of 5 | 5 of 5 | −3.04 | 3.24 | 15.38 |
| Cervix | 3 of 101 | 98 of 101 | −7.56 | −0.07 | 20.89 |
| Colon | 9 of 151 | 142 of 151 | −10.19 | 0.31 | 18.36 |
| Cortex Frontal Lobe | 0 of 7 | 7 of 7 | 1.4 | 8.46 | 11.75 |
| Cortex Temporal Lobe | 0 of 3 | 3 of 3 | 7.1 | 8.5 | 15.87 |
| Duodenum | 59 of 61 | 2 of 61 | 519.23 | 827.43 | 1101.67 |
| Endometrium | 0 of 21 | 21 of 21 | −14.43 | −6.39 | 2.79 |
| Esophagus | 1 of 27 | 26 of 27 | −10.93 | −4.97 | 12.48 |
| Fallopion Tube | 3 of 51 | 48 of 51 | 5.02 | 13.24 | 26.77 |
| Gall Bladder | 8 of 8 | 0 of 8 | 205.76 | 273.39 | 422.8 |
| Heart | 0 of 3 | 3 of 3 | 3.33 | 11.19 | 11.66 |
| Hippocampus | 0 of 5 | 5 of 5 | 8.25 | 9.11 | 19.83 |
| Kidney | 4 of 86 | 82 of 86 | −8.36 | 3.41 | 16.46 |
| Larynx | 0 of 4 | 4 of 4 | −13.76 | −0.81 | 8.54 |
| Left Atrium | 2 of 141 | 139 of 141 | −18.9 | −4.58 | 6.84 |
| Left Ventricle | 0 of 15 | 15 of 15 | −21.19 | −9.59 | 17.7 |
| Liver | 32 of 34 | 2 of 34 | 325.74 | 427.77 | 540.1 |
| Lung | 2 of 93 | 91 of 93 | −3.47 | 11.03 | 22.34 |
| Lymph Node | 0 of 11 | 11 of 11 | −1.78 | −0.19 | 1.34 |
| Muscles | 0 of 39 | 39 of 39 | −21.57 | 8.25 | 26.73 |
| Myometrium | 8 of 106 | 98 of 106 | −3.95 | 4.87 | 17.55 |
| Omentum | 0 of 15 | 15 of 15 | −14.25 | −1.6 | 19.58 |
| Ovary | 1 of 74 | 73 of 74 | 0.5 | 17.51 | 38.28 |
| Pancreas | 0 of 34 | 34 of 34 | −87.08 | −53.2 | −24.14 |
| Placenta | 0 of 5 | 5 of 5 | −20.4 | −3.44 | 18.91 |
| Prostate | 0 of 32 | 32 of 32 | 1.08 | 15.56 | 27.24 |

TABLE 2-continued

Expression level of NPC1L1 mRNA in various human tissues.

| Tissue | Present | Absent | Lower 25% | Median | Upper 75% |
|---|---|---|---|---|---|
| Rectum | 1 of 43 | 42 of 43 | -9.26 | -1.49 | 9.8 |
| Right Atrium | 4 of 169 | 165 of 169 | -19.32 | -6.58 | 7.72 |
| Right Ventricle | 1 of 160 | 159 of 160 | -24.01 | -6.49 | 10.06 |
| Skin | 0 of 59 | 59 of 59 | -12.68 | 1.5 | 22.77 |
| Small Intestine | 46 of 68 | 22 of 68 | 21.21 | 493.93 | 939.2 |
| Soft Tissues | 1 of 6 | 5 of 6 | -1.99 | 2.6 | 5.32 |
| Spleen | 0 of 31 | 31 of 31 | -9.41 | -0.31 | 9.5 |
| Stomach | 7 of 47 | 40 of 47 | 19.02 | 52.29 | 117.09 |
| Testis | 0 of 5 | 5 of 5 | -4.51 | 1.22 | 11.2 |
| Thymus | 1 of 71 | 70 of 71 | -6.26 | 2.51 | 11.67 |
| Thyroid Gland | 1 of 18 | 17 of 18 | -12.22 | 2.84 | 17.86 |
| Uterus | 0 of 58 | 58 of 58 | -10.67 | 1.59 | 16.01 |
| WBC | 3 of 40 | 37 of 40 | -16.45 | -0.72 | 25.18 |

Shaded data corresponds to tissues wherein the highest levels of NPC1L1 mRNA was detected. The "Present" column indicates the proportion of specified tissue samples evaluated wherein NPC1L1 mRNA was detected. The "Absent" column indicates the proportion of specified tissue samples evaluated wherein NPC1L1 RNA was not detected. The "lower 25%", "median" and "upper 75%" columns indicate statistical distribution of the relative NPC1L1 signal intensities observed for each set of tissue evaluated.

Example 8

Distribution of Rat NPC1L1, Rat IBAT or Rat SR-B1 mRNA in Rat Small Intestine.

In these experiments, the distribution of rat NPC1L1 mRNA along the proximal-distal axis of rat small intestines was evaluated. Intestines were isolated from five independent animals and divided into 10 sections of approximately equal length. Total RNA was isolated and analyzed, by real time quantitative PCR using Taqman analysis, for localized expression levels of rat NPC1L1, rat IBAT (ileal bile acid transporter) or rat SR-B1 mRNA. The primers and probes used in the analysis were:

rat NPC1L1:

Forward:
TCTTCACCCTTGCTCTTTGC          (SEQ ID NO: 23)

Reverse:
AATGATGGAGAGTAGGTTGAGGAT      (SEQ ID NO: 24)

Probe:
[6FAM]TGCCCACCTTTGTTGTCTGCTACC (SEQ ID NO: 25)

[TAMRA]

rat Villin:

Forward:
AGCACCTGTCCACTGAAGATTTC       (SEQ ID NO: 26)

Reverse:
TGGACGCTGAGCTTCAGTTCT         (SEQ ID NO: 27)

Probe:
[VIC]CTTCTCTGCGCTGCCTCGATGGAA (SEQ ID NO: 28)

[TAMRA]

rat SR-B1:

Forward:
AGTAAAAAGGGCTCGCAGGAT         (SEQ ID NO: 29)

Reverse:
GGCAGCTGGTGACATCAGAGA         (SEQ ID NO: 30)

Probe:
[6FAM]AGGAGGCCATGCAGGCCTACTCTGA (SEQ ID NO: 31)
[TAMRA]

rat IBAT:

Forward:
GAGTCCACGGTCAGTCCATGT         (SEQ ID NO: 32)

Reverse:
TTATGAACAACAATGCCAAGCAA       (SEQ ID NO: 33)

Probe:
[6FAM]AGTCCTTAGGTAGTGGCTTAGTCCC (SEQ ID NO: 34)

TGGAAGCTC[TAMRA]

The MRNA expression levels of each animal intestinal section were analyzed separately, then the observed expression level was normalized to the observed level of villin mRNA in that intestinal section. The observed, normalized mRNA expression levels for each section where then averaged.

The expression level of NPC1L1 and SR-B1 were highest in the jejunum (sections 2–5) as compared to that of the more distal ileum sections. Since the jejunum is believed to be the site of cholesterol absorption, these data suggest such a role for rat NPC1L1. IBAT distribution favoring the ileum is well document and served as a control for the experiment.

Example 9

In situ Analysis of Rat NPC1L1 mRNA in Rat Jejunum Tissue.

The localization of rat NPC1L1 mRNA was characterized by in situ hybridization analysis of rat jejunum serial sections. The probes used in this analysis were:

```
T7-sense probe:
GTAATACGACTCACTATAGGGCCCTGACGGTCCT (SEQ ID NO: 35)

TCCTGAGGGAATCTTCAC

T7-antisense probe:
GTAATACGACTCACTATAGGGCCTGGGAAGTTGG (SEQ ID NO: 36)

TCATGGCCACTCCAGC
```

The RNA probes were synthesized using T7 RNA polymerase amplification of a PCR amplified DNA fragment corresponding rat NPC1L1 nucleotides 3318 to 3672 (SEQ ID NO: 1). Sense and anti-sense digoxigenin-UTP labeled cRNA probes were generated from the T7 promoter using the DIG RNA Labeling Kit following the manufacturer's instructions. Serial cryosections rat jejunum were hybridized with the sense and antiisense probes. Digoxigenin labeling was detected with the DIG Nucleic Acid Detection Kit based on previous methods. A positive signal is characterized by the deposition of a red reaction product at the site of hybridization.

The anti-sense probe showed strong staining of epithelium along the crypt-villus axis under low magnification (40×). The observed rat NPC1L1 mRNA expression levels may have been somewhat greater in the crypts than in the villus tips. Under high magnification (200×), staining was observed in the enterocytes but not in the goblet cells. A lack of staining observed with the sense probe (control) confirmed the high specificity of the NPC1L1 anti-sense signal. These data provided further evidence of the role of rat NPC1L1 in intestinal cholesterol absorption.

Example 10

FACS (Fluorescence Activated Cell Sorting) Analysis of Fluorescently Labeled Ezetimibe Binding to Transiently Transfected CHO Cells.

In these experiments, the ability of BODIPY-labeled ezetimibe (Altmann, et al., (2002) Biochim. Biophys. Acta 1580(1):77–93) to bind to NPC1L1 and SR-B1 was evaluated. "BODIPY" is a fluorescent group which was used to detect the BODIPY-ezetimibe. Chinese hamster ovary (CHO) cells were transiently transfected with rat NPC1L1 DNA (rNPC1L1/CHO), mouse NPC1L1 DNA (mNPC1L1/CHO), mouse SR-B1 DNA (mSRBI/CHO) or EGFP DNA (EGFP/CHO). EGFP is enhanced green fluorescent protein which was used as a positive control. The transfected CHO cells or untransfected CHO cells were then stained with 100 nM BODIPY-labeled ezetimibe and analyzed by FACS. Control experiments were also performed wherein the cells were not labeled with the BODIPY-ezetimibe and wherein untransfected CHO cells were labeled with the BODIPY-ezetimibe.

No staining was observed in the untransfected CHO, rNPC1L1/CHO or mNPC1L1/CHO cells. Fluorescence was detected in the positive-control EGFP/CHO cells. Staining was also detected in the mouse SR-B1/CHO cells. These data show that, under the conditions tested, BODIPY-ezetimibe is capable of binding to SR-B1 and that such binding is not ablated by the presence of the fluorescent BODIPY group. When more optimal conditions are determined, BODIPY-ezetimibe will be shown to label the rNPC1L1/CHO and mNPC1L1/CHO cells.

Example 11

FACS Analysis of Transiently Transfected CHO Cells Labeled with Anti-FLAG Antibody M2.

In these experiments, the expression of FLAG-tagged NPC1L1 on CHO cells was evaluated. CHO cells were transiently transfected with mouse NPC1L1 DNA, rat NPC1L1 DNA, FLAG- rat NPC1L1 DNA or FLAG- mouse NPC1L1 DNA. The 8 amino acid FLAG tag used was DYKDDDDK (SEQ ID NO: 37) which was inserted on the amino-terminal extracellular loop just past the secretion signal sequence. The cells were incubated with commercially available anti-FLAG monoclonal mouse antibody M2 followed by a BODIPY-tagged anti-mouse secondary antibody. The treated cells were then analyzed by FACS.

The M2 antibody stained the CHO cells transfected with FLAG-rat NPC1L1 DNA and with FLAG-mouse NPC1L1. No staining was observed in the CHO cells transfected with mouse NPC1L1 DNA and with rat NPC1L1 DNA. These data showed that rat NPC1L1 and mouse NPC1L1 possess no significant, inherent fluorescence and are not bound by the anti-FLAG antibody. The observed, FLAG-dependent labeling of the cells indicated that the FLAG-mouse NPC1L1 and FLAG-rat NPC1L1 proteins are localized at the cell membrane of the CHO cells.

Example 12

FACS Analysis of FLAG-rat NPC1L1-EGFP Chimera in Transiently Transfected CHO Cells.

In these experiments, the surface and cytoplasmic localization of rat NPC1L1 in CHO cells was evaluated. CHO cells were transiently transfected with FLAG- rat NPC1L1 DNA or with FLAG-rat NPC1L1-EGFP DNA. In these fusions, the FLAG tag is at amino-terminus of rat NPC1L1 and EGFP fusion is at the carboxy-terminus of rat NPC1L1. The cells were then stained with the M2 anti-FLAG mouse (primary) antibody followed by secondary staining with a BODIPY-labeled anti-mouse antibody. In control experiments, cells were stained with only the secondary antibody and not with the primary antibody (M2). The stained cells were then analyzed by FACS.

In a control experiment, FLAG-rat NPC1L1 transfected cells were stained with BODIPY anti-mouse secondary antibody but not with the primary antibody. The data demonstrated that the secondary, anti-mouse antibody possessed no significant specificity for FLAG-rat NPC1L1 and that the FLAG-rat NPC1L1, itself, possesses no significant fluorescence.

In another control experiment, unlabeled FLAG-rat NPC1L1-EGFP cells were FACS analyzed. In these experiments, autofluorescence of the enhanced green fluorescent protein (EGFP) was detected.

FLAG-rat NPC1L1 cells were stained with anti-FLAG mouse antibody M2 and with the BODIPY-labeled anti-mouse secondary antibody and FACS analyzed. The data from this analysis showed that the cells were labeled with the secondary, BODIPY-labeled antibody which indicated expression of the FLAG-rat NPC1L1 protein on the surface of the CHO cells.

FLAG-rat NPC1L1-EGFP cells were stained with anti-FLAG mouse antibody M2 and with the BODIPY-labeled anti-mouse secondary antibody and FACS analyzed. The data from this analysis showed that both markers (BODIPY and EGFP) were present indicating surface expression of the chimeric protein. The data also indicated that a portion of the protein was located within the cells and may be associated with transport vesicles. These data supported a role for rat NPC1L1 in vesicular transport of cholesterol or protein expressed in subcellular organelles such as the rough endoplasmic reticulum.

Example 13

FACS Analysis and Fluorescent Microscopy of FLAG-rat NPC1L1-EGFP Chimera in a Cloned CHO Cell Line.

In these experiments, the cellular localization of rat NPC1L1 was evaluated by FACS analysis and by immunohistochemistry. CHO cells were transfected with FLAG-rat NPC1L1-EGFP DNA and stained with anti-FLAG mouse antibody M2 and then with a BODIPY-labeled anti-mouse secondary antibody. In the fusion, the FLAG tag is at the amino-terminus of rat NPC1L1 and the enhanced green fluorescent protein (EGFP) tag is located at the carboxy-terminus of the rat NPC1L1. The stained cells were then analyzed by FACS and by fluorescence microscopy.

Cells transfected with FLAG-rat NPC1L1-EGFP DNA were stained with the anti-FLAG mouse antibody M2 and then with the BODIPY-labeled anti-mouse secondary antibody. FACS analysis of the cells detected both markers indicating surface expression of the chimeric protein.

FLAG-rat NPC1L1-EGFP transfected cells were analyzed by fluorescent microscopy at 63× magnification. Fluorescent microscopic analysis of the cells indicated non-nuclear staining with significant perinuclear organelle staining. Resolution of the image could not confirm the presence of vesicular associated protein. These data indicated that the fuision protein was expressed on the cell membrane of CHO cells.

Example 14

Generation of Polyclonal Anti-rat NPC1L1 Rabbit Antibodies.

Synthetic peptides (SEQ ID NOs: 39–42) containing an amino- or carboxy-terminal cysteine residue were coupled to keyhole limpet hemocyanin (KLH) carrier protein through a disulfide linkage and used as antigen to raise polyclonal antiserum in New Zealand white rabbits (range 3–9 months in age). The KLH-peptide was emulsified by mixing with an equal volume of Freund's Adjuvant, and injected into three subcutaneous dorsal sites. Prior to the 16 week immunization schedule a pre-immune sera sample was collected which was followed by a primary injection of 0.25 mg KLH-peptide and 3 scheduled booster injections of 0.1 mg KLH-peptide. Animals were bled from the auricular artery and the blood was allowed to clot and the serum was then collected by centrifugation.

The anti-peptide antibody titer was determined with an enzyme linked immunosorbent assay (ELISA) with free peptide bound in solid phase (1 µg/well). Results are expressed as the reciprocal of the serum dilution that resulted in an $OD_{450}$ of 0.2. Detection was obtained using the biotinylated anti-rabbit IgG, horse radish peroxidase-streptavidin (HRP-SA) conjugate, and ABTS.

Example 15

FACS Analysis of Rat NPC1L1 Expression in CHO Cells Transiently Transfected with Rat NPC1L1 DNA Using Rabbit Anti-rat NPC1L1 Antisera.

In these experiments, the expression of rat NPC1L1 on the surface of CHO cells was evaluated. CHO cells were transfected with rat NPC1L1 DNA, then incubated with either rabbit preimmune serum or with 10 week anti-rat NPC1L1 serum described, above, in Example 14 (i.e., A0715, A0716, A0867 or A0868). Cells labeled with primary antisera were then stained with a BODIPY-modified anti-rabbit secondary antibody followed by FACS analysis.

No antibody surface labeling was observed for any of the pre-immune sera samples. Specific cell surface labeling of rat NPC1L1 transfected cells was observed for both A0715 and A0868. Antisera A0716 and A0867 did not recognize rat NPC1L1 surface expression in this assay format. This indicates that the native, unfused rat NPC1L1 protein is expressed in the CHO cells and localized to the CHO cell membranes. Cell surface expression of NPC1L1 is consistent with a role in intestinal cholesterol absorption.

Example 16

FACS Analysis of CHO Cells Transiently Transfected with FLAG-Mouse NPC1L1 DNA or FLAG-rat NPC1L1 DNA or Untransfected CHO Cells Using Rabbit Anti-rat NPC1L1 Antisera.

In these experiments, the expression of FLAG-mouse NPC1L1 and FLAG-rat NPC1L1 in CHO cells was evaluated. CHO cells were transiently transfected with FLAG-mouse NPC1L1 DNA or with FLAG-rat NPC1L1 DNA. The FLAG-mouse NPC1L1 and FLAG-rat NPC1L1 transfected cells were labeled with either A0801, A0802, A0715 or A0868 sera (see Example 14) or with anti-FLAG antibody, M2. The labeled cells were then stained with BODIPY-labeled anti-rabbit secondary antibody and FACS analyzed. The untransfected CHO cells were analyzed in the same manner as the transfected cell lines.

Positive staining of the untransfected CHO cells was not observed for any of the antisera tested. Serum A0801-dependent labeling of FLAG-rat NPC1L1 transfected cells was observed but such labeling of FLAG-mouse NPC1L1 transfected cells was not observed. Serum A0802-dependent labeling of FLAG-mouse NPC1L1 or FLAG-rat NPC1L1 transfected cells was not observed. Strong serum A0715-dependent labeling of FLAG-rat NPC1L1 transfected cells was observed and weak serum A0715-dependent labeling of FLAG-mouse NPC1L1 transfected cells was observed. Weak serum A0868-dependent labeling of rat NPC1L1 and mouse NPC1L1 transfected cells was observed. Strong Anti-FLAG M2 antibody-dependent labeling of FLAG-rat NPC1L1 and FLAG-mouse NPC1L1 transfected cells was observed. The strong M2 staining is likely to be due to the fact that M2 is an affinity-purified, monoclonal antibody of known concentration. In contrast, the respective antisera are polyclonal, unpurified and contain an uncertain concentration of anti-rat NPC1L1 antibody. These date provide further evidence that the FLAG-mouse NPC1L1 and FLAG-rat NPC1L1 proteins are expressed in CHO cells and localized to the CHO cell membranes. Cell surface expression of NPC1L1 is consistent with a role in intestinal cholesterol absorption.

Example 17

Immunohistochemical Analysis of Rat Jejunum Tissue with Rabbit Anti-rat NPC1L1 Antisera A0715.

In these experiments, the localization of rat NPC1L1 in rat jejunum was analyzed by immunohistochemistry. Rat jejunum was removed, immediately embedded in O.C.T. compound and frozen in liquid nitrogen. Sections (6 μm) were cut with a cryostat microtome and mounted on glass slides. Sections were air dried at room temperature and then fixed in Boumn's fixative. Streptavidin-biotin-peroxidase immunostaining was carried out using Histostain-SP kit. Endogenous tissue peroxidase activity was blocked with a 10 minute incubation in 3% $H_2O_2$ in methanol, and nonspecific antibody binding was minimized by a 45 minute incubation in 10% nonimmune rabbit serum. Sections were incubated with a rabbit anti-rat NPC1L1 antisera A0715 or A0868 at a 1:500 dilution at 4° C., followed by incubation with biotinylated goat anti-rabbit IgG and with streptavidin-peroxidase. Subsequently, the sections were developed in an aminoethyl carbazole (AEC)-$H_2O_2$ staining system and counterstained with hematoxylin and examined by microscopy. A positive reaction using this protocol is characterized by the deposition of a red reaction product at the site of the antigen-antibody reaction. Nuclei appeared blue from the hematoxylin counterstain. Controls were performed simultaneously on the neighboring sections from the same tissue block. Control procedures consisted of the following: (1) substitute the primary antibody with the pre-immune serum, (2) substitute the primary antibody with the non-immune rabbit serum, (3) substitute the primary antibody with PBS, (4) substitute the second antibody with PBS.

The example shows tissue stained with anti-rat NPC1L1 sera A0715 or with the preimmune sera analyzed at low magnification (40×) and at high magnification (200×). The A0715-stained tissue, at low magnification, showed positive, strong staining of the villi epithelial layer (enterocytes). The A0715-stained tissue at high magnification showed positive, strong staining of the enterocyte apical membranes. No staining was observed in tissue treated only with pre-immune sera. Similar results were obtained with sera A0868. These data indicate that rat NPC1L1 is expressed in rat jejunum which is consistent with a role in intestinal cholesterol absorption.

Example 18

Labeled Cholesterol Uptake Assay.

In this example, the ability of CHO cells stably transfected with rat NPC1L1 to take up labeled cholesterol was evaluated. In these assays, cholesterol uptake, at a single concentration, was evaluated in a pulse-chase experiment. The data generated in these experiments are set forth, below, in Table 3.

Cells:

A. CHO cells stably transfected with rat NPC1L1 cDNA
B. CHO background (no transfection)

Cells were seeded at 500,000 cells/ well (mL) in 12-well plates.

Procedure:

All reagents and culture plates were maintained at 37° C. unless otherwise noted.

Starve. The maintenance media (F12 HAMS, 1% Pen/Strep, 10% FCS (fetal calf serum)) was removed and the cells were rinsed with serum-free HAMS media. The serum-free media was then replaced with 1 mL "starve" media (F12 HAMS, Pen/Strep, 5% lipoprotein deficient serum (LPDS).

One plate of each cell line was starved overnight. The remaining 2 plates were designated "No Starve" (see below).

Pre-Incubation. Media was removed from all plates, rinsed with serum-free HAMS and replaced with starve media for 30 minutes.

$^3$H-Cholesterol Pulse. The following was added directly to each well.

0.5 μCi $^3$H-cholesterol (~$1.1 \times 10^6$ dpm/well) in 50 μl of a mixed bile salt micelle.

4.8 mM sodium taurocholate (2.581 mg/mL)

0.6 mM sodium oleate (0.183 mg/mL)

0.25 mM cholesterol (0.1 mg/mL)

Dispersed in "starve" media by ultrasonic vibration

Final media cholesterol concentration=5 μg/mL

Labeled cholesterol pulse time points were 0, 4, 12 and 24 minutes. Triplicate wells for each treatment were prepared.

Wash. At the designated times, media was aspirated and the cells were washed once with Hobbs Buffer A (50 mM Tris, 0.9% NaCl, 0.2% BSA, pH 7.4) and once with Hobbs Buffer B (50 mM Tris, 0.9% NaCl, pH 7.4 (no BSA)) at 37° C.

Processing/Analysis. Cells were digested overnight with 0.2N NaOH, 2 mL/well at room temperature. One 1.5 mL aliquot was removed from each well, neutralized & counted for radioactivity by scintillation counting. Two additional 50 μl aliquots from all wells are assayed for total protein by the Pierce micro BCA method. The quantity of labeled cholesterol observed in the cells was normalized by the quantity of protein in the cells.

TABLE 3

Uptake of ³H-cholesterol by CHO cells transfected with rat NPC1L1 or mouse SR-B1 or untransfected CHO cells.

| Time, min After ³H-Cholesterol | Total Cholesterol, dpm protein ± sem | | | | Total Cholesterol, dpm/mg protein ± sem | | | |
|---|---|---|---|---|---|---|---|---|
| | NPC1L1 | | CHO | | NPC1L1 | | CHO | |
| No Starve | | | | | | | | |
| 0 | 2067 | ±46 | 4568 | ±1937 | 10754 | ±166 | 22881 | ±9230 |
| 4 | 2619 | ±130 | 2868 | ±193 | 15366 | ±938 | 15636 | ±1471 |
| 12 | 2868 | ±193 | 4459 | ±170 | 15636 | ±1471 | 24622 | ±966 |
| 24 | 7010 | ±89 | 7204 | ±173 | 41129 | ±685 | 39361 | ±1207 |
| Starve | | | | | | | | |
| 0 | 1937 | ±273 | 2440 | ±299 | 10909 | ±1847 | 12429 | ±1673 |
| 4 | 3023 | ±308 | 2759 | ±105 | 17278 | ±1650 | 14307 | ±781 |
| 12 | 2759 | ±105 | 4857 | ±186 | 14307 | ±781 | 26270 | ±1473 |
| 24 | 6966 | ±72 | 7344 | ±65 | 39196 | ±174 | 38381 | ±161 | dpm = disintegrations per minute
sem = standard error of the mean

Example 19

Effect of Ezetimibe on Cholesterol Uptake.

The effect of ezetimibe on the ability of CHO cells stably transfected with mouse or rat NPC1L1 or mouse SR-B1 to take up ³H-labeled cholesterol was evaluated in pulse-chase experiments. One cDNA clone of mouse NPC1L1 (C7) and three clones of rat NPC1L1 (C7, C17 and C21) were evaluated. The ability of CHO cells stably transfected with mouse SR-B1, mouse NPC1L1 and rat NPC1L1 to take up labeled cholesterol, in the absence of ezetimibe, was also evaluated in the pulse-chase experiments. Data generated in these experiments are set forth, below, in Tables 4 and 5. Additionally, the quantity of total cholesterol taken up by transfected and untransfected CHO cells in the presence of four different unlabeled cholesterol concentrations was also evaluated. The data from these experiments is set forth, below, in Table 6.

Cells:
A. CHO cells stably transfected with rat or mouse NPC1L1 cDNA
B. CHO background (no transfection)
C. SR-B1 transfected CHO cells
    Cells seeded at 500,000 cells/well (mL) in 12-well plates.

Procedure:
All reagents and culture plates were maintained at 37° C. unless otherwise noted.
Starve. The maintenance media (F12 HAMS, 1% Pen/Strep, 10% FCS) was removed and the cells were rinsed with serum-free HAMS media. The serum-free media was then replaced with 1 mL "starve" media (F12 HAMS, Pen/Strep, 5% lipoprotein deficient serum (LPDS). The cells were then starved overnight.
Pre-Incubation/pre-dose. Media was removed from all plates and replaced with fresh starve media and preincubated for 30 minutes. Half of the wells received media containing ezetimibe (stock soln in EtOH; final conc.=10 μM).
³H-Cholesterol Pulse. The following was added directly to each well:
  0.5 μCi ³H-cholesterol (~1.1×10⁶ dpm/well) in 50 μl of a mixed bile salt micelle
  4.8 mM sodium taurocholate (2.581 mg/mL)
  0.6 mM sodium oleate (0.183 mg/mL)
  0.25 mM cholesterol (0.1 mg/mL)
  Dispersed in "starve" media by ultrasonic vibration
  Final media cholesterol concentration=5 μg/mL
  Labeled cholesterol pulse time points were 4, 12, 24 minutes and 4 hours. Triplicate wells were prepared for each treatment.
Wash. At designated times, media was aspirated and cells were washed once with Hobbs Buffer A (50 mM Tris, 0.9% NaCl, 0.2% bovine serum albumin (BSA), pH 7.4) and once with Hobbs Buffer B (50 mM Tris, 0.9% NaCl, pH 7.4 (no BSA)) at 37° C.
Processing/Analysis.
A. 4, 12, 24 minute time points: Cells were digested overnight with 0.2N NaOH, 2 mL/well, room temperature. One 1.5 mL aliquot was removed from each well, neutralized & counted for radioactivity by scintillation counting.
B. 4 hour time point: The digested cells were analyzed by thin-layer chromatography to determine the content of cholesteryl ester in the cells.
   Extracts were spotted onto TLC plates and run for 30 minutes in 2 ml hexane:isopropanol (3:2) mobile phase for 30 minutes, followed by a second run in 1 ml hexane:isopropanol (3:2) mobile phase for 15 minutes.
C. Protein determination of cell extracts. Plates containing a sample of the cell extracts were placed on orbital shaker at 120 rpm for indicated times and then extracts are pooled into 12×75 tubes. Plates were dried and NaOH (2 ml/well) added. The protein content of the samples were then determined. Two additional 50 μl aliquots from all wells were assayed for total protein by the Pierce micro BCA method. The quantity of labeled cholesterol observed in the cells was normalized to the quantity of protein in the cells.

TABLE 4

Total Cholesterol in Transfected CHO Cells in the Presence and Absence of Ezetimibe.

| Clones: | Total Cholesterol, dpm ± sem | | | | Total Cholesterol, dpm/mg protein ± sem | | | |
|---|---|---|---|---|---|---|---|---|
| | Vehicle | | EZ (10 μM) | | Vehicle | | EZ (10 μM) | |
| 4 Min Pulse | | | | | | | | |
| CHO Control | 3413 | ±417 | 3222 | ±26 | 33443 | ±4070 | 31881 | ±483 |
| SR-BI | 14207 | ±51 | 10968 | ±821 | 118242 | ±1261 | 92474 | ±2902 |
| mNPC1L1(C7) | 4043 | ±419 | 4569 | ±222 | 30169 | ±3242 | 30916 | ±1137 |
| rNPC1L1(C21) | 3283 | ±288 | 3769 | ±147 | 23728 | ±2111 | 27098 | ±689 |
| rNPC1L1(C17) | 3188 | ±232 | 3676 | ±134 | 24000 | ±832 | 28675 | ±527 |
| rNPC1L1(C7) | 1825 | ±806 | 3268 | ±121 | 15069 | ±6794 | 27285 | ±968 |
| 12 Min Pulse | | | | | | | | |
| CHO Control | 4710 | ±246 | 4532 | ±165 | 44208 | ±2702 | 43391 | ±1197 |
| SR-BI | 16970 | ±763 | 12349 | ±298 | 140105 | ±6523 | 98956 | ±4447 |
| mNPC1L1(C7) | 6316 | ±85 | 6120 | ±755 | 45133 | ±342 | 41712 | ±4054 |
| rNPC1L1(C21) | 5340 | ±12 | 4703 | ±231 | 40018 | ±1181 | 33985 | ±1928 |
| rNPC1L1(C17) | 4831 | ±431 | 4579 | ±257 | 37378 | ±3461 | 34063 | ±1619 |
| rNPC1L1(C7) | 4726 | ±272 | 4664 | ±63 | 39100 | ±2350 | 38581 | ±784 |
| 24 Min Pulse | | | | | | | | |
| CHO Control | 7367 | ±232 | 6678 | ±215 | 65843 | ±1281 | 61764 | ±2131 |
| SR-BI | 39166 | ±2152 | 23558 | ±1310 | 324126 | ±11848 | 198725 | ±11713 |
| mNPC1L1(C7) | 10616 | ±121 | 9749 | ±482 | 77222 | ±1040 | 74041 | ±3670 |
| rNPC1L1(C21) | 9940 | ±587 | 8760 | ±293 | 76356 | ±9618 | 66165 | ±2181 |
| rNPC1L1(C17) | 8728 | ±721 | 8192 | ±237 | 70509 | ±5189 | 62279 | ±4352 |
| rNPC1L1(C7) | 8537 | ±148 | 7829 | ±204 | 72134 | ±1305 | 63482 | ±368 |

EZ = ezetimibe

TABLE 5

Cholesterol Ester in CHO cells in the Presence or Absence of Ezetimibe.

| Clones: | Vehicle | | EZ (10 μM) | | Vehicle | | EZ (10 μM) | |
|---|---|---|---|---|---|---|---|---|
| | 4 Hour Pulse | | | | | | | |
| | Cholesteryl Ester, dpm ± sem | | | | Cholesteryl Ester, dpm/mg protein ± sem | | | |
| CHO Control | 652 | ±13 | 208 | ±9 | 5647 | ±55 | 1902 | ±87 |
| SR-BI | 47608 | ±1292 | 9305 | ±401 | 391067 | ±14391 | 72782 | ±3181 |
| mNPC1L1(C7) | 732 | ±127 | 453 | ±118 | 4994 | ±827 | 3057 | ±776 |
| rNPC1L1(C21) | 2667 | ±90 | 454 | ±33 | 18655 | ±1032 | 3193 | ±265 |
| rNPC1L1(C17) | 751 | ±74 | 202 | ±10 | 5379 | ±481 | 1510 | ±62 |
| rNPC1L1(C7) | 462 | ±25 | 191 | ±54 | 3597 | ±193 | 1496 | ±403 |

TABLE 5-continued

Cholesterol Ester in CHO cells in the Presence or Absence of Ezetimibe.

| Clones: | Vehicle | EZ (10 μM) | Vehicle | EZ (10 μM) |
|---|---|---|---|---|
| | 4 Hour Pulse | | | |
| | Free Cholesterol, dpm ± sem | | Free Cholesterol, dpm/mg protein ± sem | |
| CHO Control | 61612 ±1227 | 56792 ±568 | 533876 ±17770 | 519607 ±16203 |
| SR-BI | 214678 ±4241 | 194519 ±474 | 1762873 ±46607 | 1521341 ±4185 |
| mNPC1L1(C7) | 79628 ±793 | 77516 ±1910 | 544661 ±1269 | 523803 ±10386 |
| rNPC1L1(C21) | 71352 ±1343 | 69106 ±711 | 498016 ±8171 | 485460 ±4410 |
| rNPC1L1(C17) | 78956 ±3782 | 71646 ±446 | 566456 ±29204 | 536651 ±7146 |
| rNPC1L1(C7) | 75348 ±2093 | 70628 ±212 | 586127 ±13932 | 556855 ±7481 |

EZ = ezetimibe

TABLE 6

Uptake of labeled cholesterol in the presence of increasing amounts of unlabeled cholesterol.

| Cold Cholesterol | CHO Control | SR-BI | mNPC1L1(C7) | rNPC1L1(C21) | CHO Control | SR-BI | mNPC1L1(C7) | rNPC1L1(C21) |
|---|---|---|---|---|---|---|---|---|
| | Total Cholesterol, dpm ± sem | | | | Total Cholesterol, dpm/mg protein ± sem | | | |
| | 24 Min Pulse | | | | | | | |
| 3 μg/mL | 12271 ± 430 | 49603 ± 2428 | 14350 ± 1628 | 10656 ± 1233 | 108936 ± 5413 | 541562 ± 13785 | 140764 ± 14433 | 94945 ± 12916 |
| 10 μg/mL | 16282 ± 2438 | 79967 ± 8151 | 24565 ± 3037 | 13225 ± 4556 | 151283 ± 23345 | 880224 ± 82254 | 250985 ± 27431 | 123433 ± 34092 |
| 30 μg/mL | 14758 ± 1607 | 71925 ± 3863 | 19001 ± 1530 | 13218 ± 1149 | 135109 ± 12106 | 796236 ± 18952 | 180436 ± 12112 | 111522 ± 6941 |
| 100 μg/mL | 16458 ± 1614 | 58185 ± 4548 | 15973 ± 1665 | 11560 ± 1132 | 149559 ± 17977 | 630143 ± 3718 | 147717 ± 8261 | 101328 ± 7191 |
| | Cholesteryl Ester, dpm ± sem | | | | Cholesteryl Ester, dpm/mg protein ± sem | | | |
| | 4 Hour Pulse | | | | | | | |
| 3 μg/mL | 2737 ± 114 | 39596 ± 1241 | 1561 ± 1 | 4015 ± 47 | 22050 ± 978 | 382641 ± 5955 | 13684 ± 217 | 32020 ± 641 |
| 10 μg/mL | 1646 ± 76 | 17292 ± 362 | 998 ± 36 | 1866 ± 33 | 157914 ± 3400 | 8917 ± 467 | 14849 ± 127 | 123433 ± 34092 |
| 30 μg/mL | 970 ± 46 | 6642 ± 153 | 537 ± 82 | 970 ± 325 | 7627 ± 1760 | 63547 ± 748 | 4885 ± 100 | 7741 ± |
| 100 μg/mL | 895 ± 156 | 4777 ± 27 | 777 ± 16 | 7135 ± 1230 | 45088 ± 1526 | 3663 ± 68 | 6005 ± 198 | 101328 ± 7191 |
| | Free Cholesterol, dpm ± sem | | | | Free Cholesterol, dpm/mg protein ± sem | | | |
| | 4 Hour Pulse | | | | | | | |
| 3 μg/mL | 89013 ± 3724 | 211783 ± 3268 | 104343 ± 2112 | 92244 ± 987 | 717308 ± 34130 | 2047695 ± 16213 | 914107 ± 5869 | 735498 ± 11209 |
| 10 μg/mL | 136396 ± 3566 | 278216 ± 10901 | 196173 ± 4721 | 125144 ± 877 | 1105118 ± 76074 | 2540130 ± 92471 | 1753072 ± 86578 | 996824 ± 27850 |

TABLE 6-continued

Uptake of labeled cholesterol in the presence of increasing amounts of unlabeled cholesterol.

| Cold Cholesterol | CHO Control | SR-BI | mNPC1L1(C7) | rNPC1L1(C21) | CHO Control | SR-BI | mNPC1L1(C7) | rNPC1L1(C21) |
|---|---|---|---|---|---|---|---|---|
| 30 µg/mL | 131745 ± 2922 | 224429 ± 2556 | 149172 ± 19689 | 117143 ± 4976 | 1036195 ± 21142 | 2149315 ± 78068 | 1357136 ± 180264 | 934772 ± 43202 |
| 100 µg/mL | 79336 ± 4011 | 231470 ± 4221 | 114599 ± 2803 | 93538 ± 1588 | 632965 ± 29756 | 2182022 ± 36793 | 1035979 ± 30329 | 723225 ± 21694 |

| | Cholesteryl Ester, dpm ± sem | | | | Cholesteryl Ester, dpm/mg protein ± sem | | | |
|---|---|---|---|---|---|---|---|---|
| | 24 Hour Pulse | | | | | | | |
| 3 µg/mL | 57373 ± 2704 | 162296 ± 1644 | 22986 ± 940 | 59377 ± 953 | 357629 ± 14639 | 1248900 ± 18565 | 160328 ± 6565 | 401315 ± 5557 |
| 10 µg/mL | 33730 ± 1296 | 112815 ± 373 | 14836 ± 552 | 31797 ± 5942 | 215004 ± 5942 | 830231 ± 12764 | 98594 ± 4205 | 200451 ± 5239 |
| 30 µg/mL | 19193 ± 100 | 58668 ± 1413 | 8878 ± 355 | 18963 ± 380 | 122071 ± 1271 | 446581 ± 3472 | 59091 ± 2697 | 119728 ± 2131 |
| 100 µg/mL | 16761 ± 398 | 31280 ± 1270 | 8784 ± 946 | 14933 ± 311 | 103235 ± 1739 | 272796 ± 13392 | 60670 ± 4597 | 96215 ± 1023 |

| | Free Cholesterol, dpm ± sem | | | | Free Cholesterol, dpm/mg protein ± sem | | | |
|---|---|---|---|---|---|---|---|---|
| | 24 Hour Pulse | | | | | | | |
| 3 µg/mL | 248985 ± 4207 | 357819 ± 4519 | 285610 ± 5187 | 227244 ± 1016 | 1552637 ± 18954 | 2752957 ± 24984 | 1993256 ± 56968 | 1536023 ± 10304 |
| 10 µg/mL | 231208 ± 8927 | 269822 ± 5872 | 311777 ± 8227 | 231666 ± 6198 | 1477414 ± 85954 | 1984473 ± 18420 | 2069980 ± 25517 | 1461157 ± 58517 |
| 30 µg/mL | 203566 ± 6008 | 225273 ± 5932 | 279604 ± 6612 | 209372 ± 3386 | 1294878 ± 41819 | 1716066 ± 52581 | 1859476 ± 29507 | 1321730 ± 5452 |
| 100 µg/mL | 178424 ± 2379 | 167082 ± 2211 | 229832 ± 4199 | 182678 ± 7709 | 1099648 ± 25160 | 1455799 ± 9885 | 1599244 ± 76938 | 1177546 ± 51191 |

Example 20

Labeled Cholesterol Uptake Assay.

In this example, the ability of CHO cells transiently transfected with rat NPC1L1 or mouse SR-B1 to take up labeled cholesterol was evaluated. Also evaluated was the ability of rat NPC1L1 to potentiate the ability of CHO cells transfected with mouse SR-B1 to take up labeled cholesterol. In these assays, cholesterol uptake, at a single concentration, was evaluated in pulse-chase experiments. The data generated in these experiments are set forth, below, in Table 7.

Cells:
A. CHO background cells (mock transfection).
B. CHO cells transiently transfected with mouse SR-B1.
C. CHO transiently transfected with rat NPC1L1 cDNAs (n=8 clones). Transiently transfected cells were seeded at 300,000 cells/well (mL) in 12-well plates.

Procedure:
All reagents and culture plates were maintained at 37° C. unless otherwise noted.

Starve. The maintenance media (F12 HAMS, 1% Pen/Strep, 10% FCS) was removed from the cells and replaced with 1 mL "starve" media (F12 HAMS, Pen/Strep, 5% lipoprotein deficient serum (LPDS). Cells were starved for 1 hour.

$^3$H-Cholesterol Pulse. The following was added directly to each well.

0.5 µCi $^3$H-cholesterol (~1.1×10$^6$ dpm/well) in 50 µl of a mixed bile salt micelle.
4.8 mM sodium taurocholate (2.581 mg/mL)
0.6 mM sodium oleate (0.183 mg/mL)
0.25 mM cholesterol (0.1 mg/mL)
Dispersed in "starve" media by ultrasonic vibration
Final media cholesterol concentration=5 µg/mL
Labeled cholesterol pulse time points were 24 Min and 4 hours. Triplicate wells for each treatment.

Wash. At the designated times, media was aspirated and cells were washed once with Hobbs Buffer A (50 mM Tris, 0.9% NaCl, 0.2% BSA, pH 7.4) and once with Hobbs Buffer B (50 mM Tris, 0.9% NaCl, pH 7.4 (no BSA)) at 37° C.

Processing/Analysis.

A. 24 minute time point: Cells were digested overnight with 0.2N NaOH, 2 mL/well at room temp. One, 1.5 mL aliquot was removed from each well, neutralized & counted for radioactivity by scintillation counting.

B. 4 hour time point: The digested cells were analyzed by thin-layer chromatography to determine the content of cholesterol ester in the cells.

The extracts were spotted onto thin layer chromatography plates and run in 2 ml hexane:isopropanol (3:2) containing mobile phase for 30 minutes, followed by a second run in 1 ml hexane:isopropanol (3:2) containing mobile phase for 15 min.

C. Protein determination of cell extracts: Plates containing a sample of the cell extracts were placed on orbital shaker at 120 rpm for indicated times and then extracts are pooled into 12×75 tubes. Plates were dried and NaOH (2 ml/well) added. The protein content of the samples were then determined. Two additional 50 µl aliquots from all wells were assayed for total protein by the Pierce micro BCA method. The quantity of labeled cholesterol observed in the cells was normalized to the quantity of protein in the cells.

TABLE 7

Labeled cholesterol uptake in transiently transfected CHO cells.

| Transfection | dpm | dpm/mg protein |
|---|---|---|
| Total Cholesterol, ± sem 24 Min Pulse | | |
| CHO Control(mock) | 4721 ± 436 | 49024 ± 4328 |
| SR-BI(Transient) | 5842 ± 82 | 59445 ± 1099 |
| NPC1L1(Transient) | 4092 ± 377 | 47026 ± 2658 |
| SR-BI/NPC1L1(trans) | 3833 ± 158 | 52132 ± 3071 |
| Cholesteryl Ester, ± sem 4 Hour Pulse | | |
| CHO Control(mock) | 2132 ± 40 | 20497 ± 640 |
| SR-BI(Transient) | 5918 ± 237 | 51812 ± 1417 |
| NPC1L1(Transient) | 1944 ± 93 | 19788 ± 642 |
| SR-BI/NPC1L1(trans) | 4747 ± 39 | 58603 ± 1156 |
| Free Cholesterol, ± sem 4 Hour Pulse | | |
| CHO Control(mock) | 45729 ± 328 | 439346 ± 5389 |
| SR-BI(Transient) | 50820 ± 2369 | 444551 ± 9785 |
| NPC1L1(Transient) | 39913 ± 1211 | 406615 ± 6820 |
| SR-BI/NPC1L1(trans) | 37269 ± 1225 | 459509 ± 6195 |

Example 21

Expression of rat, mouse and human NPC1L1.

In this example, NPC1L1 was introduced into cells and expressed. Species specific NPC1L1 expression constructs were cloned into the plasmid pCDNA3 using clone specific PCR primers to generate the ORF flanked by appropriate restriction sites compatible with the polylinker of the vector. For all three species of NPC1L1, small intestine total tissue RNA was used as a template for reverse transcriptase-polymerase chain reaction (RT-PCR) using oligo dT as the template primer. The rat NPC1L1 was cloned as an EcoRI fragment, human NPC1L1 was cloned as a XbaI/NotI fragment and mouse NPC1L1 was cloned as an EcoRI fragment. Forward and reverse strand sequencing of each clone was performed to confirm sequence integrity. Standard transient transfection procedures were used with CHO cells. In a 6-well plate CHO cells were plated 1 day before transfection at a plating density of $2 \times 10^5$ cells/well. The following day, cells were incubated with 2 µg plasmid DNA and 6 µL Lipofectamine for 5 hours followed a fresh media change. Forty-eight hours later, cells were analyzed for NPC1L1 expression using anti-NPC1L1 antisera by either FACS or western blot. To establish stable long term cell lines expressing NPC1L1, transfected CHO cells were selected in the presence of geneticin (G418, 0.8 mg/ml) as recommended by the manufacturer (Life Technologies). Following one month of selection in culture, the cell population was stained with anti-NPC1L1 antisera and sorted by FACS. Individual positive staining cells were cloned after isolation by limiting dilution and then maintained in selective media containing geneticin (0.5 mg/ml).

Other cell types less susceptible to transfection procedures have been generated using adenoviral vector systems. This system used to express NPC1L1 is dervied from Ad 5, a type C adenovirus. This recombinant replication-defective adenoviral vector is made defective through modifications of the E1, E2 and E4 regions. The vector also has additional modifications to the E3 region generally affecting the E3b region genes RIDa and RIDb. NPC1L1 expression was driven using the CMV promoter as an expression cassette substituted in the E3 region of the adenovirus. Rat and mouse NPC1L1 were amplified using clone specific primers flanked by restriction sites compatible with the adenovirus vector Adenovirus infective particles were produced from 293-D22 cells in titers of $5 \times 10^{10}$ P/mL. Viral lysates were used to infect cells resistant to standard transfection methodologies. In Caco2 cells, which are highly resistant to heterologous protein expression, adenovirus mediated expression of NPC1L1 has been shown by western blot analysis to persist at least 21 days post-infection.

Example 22

NPC1L1 Knock-Out Transgenic Mouse.

NPC1L1 knockout mice were constructed via targeted mutagenesis. This methodology utilized a targeting construct designed to delete a specific region of the mouse NPC1L1 gene. During the targeting process the *E. coli* lacZ reporter gene was inserted under the control of the endogenous NPC1L1 promoter. The region in NPC1L1 (SEQ ID NO: 45) being deleted is from nucleotide 790 to nucleotide 998. The targeting vector contains the LacZ-Neo cassette flanked by 1.9 kb 5' arm ending with nucleotide 789 and a 3.2 kb 3' arm starting with nucleotide 999. Genomic DNA from the recombinant embryonic stem cell line was assayed for homologous recombination using PCR. Amplified DNA fragments were visualized by agarose gel electrophoresis. The test PCRs employed a gene specific primer, which lies outside of and adjacent to the targeting vector arm, paired with one of three primers specific to the LacZ-Neo cassette sequence. For 5' PCR reconfirmation, the NPC1L1 specific oligonucleotide ATGTTAGGTGAGTCTGAACCTACCC (SEQ ID NO: 46) and for 3'PCR reconfirmation the NPC1L1 specific oligonucleotide GGATTGCATTTCCTTCAA GAAAGCC (SEQ ID NO: 47) were used. Genotyping of the F2 mice was performed by multiplex PCR using the NPC1L1 specific forward primer TATGGCTCTGCCC TCTGCAATGCTC (SEQ ID NO: 48) the LacZ-Neo cassette specific forward primer TCAGCAGCCTCTGTTCCA-CATACACTTC (SEQ ID NO: 49) in combination with the NPC1L1 gene specific reverse primer GTTCCA-CAGGGTCTGTGGTGAGTTC (SEQ ID NO: 50) allowed for determination of both the targeted and endogenous alleles. Analysis of the PCR products by agarose gel electrophoresis distinguished the wild-type, heterozygote and homozygote null mouse from each other.

Example 23

Acute Cholesterol Absorption in NPC1L1-Deficient Mice.

To determine whether NPC1L1 plays a role in cholesterol absorption, NPC1L1 deficient mice were studied.

Mice deficient in NPC1L1 (−/−) were generated by breeding heterozygote mice (+/) to obtain wild-type (+/+) and NPC1L1 deficient mice (−/−). Non-fasted mice (6.5–9 weeks old, mixed 129 and C57BL/6 background) were weighed and grouped (n=2 −/− and n=4 +/+). All animals were gavaged (Feeding needles, 24 G×1 inch, Popper and Sons, NY) with 0.1 ml corn oil (Sigma; St. Louis, Mo.) containing 1 µCi $^{14}$C-cholesterol (New England Nuclear, [$^{4-14}$C] Cholesterol, NEC-018) and 0.1 mg carrier cholesterol mass (Sigma; St. Louis, Mo.). Two hours later, blood was collected by heart puncture. The liver was removed, weighed, and three samples were placed into 20 ml counting vials. Tissues were digested in 1 ml of 1N NaOH at 60° C. overnight. The tissue digests were acidified by addition of 250 µl of 4N HCl prior to liquid scintillation counting (LSC). Plasma was isolated by centrifugation at 10,000 rpm for 5 minutes in a microfuge and duplicate 100 µl aliquots of plasma were taken for LSC.

Cholesterol absorption, evaluated by this acute technique and expressed as the total amount of radioactive cholesterol in the plasma and liver, demonstrated that the wild type mice (+/+) absorbed an average of 11,773 dpm and NPC1L1 deficient mice absorbed 992 dpm of the $^{14}$C-cholesterol. These results indicate that the NPC1L1 deficient mice have a 92% reduction in cholesterol absorption. These data confirm the role of NPC1L1 in intestinal cholesterol absorption. Inhibition of NPC1L1-mediated cholesterol absorption, in a subject, by administering NPC1L1 antagonists, such as ezetimibe, to the subject, are a useful way to reduce serum cholesterol levels and the occurrence of atherosclerosis in the subject.

Example 24

Cholesterol Absorption in NPC1L1 (NPC3) Knockout Mice (Fecal Ratio Method: Cholesterol/Sitostanol).

In this example, cholesterol absorption and the activity of ezetimibe was determined in the NPC1L1 knockout mice (−/−), heterozygous mice (+/−), and age matched wild-type mice (+/+).

Cholesterol absorption in the mice was determined by the dual fecal isotope ratio method as described by Altmann et al. (Biochim. Biophys. Acta. 1580(1):77–93 (2002)). Mice (n=4–6/group) were fed a standard rodent chow diet and in some groups treated daily with a maximally effective dose of ezetimibe (10 mg/kg). Mice were gavaged with $^{14}$C-cholesterol (1 µCi, 0.1 mg unlabeled cholesterol) and $^{3}$H-sitostanol (2 µCi) in 0.1 ml corn oil. Feces were collected for 2 days and fecal $^{14}$C-cholesterol and $^{3}$H-sitostanol levels were determined by combustion in a Packard Oxidizer. The fraction of cholesterol absorbed, as evaluated by the fecal dual isotope technique, was similar in wild type (+/+) and heterozygous mice (+/−) fed a chow diet (heterozygous mice absorbed 46±5% and age matched wild type mice absorbed 51±3% of the dose of $^{14}$C-cholesterol). The NPC1L1 knockout mice (−/−) absorbed 15.6±0.4% of the $^{14}$C-cholesterol, which was similar to the wild type mice treated with a maximally effective dose of ezetimibe (16.1±0.3%), and reduced by 69% compared to wild type mice (p<0.001). In NPC1L1 knockout treated with ezetimibe at 10 mg/kg/day, cholesterol absorption was similar to that seen in the untreated knockout mice (16.2±0.6% compared to 15.6%±0.4%, respectively). Thus, the majority of cholesterol absorption is dependent on the presence of NPC1L1 and the residual cholesterol absorption in mice lacking NPC1L1 is insensitive to ezetimibe treatment. These results indicate that NPC1L1 is involved in the small intestinal enterocyte uptake and absorption of cholesterol and is in the ezetimibe sensitive pathway.

Example 25

Mouse Screening Assay (Acute Cholesterol Absorption).

The following screening assay is used to identify the presence of an NPC1L1 antagonist in a sample.

Mice deficient in NPC1L1 (−/−) are generated by breeding heterozygote mice (+/) to obtain wild-type (+/+) and NPC1L1 deficient mice (−/−).

In a first set of experiments, non-fasted mice (6.5–9 weeks old, mixed 129 and C57BL/6 background) are weighed and grouped (n=1 to 4−/− and n=1 to 4+/+). All animals are gavaged (Feeding needles, 24 G×1 inch, Popper and Sons, NY) with 0.1 ml corn oil (Sigma; St. Louis, Mo.) containing 1 µCi $^{14}$C-cholesterol (New England Nuclear, [$^{4-14}$C] Cholesterol, NEC-018) and 0.1 mg carrier cholesterol mass (Sigma; St. Louis, Mo.).

In another set of experiments, 1 to 4 wild-type NPC1L1 mice (+/+) are treated identically to the mice in the first set of experiments, above, except that the mice are additionally fed a sample to be tested for the presence of an NPC1L1 antagonist.

Two hours later, blood is collected from each mouse by heart puncture. The liver is removed, weighed, and three samples are placed into 20 ml counting vials. Tissues are digested in 1 ml of 1N NaOH at 60° C. overnight. The tissue digests are acidified by addition of 250 µl of 4N HCl prior to liquid scintillation counting (LSC). Plasma is isolated by centrifugation at 10,000 rpm for 5 minutes in a microfuge and duplicate 100 µl aliquots of plasma are taken for LSC.

Cholesterol absorption, evaluated by this acute technique is expressed as the total amount of radioactive cholesterol in the plasma and liver. The sample tested is determined to contain an NPC1L1 antagonist when the level of cholesterol absorption (as measured by the above described methods) in the wild-type NPC1L1 mouse (+/+) which was fed the sample and in the NPC1L1 deficient mouse (−/−) are less than the amount of cholesterol absorption in the wild-type NPC1L1 mouse (+/+) which was not fed the sample.

Example 26

Mouse Screening Assay (Fecal Ratio Method: Cholesterol/Sitostanol).

The following screening assay is used to identify the presence of an NPC1L1 antagonist in a sample.

Cholesterol absorption in the mice is determined by the dual fecal isotope ratio method as described by Altmann et al. (Biochim. Biophys. Acta. 1580(1):77–93 (2002)).

Three groups of mice (n=1–6/group) are assembled. Two separate groups comprise wild-type NPC1L1 mice (+/+) and one group comprises NPC1L1 deficient mice (−/−).

Each group is fed a standard rodent chow diet and in some groups treated daily. Mice are gavaged with $^{14}$C-cholesterol (1 µCi, 0.1 mg unlabeled cholesterol) and $^{3}$H-sitostanol (2 µCi) in 0.1 ml corn oil. One group of mice, which comprise wild-type NPC1L1 mice (+/+) are further fed a sample to be tested for the presence of an NPC1L1 antagonist. Feces are collected for 2 days and fecal $^{14}$C-cholesterol and $^{3}$H-sitostanol levels are determined by combustion in a Packard Oxidizer.

The sample tested is determined to contain an NPC1L1 antagonist when the level of cholesterol and/or sitostanol absorption (as measured by the above described methods) in the wild-type NPC1L1 mouse (+/+) which was fed the sample and in the NPC1L1 deficient mouse (−/−) are less than the amount of cholesterol and/or sitostanol absorption in the wild-type NPC1L1 mouse (+/+) which was not fed the sample.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, Genbank Accession Numbers and protocols are cited throughout this application, the disclosures of which are incorporated herein by reference in their entireties for all purposes.

We claim:

1. An isolated polypeptide comprising the amino acid sequence set forth in SEQ ID NO: 4.

2. A polypeptide of claim 1 which is labeled with a member selected from the group consisting of $^{32}$P, $^{35}$S, $^{3}$H, $^{99m}$Tc, $^{123}$I, $^{111}$In, $^{68}$Ga, $^{8}$F, $^{125}$I, $^{131}$I, $^{113m}$In, $^{76}$Br, $^{67}$Ga, $^{99m}$Tc, $^{123}$I, $^{111}$In, and $^{68}$Ga.

3. The polypeptide of claim 1 which is glycosylated.

4. The polypeptide of claim 1 which is capable of binding to cholesterol.

5. A fusion polypeptide comprising the polypeptide of claim 1 fused to another polypeptide.

6. The polypeptide of claim 5 wherein the other polypeptide is selected from the group consisting of a glutathione-s-transferase (GST) tag polypeptide, a hexahistidine tag polypeptide, a maltose binding protein tag, a haemagglutinin polypeptide tag, a cellulose binding protein tag and a myc tag polypeptide.

7. A composition comprising the polypeptide of claim 1 bound to cholesterol.

8. The composition of claim 7 wherein said cholesterol is radiolabled.

9. The composition of claim 8 wherein the radiolabel is $^{125}$I or $^{3}$H.

10. A composition comprising the polypeptide of claim 1 bound to ezetimibe.

11. The composition of claim 10 wherein said ezetimibe is radiolabled.

12. The composition of claim 11 wherein the radiolabel is $^{125}$I or $^{3}$H.

13. The composition of claim 10 wherein the ezetimibe is BODIPY labeled ezetimibe.

* * * * *

SEQUENCE LISTING

```
<160> NUMBER OF SEQ ID NOS: 51

<210> SEQ ID NO 1
<211> LENGTH: 3996
<212> TYPE: DNA
<213> ORGANISM: Rattus sp.
<220> FEATURE:
<221> NAME/KEY: CDS
<222> LOCATION: (1)..(3996)
<223> OTHER INFORMATION:

<400> SEQUENCE: 1 atg gca gct gcc tgg ctg gga tgg ctg ctc tgg gcc ctg ctc ctg agc        48
Met Ala Ala Ala Trp Leu Gly Trp Leu Leu Trp Ala Leu Leu Leu Ser
1               5                   10                  15 gcg gcc cag ggt gag cta tac aca ccc aaa cac gaa gct ggg gtc tgc        96
Ala Ala Gln Gly Glu Leu Tyr Thr Pro Lys His Glu Ala Gly Val Cys
            20                  25                  30 acc ttt tac gaa gag tgc ggg aaa aac cca gag ctc tct gga ggc ctc       144
Thr Phe Tyr Glu Glu Cys Gly Lys Asn Pro Glu Leu Ser Gly Gly Leu
        35                  40                  45 acg tca cta tcc aat gta tcc tgc ctg tct aac acc ccg gcc cgc cac       192
Thr Ser Leu Ser Asn Val Ser Cys Leu Ser Asn Thr Pro Ala Arg His
    50                  55                  60 gtc acg ggt gaa cac ctg gct ctt ctc cag cgc atc tgt ccc cgc ctg       240
Val Thr Gly Glu His Leu Ala Leu Leu Gln Arg Ile Cys Pro Arg Leu
65                  70                  75                  80 tac aac ggc ccc aat acc act ttt gcc tgt tgc tct acc aag cag ctg       288
Tyr Asn Gly Pro Asn Thr Thr Phe Ala Cys Cys Ser Thr Lys Gln Leu
                85                  90                  95 ctg tcc tta gaa agc agc atg tcc atc acc aag gcc ctt ctc acg cgc       336
Leu Ser Leu Glu Ser Ser Met Ser Ile Thr Lys Ala Leu Leu Thr Arg
            100                 105                 110 tgc ccg gcc tgc tct gac aat ttt gtg agc tta cac tgc cac aac act       384
Cys Pro Ala Cys Ser Asp Asn Phe Val Ser Leu His Cys His Asn Thr
        115                 120                 125 tgc agc cct gac cag agc ctc ttc atc aac gtc acc cgg gtg gtt gag       432
```

-continued

| | | |
|---|---|---|
| Cys Ser Pro Asp Gln Ser Leu Phe Ile Asn Val Thr Arg Val Val Glu<br>130                 135                 140 | | |
| cgg ggc gct gga gag cct cct gcc gtg gtg gcc tat gag gcc ttt tat<br>Arg Gly Ala Gly Glu Pro Pro Ala Val Val Ala Tyr Glu Ala Phe Tyr<br>145                 150                 155                 160 | | 480 |
| cag cgc agc ttt gct gag aag gcc tat gag tcc tgc agc cag gtg cgc<br>Gln Arg Ser Phe Ala Glu Lys Ala Tyr Glu Ser Cys Ser Gln Val Arg<br>            165                 170                 175 | | 528 |
| atc cct gcg gcc gct tcc ttg gcc gtg ggc agc atg tgt gga gtg tat<br>Ile Pro Ala Ala Ala Ser Leu Ala Val Gly Ser Met Cys Gly Val Tyr<br>          180                 185                 190 | | 576 |
| ggc tcc gcc ctc tgc aat gct cag cgc tgg ctc aac ttc caa gga gac<br>Gly Ser Ala Leu Cys Asn Ala Gln Arg Trp Leu Asn Phe Gln Gly Asp<br>        195                 200                 205 | | 624 |
| aca ggg aat ggc ctg gct ccg ctg gat atc acc ttc cac ctc ttg gag<br>Thr Gly Asn Gly Leu Ala Pro Leu Asp Ile Thr Phe His Leu Leu Glu<br>      210                 215                 220 | | 672 |
| cct ggc cag gcc cta ccg gat ggg atc cag cca ctg aat ggg aag atc<br>Pro Gly Gln Ala Leu Pro Asp Gly Ile Gln Pro Leu Asn Gly Lys Ile<br>225                 230                 235                 240 | | 720 |
| gca ccc tgc aac gag tct cag ggt gat gac tca gca gtc tgc tcc tgc<br>Ala Pro Cys Asn Glu Ser Gln Gly Asp Asp Ser Ala Val Cys Ser Cys<br>            245                 250                 255 | | 768 |
| cag gac tgt gcg gcg tcc tgc cct gtc atc cct ccg ccc gag gcc ttg<br>Gln Asp Cys Ala Ala Ser Cys Pro Val Ile Pro Pro Pro Glu Ala Leu<br>          260                 265                 270 | | 816 |
| cgc cct tcc ttc tac atg ggt cgc atg cca ggc tgg ctg gcc ctc atc<br>Arg Pro Ser Phe Tyr Met Gly Arg Met Pro Gly Trp Leu Ala Leu Ile<br>        275                 280                 285 | | 864 |
| atc atc ttc act gct gtc ttt gtg ttg ctc tct gca gtc ctt gtg cgt<br>Ile Ile Phe Thr Ala Val Phe Val Leu Leu Ser Ala Val Leu Val Arg<br>      290                 295                 300 | | 912 |
| ctc cga gtg gtt tcc aac agg aac aag aac aag gca gaa ggc ccc cag<br>Leu Arg Val Val Ser Asn Arg Asn Lys Asn Lys Ala Glu Gly Pro Gln<br>305                 310                 315                 320 | | 960 |
| gaa gcc ccc aaa ctc cct cat aag cac aaa ctc tca ccc cat acc atc<br>Glu Ala Pro Lys Leu Pro His Lys His Lys Leu Ser Pro His Thr Ile<br>            325                 330                 335 | | 1008 |
| ctg ggc cgg ttc ttc cag aac tgg ggc aca agg gtg gcc tcg tgg cca<br>Leu Gly Arg Phe Phe Gln Asn Trp Gly Thr Arg Val Ala Ser Trp Pro<br>          340                 345                 350 | | 1056 |
| ctc acc gtc tta gca ctg tcc ttc atc gtt gtg ata gcc tta gca gca<br>Leu Thr Val Leu Ala Leu Ser Phe Ile Val Val Ile Ala Leu Ala Ala<br>        355                 360                 365 | | 1104 |
| ggc ctg acc ttt att gaa ctc acc aca gac cct gtg gaa ctg tgg tcg<br>Gly Leu Thr Phe Ile Glu Leu Thr Thr Asp Pro Val Glu Leu Trp Ser<br>      370                 375                 380 | | 1152 |
| gcc ccc aag agc cag gcc cgg aaa gag aag tct ttc cat gat gag cat<br>Ala Pro Lys Ser Gln Ala Arg Lys Glu Lys Ser Phe His Asp Glu His<br>385                 390                 395                 400 | | 1200 |
| ttc ggc ccc ttc ttt cga acc aac cag att ttc gtg aca gct cgg aac<br>Phe Gly Pro Phe Phe Arg Thr Asn Gln Ile Phe Val Thr Ala Arg Asn<br>            405                 410                 415 | | 1248 |
| agg tcc agc tac aag tac gac tcc cta ctg cta ggg tcc aag aac ttc<br>Arg Ser Ser Tyr Lys Tyr Asp Ser Leu Leu Leu Gly Ser Lys Asn Phe<br>          420                 425                 430 | | 1296 |
| agt ggg atc ctg tcc ctg gac ttc ctg ctg gag ctg ctg gag ctt cag<br>Ser Gly Ile Leu Ser Leu Asp Phe Leu Leu Glu Leu Leu Glu Leu Gln<br>        435                 440                 445 | | 1344 |

```
                                                    -continued
gag agg ctt cga cac ctg caa gtg tgg tcc cct gag gca gag cgc aac    1392
Glu Arg Leu Arg His Leu Gln Val Trp Ser Pro Glu Ala Glu Arg Asn
    450                 455                 460 atc tcc ctc cag gac atc tgc tat gcc ccc ctc aac cca tat aac acc    1440
Ile Ser Leu Gln Asp Ile Cys Tyr Ala Pro Leu Asn Pro Tyr Asn Thr
465                 470                 475                 480 agc ctc tcc gac tgc tgt gtc aac agc ctc ctt cag tac ttc cag aac    1488
Ser Leu Ser Asp Cys Cys Val Asn Ser Leu Leu Gln Tyr Phe Gln Asn
                485                 490                 495 aac cgc acc ctc ctg atg ctc acg gcc aac cag act ctg aat ggc cag    1536
Asn Arg Thr Leu Leu Met Leu Thr Ala Asn Gln Thr Leu Asn Gly Gln
            500                 505                 510 acc tcc ctg gtg gac tgg aag gac cat ttc ctc tac tgt gca aat gcc    1584
Thr Ser Leu Val Asp Trp Lys Asp His Phe Leu Tyr Cys Ala Asn Ala
        515                 520                 525 cct ctc acg ttc aaa gat ggc acg tct ctg gcc ctg agc tgc atg gct    1632
Pro Leu Thr Phe Lys Asp Gly Thr Ser Leu Ala Leu Ser Cys Met Ala
    530                 535                 540 gac tac ggg gct cct gtc ttc ccc ttc ctt gct gtt ggg gga tac caa    1680
Asp Tyr Gly Ala Pro Val Phe Pro Phe Leu Ala Val Gly Gly Tyr Gln
545                 550                 555                 560 ggc acg gac tat tcc gag gca gaa gcg ctg atc ata acc ttc tct ctc    1728
Gly Thr Asp Tyr Ser Glu Ala Glu Ala Leu Ile Ile Thr Phe Ser Leu
                565                 570                 575 aat aac tac ccc gct gat gat ccc cgc atg gcc cag gcc aag ctc tgg    1776
Asn Asn Tyr Pro Ala Asp Asp Pro Arg Met Ala Gln Ala Lys Leu Trp
            580                 585                 590 gag gag gct ttc ttg aag gaa atg gaa tcc ttc cag agg aac aca agt    1824
Glu Glu Ala Phe Leu Lys Glu Met Glu Ser Phe Gln Arg Asn Thr Ser
        595                 600                 605 gac aag ttc cag gtt gcg ttc tca gct gag cgc tct ctg gag gat gag    1872
Asp Lys Phe Gln Val Ala Phe Ser Ala Glu Arg Ser Leu Glu Asp Glu
    610                 615                 620 atc aac cgc acc acc atc cag gac ctg cct gtc ttt gcc gtc agc tac    1920
Ile Asn Arg Thr Thr Ile Gln Asp Leu Pro Val Phe Ala Val Ser Tyr
625                 630                 635                 640 att atc gtc ttc ctg tac atc tcc ctg gcc ctg ggc agc tac tcc aga    1968
Ile Ile Val Phe Leu Tyr Ile Ser Leu Ala Leu Gly Ser Tyr Ser Arg
                645                 650                 655 tgc agc cga gta gcg gtg gag tcc aag gct act ctg ggc cta ggt ggg    2016
Cys Ser Arg Val Ala Val Glu Ser Lys Ala Thr Leu Gly Leu Gly Gly
            660                 665                 670 gtg att gtt gtg ctg gga gca gtt ctg gct gcc atg ggc ttc tac tcc    2064
Val Ile Val Val Leu Gly Ala Val Leu Ala Ala Met Gly Phe Tyr Ser
        675                 680                 685 tac ctg ggt gtc ccc tct tct ctg gtt atc atc caa gtg gta cct ttc    2112
Tyr Leu Gly Val Pro Ser Ser Leu Val Ile Ile Gln Val Val Pro Phe
    690                 695                 700 ctg gtg cta gct gtg gga gct gac aac atc ttc atc ttt gtt ctt gag    2160
Leu Val Leu Ala Val Gly Ala Asp Asn Ile Phe Ile Phe Val Leu Glu
705                 710                 715                 720 tac cag agg cta cct agg atg cct ggg gaa cag cga gag gct cac att    2208
Tyr Gln Arg Leu Pro Arg Met Pro Gly Glu Gln Arg Glu Ala His Ile
                725                 730                 735 ggc cgc acc ctg ggc agt gtg gcc ccc agc atg ctg ctg tgc agc ctc    2256
Gly Arg Thr Leu Gly Ser Val Ala Pro Ser Met Leu Leu Cys Ser Leu
            740                 745                 750 tct gag gcc atc tgc ttc ttt cta ggg gcc ctg acc ccc atg cca gct    2304
Ser Glu Ala Ile Cys Phe Phe Leu Gly Ala Leu Thr Pro Met Pro Ala
        755                 760                 765
```

-continued

| | |
|---|---|
| gtg agg acc ttc gcc ttg acc tct ggc tta gca att atc ctc gac ttc<br>Val Arg Thr Phe Ala Leu Thr Ser Gly Leu Ala Ile Ile Leu Asp Phe<br>770                             775                        780 | 2352 |
| ctg ctc cag atg act gcc ttt gtg gcc ctg ctc tcc ctg gat agc aag<br>Leu Leu Gln Met Thr Ala Phe Val Ala Leu Leu Ser Leu Asp Ser Lys<br>785                             790                         795                     800 | 2400 |
| agg cag gag gcc tct cgc ccg gat gtc tta tgc tgc ttt tca acc cgg<br>Arg Gln Glu Ala Ser Arg Pro Asp Val Leu Cys Cys Phe Ser Thr Arg<br>                        805                         810                         815 | 2448 |
| aag ctg ccc cca cct aaa gaa aaa gaa ggc ctc tta ctc cgc ttc ttc<br>Lys Leu Pro Pro Pro Lys Glu Lys Glu Gly Leu Leu Leu Arg Phe Phe<br>820                           825                       830 | 2496 |
| cgc aag ata tac gct cct ttc ctg ctg cac aga ttc atc cgc cct gtt<br>Arg Lys Ile Tyr Ala Pro Phe Leu Leu His Arg Phe Ile Arg Pro Val<br>                  835                         840                        845 | 2544 |
| gtg atg ctg ctg ttt ctg acc ctg ttt gga gca aat ctc tac tta atg<br>Val Met Leu Leu Phe Leu Thr Leu Phe Gly Ala Asn Leu Tyr Leu Met<br>850                           855                       860 | 2592 |
| tgc aac atc aac gtg ggg cta gac cag gag ctg gct ctg ccc aag gac<br>Cys Asn Ile Asn Val Gly Leu Asp Gln Glu Leu Ala Leu Pro Lys Asp<br>865                          870                       875                       880 | 2640 |
| tcg tac ttg ata gac tac ttc ctc ttt ctg aac cga tac ctt gaa gtg<br>Ser Tyr Leu Ile Asp Tyr Phe Leu Phe Leu Asn Arg Tyr Leu Glu Val<br>                  885                         890                        895 | 2688 |
| ggg cct cca gtg tac ttt gtc acc acc tcg ggc ttc aac ttc tcc agc<br>Gly Pro Pro Val Tyr Phe Val Thr Thr Ser Gly Phe Asn Phe Ser Ser<br>                   900                        905                        910 | 2736 |
| gag gca ggc atg aac gcc act tgc tct agc gca ggc tgt aag agc ttc<br>Glu Ala Gly Met Asn Ala Thr Cys Ser Ser Ala Gly Cys Lys Ser Phe<br>                  915                        920                       925 | 2784 |
| tcc cta acc cag aaa atc cag tat gcc agt gaa ttc cct gac cag tct<br>Ser Leu Thr Gln Lys Ile Gln Tyr Ala Ser Glu Phe Pro Asp Gln Ser<br>930                           935                       940 | 2832 |
| tac gtg gct att gct gca tcc tcc tgg gta gat gac ttc atc gac tgg<br>Tyr Val Ala Ile Ala Ala Ser Ser Trp Val Asp Asp Phe Ile Asp Trp<br>945                           950                       955                     960 | 2880 |
| ctg acc ccg tcc tcc tcc tgc tgt cgc ctt tat ata cgt ggc ccc cat<br>Leu Thr Pro Ser Ser Ser Cys Cys Arg Leu Tyr Ile Arg Gly Pro His<br>                   965                        970                      975 | 2928 |
| aag gat gag ttc tgt ccc tca acg gat act tcc ttc aac tgc tta aaa<br>Lys Asp Glu Phe Cys Pro Ser Thr Asp Thr Ser Phe Asn Cys Leu Lys<br>                 980                        985                       990 | 2976 |
| aac tgc atg aac cgc act ctg ggt  cct gtg agg ccc aca  gcg gaa cag<br>Asn Cys Met Asn Arg Thr Leu Gly Pro Val Arg Pro Thr Ala Glu Gln<br>                 995                      1000                    1005 | 3024 |
| ttt cat aag tac ctg ccc tgg  ttc ctg aat gat ccg  ccc aat atc<br>Phe His Lys Tyr Leu Pro Trp Phe Leu Asn Asp Pro Pro Asn Ile<br>          1010                    1015                    1020 | 3069 |
| aga tgt ccc aaa ggg ggt cta  gca gcg tat aga acg  tct gtg aat<br>Arg Cys Pro Lys Gly Gly Leu Ala Ala Tyr Arg Thr Ser Val Asn<br>        1025                    1030                    1035 | 3114 |
| ttg agc tca gat ggc cag gtt  ata gcc tcc cag ttc  atg gcc tac<br>Leu Ser Ser Asp Gly Gln Val Ile Ala Ser Gln Phe Met Ala Tyr<br>          1040                    1045                    1050 | 3159 |
| cac aag ccc tta agg aac tca  cag gac ttc aca gaa  gct ctc cgg<br>His Lys Pro Leu Arg Asn Ser Gln Asp Phe Thr Glu Ala Leu Arg<br>        1055                    1060                    1065 | 3204 |
| gcg tcc cgg ttg cta gca gcc  aac atc aca gct gac  cta cgg aag<br>Ala Ser Arg Leu Leu Ala Ala Asn Ile Thr Ala Asp Leu Arg Lys | 3249 |

-continued

| | | | | | | | | | | | | | | |
|---|---|---|---|---|---|---|---|---|---|---|---|---|---|---|
| | | | | 1070 | | | | 1075 | | | | 1080 | | |
| gtg | cct | ggg | aca | gat | cca | aac | ttt | gag | gtc | ttc | cct | tac | acg | atc | 3294 |
| Val | Pro | Gly | Thr | Asp | Pro | Asn | Phe | Glu | Val | Phe | Pro | Tyr | Thr | Ile | |
| | 1085 | | | | 1090 | | | | | 1095 | | | | | |
| tcc | aac | gtg | ttc | tac | cag | caa | tac | ctg | acg | gtc | ctt | cct | gag | gga | 3339 |
| Ser | Asn | Val | Phe | Tyr | Gln | Gln | Tyr | Leu | Thr | Val | Leu | Pro | Glu | Gly | |
| | 1100 | | | | 1105 | | | | | 1110 | | | | | |
| atc | ttc | acc | ctt | gct | ctt | tgc | ttt | gtg | ccc | acc | ttt | gtt | gtc | tgc | 3384 |
| Ile | Phe | Thr | Leu | Ala | Leu | Cys | Phe | Val | Pro | Thr | Phe | Val | Val | Cys | |
| | 1115 | | | | 1120 | | | | | 1125 | | | | | |
| tac | ctc | cta | ctg | ggc | ctg | gac | atg | tgc | tca | ggg | atc | ctc | aac | cta | 3429 |
| Tyr | Leu | Leu | Leu | Gly | Leu | Asp | Met | Cys | Ser | Gly | Ile | Leu | Asn | Leu | |
| | 1130 | | | | 1135 | | | | | 1140 | | | | | |
| ctc | tcc | atc | att | atg | att | ctc | gtg | gac | acc | att | ggc | ctc | atg | gct | 3474 |
| Leu | Ser | Ile | Ile | Met | Ile | Leu | Val | Asp | Thr | Ile | Gly | Leu | Met | Ala | |
| | 1145 | | | | 1150 | | | | | 1155 | | | | | |
| gtg | tgg | ggt | atc | agc | tat | aat | gcg | gta | tcc | ctc | atc | aac | ctt | gtc | 3519 |
| Val | Trp | Gly | Ile | Ser | Tyr | Asn | Ala | Val | Ser | Leu | Ile | Asn | Leu | Val | |
| | 1160 | | | | 1165 | | | | | 1170 | | | | | |
| acg | gca | gtg | ggc | atg | tct | gtg | gag | ttt | gtg | tcc | cac | atc | act | cgg | 3564 |
| Thr | Ala | Val | Gly | Met | Ser | Val | Glu | Phe | Val | Ser | His | Ile | Thr | Arg | |
| | 1175 | | | | 1180 | | | | | 1185 | | | | | |
| tcc | ttt | gct | gta | agc | acc | aag | cct | acc | cgg | ctg | gag | agg | gct | aaa | 3609 |
| Ser | Phe | Ala | Val | Ser | Thr | Lys | Pro | Thr | Arg | Leu | Glu | Arg | Ala | Lys | |
| | 1190 | | | | 1195 | | | | | 1200 | | | | | |
| gat | gct | act | gtc | ttc | atg | ggc | agt | gcg | gtg | ttt | gct | gga | gtg | gcc | 3654 |
| Asp | Ala | Thr | Val | Phe | Met | Gly | Ser | Ala | Val | Phe | Ala | Gly | Val | Ala | |
| | 1205 | | | | 1210 | | | | | 1215 | | | | | |
| atg | acc | aac | ttc | cca | ggc | atc | ctc | atc | ttg | ggc | ttt | gcc | caa | gcc | 3699 |
| Met | Thr | Asn | Phe | Pro | Gly | Ile | Leu | Ile | Leu | Gly | Phe | Ala | Gln | Ala | |
| | 1220 | | | | 1225 | | | | | 1230 | | | | | |
| cag | ctt | att | cag | atc | ttc | ttc | cgc | ctc | aac | ctt | ctg | atc | acc | | 3744 |
| Gln | Leu | Ile | Gln | Ile | Phe | Phe | Arg | Leu | Asn | Leu | Leu | Ile | Thr | | |
| | 1235 | | | | 1240 | | | | | 1245 | | | | | |
| ttg | ctg | ggt | ctg | ctg | cat | ggc | ctg | gtc | ttc | ctg | ccg | gtt | gtc | ctc | 3789 |
| Leu | Leu | Gly | Leu | Leu | His | Gly | Leu | Val | Phe | Leu | Pro | Val | Val | Leu | |
| | 1250 | | | | 1255 | | | | | 1260 | | | | | |
| agc | tat | ctg | gga | cca | gat | gtt | aac | caa | gct | ctg | gta | cag | gag | gag | 3834 |
| Ser | Tyr | Leu | Gly | Pro | Asp | Val | Asn | Gln | Ala | Leu | Val | Gln | Glu | Glu | |
| | 1265 | | | | 1270 | | | | | 1275 | | | | | |
| aaa | cta | gcc | agc | gag | gca | gca | gtg | gcc | cca | gag | cct | tct | tgc | cca | 3879 |
| Lys | Leu | Ala | Ser | Glu | Ala | Ala | Val | Ala | Pro | Glu | Pro | Ser | Cys | Pro | |
| | 1280 | | | | 1285 | | | | | 1290 | | | | | |
| cag | tac | ccc | tcc | cct | gct | gat | gcg | gat | gcc | aat | gtt | aac | tac | ggc | 3924 |
| Gln | Tyr | Pro | Ser | Pro | Ala | Asp | Ala | Asp | Ala | Asn | Val | Asn | Tyr | Gly | |
| | 1295 | | | | 1300 | | | | | 1305 | | | | | |
| ttt | gcc | cca | gaa | ctt | gcc | cac | gga | gct | aat | gct | gct | aga | agc | tct | 3969 |
| Phe | Ala | Pro | Glu | Leu | Ala | His | Gly | Ala | Asn | Ala | Ala | Arg | Ser | Ser | |
| | 1310 | | | | 1315 | | | | | 1320 | | | | | |
| ttg | ccc | aaa | agt | gac | caa | aag | ttc | taa | | | | | | | 3996 |
| Leu | Pro | Lys | Ser | Asp | Gln | Lys | Phe | | | | | | | | |
| | 1325 | | | | 1330 | | | | | | | | | | |

<210> SEQ ID NO 2
<211> LENGTH: 1331
<212> TYPE: PRT
<213> ORGANISM: Rattus sp.

<400> SEQUENCE: 2

Met Ala Ala Ala Trp Leu Gly Trp Leu Leu Trp Ala Leu Leu Leu Ser

-continued

```
1               5                   10                  15
Ala Ala Gln Gly Glu Leu Tyr Thr Pro Lys His Glu Ala Gly Val Cys
                20                  25                  30

Thr Phe Tyr Glu Glu Cys Gly Lys Asn Pro Glu Leu Ser Gly Gly Leu
                35                  40                  45

Thr Ser Leu Ser Asn Val Ser Cys Leu Ser Asn Thr Pro Ala Arg His
    50                  55                  60

Val Thr Gly Glu His Leu Ala Leu Leu Gln Arg Ile Cys Pro Arg Leu
65                  70                  75                  80

Tyr Asn Gly Pro Asn Thr Thr Phe Ala Cys Cys Ser Thr Lys Gln Leu
                85                  90                  95

Leu Ser Leu Glu Ser Ser Met Ser Ile Thr Lys Ala Leu Leu Thr Arg
                100                 105                 110

Cys Pro Ala Cys Ser Asp Asn Phe Val Ser Leu His Cys His Asn Thr
                115                 120                 125

Cys Ser Pro Asp Gln Ser Leu Phe Ile Asn Val Thr Arg Val Val Glu
    130                 135                 140

Arg Gly Ala Gly Glu Pro Pro Ala Val Ala Tyr Glu Ala Phe Tyr
145                 150                 155                 160

Gln Arg Ser Phe Ala Glu Lys Ala Tyr Glu Ser Cys Ser Gln Val Arg
                165                 170                 175

Ile Pro Ala Ala Ala Ser Leu Ala Val Gly Ser Met Cys Gly Val Tyr
                180                 185                 190

Gly Ser Ala Leu Cys Asn Ala Gln Arg Trp Leu Asn Phe Gln Gly Asp
    195                 200                 205

Thr Gly Asn Gly Leu Ala Pro Leu Asp Ile Thr Phe His Leu Leu Glu
    210                 215                 220

Pro Gly Gln Ala Leu Pro Asp Gly Ile Gln Pro Leu Asn Gly Lys Ile
225                 230                 235                 240

Ala Pro Cys Asn Glu Ser Gln Gly Asp Asp Ser Ala Val Cys Ser Cys
                245                 250                 255

Gln Asp Cys Ala Ala Ser Cys Pro Val Ile Pro Pro Glu Ala Leu
    260                 265                 270

Arg Pro Ser Phe Tyr Met Gly Arg Met Pro Gly Trp Leu Ala Leu Ile
    275                 280                 285

Ile Ile Phe Thr Ala Val Phe Val Leu Leu Ser Ala Val Leu Val Arg
    290                 295                 300

Leu Arg Val Val Ser Asn Arg Asn Lys Asn Lys Ala Glu Gly Pro Gln
305                 310                 315                 320

Glu Ala Pro Lys Leu Pro His Lys His Lys Leu Ser Pro His Thr Ile
                325                 330                 335

Leu Gly Arg Phe Phe Gln Asn Trp Gly Thr Arg Val Ala Ser Trp Pro
                340                 345                 350

Leu Thr Val Leu Ala Leu Ser Phe Ile Val Ile Ala Leu Ala Ala
    355                 360                 365

Gly Leu Thr Phe Ile Glu Leu Thr Thr Asp Pro Val Glu Leu Trp Ser
    370                 375                 380

Ala Pro Lys Ser Gln Ala Arg Lys Glu Lys Ser Phe His Asp Glu His
385                 390                 395                 400

Phe Gly Pro Phe Phe Arg Thr Asn Gln Ile Phe Val Thr Ala Arg Asn
                405                 410                 415

Arg Ser Ser Tyr Lys Tyr Asp Ser Leu Leu Leu Gly Ser Lys Asn Phe
                420                 425                 430
```

```
Ser Gly Ile Leu Ser Leu Asp Phe Leu Leu Glu Leu Glu Leu Gln
        435                 440                 445

Glu Arg Leu Arg His Leu Gln Val Trp Ser Pro Glu Ala Glu Arg Asn
    450                 455                 460

Ile Ser Leu Gln Asp Ile Cys Tyr Ala Pro Leu Asn Pro Tyr Asn Thr
465                 470                 475                 480

Ser Leu Ser Asp Cys Cys Val Asn Ser Leu Leu Gln Tyr Phe Gln Asn
                485                 490                 495

Asn Arg Thr Leu Leu Met Leu Thr Ala Asn Gln Thr Leu Asn Gly Gln
            500                 505                 510

Thr Ser Leu Val Asp Trp Lys Asp His Phe Leu Tyr Cys Ala Asn Ala
            515                 520                 525

Pro Leu Thr Phe Lys Asp Gly Thr Ser Leu Ala Leu Ser Cys Met Ala
        530                 535                 540

Asp Tyr Gly Ala Pro Val Phe Pro Phe Leu Ala Val Gly Gly Tyr Gln
545                 550                 555                 560

Gly Thr Asp Tyr Ser Glu Ala Glu Ala Leu Ile Ile Thr Phe Ser Leu
                565                 570                 575

Asn Asn Tyr Pro Ala Asp Asp Pro Arg Met Ala Gln Ala Lys Leu Trp
            580                 585                 590

Glu Glu Ala Phe Leu Lys Glu Met Glu Ser Phe Gln Arg Asn Thr Ser
        595                 600                 605

Asp Lys Phe Gln Val Ala Phe Ser Ala Glu Arg Ser Leu Glu Asp Glu
    610                 615                 620

Ile Asn Arg Thr Thr Ile Gln Asp Leu Pro Val Phe Ala Val Ser Tyr
625                 630                 635                 640

Ile Ile Val Phe Leu Tyr Ile Ser Leu Ala Leu Gly Ser Tyr Ser Arg
                645                 650                 655

Cys Ser Arg Val Ala Val Glu Ser Lys Ala Thr Leu Gly Leu Gly Gly
            660                 665                 670

Val Ile Val Val Leu Gly Ala Val Leu Ala Ala Met Gly Phe Tyr Ser
            675                 680                 685

Tyr Leu Gly Val Pro Ser Ser Leu Val Ile Ile Gln Val Val Pro Phe
        690                 695                 700

Leu Val Leu Ala Val Gly Ala Asp Asn Ile Phe Ile Phe Val Leu Glu
705                 710                 715                 720

Tyr Gln Arg Leu Pro Arg Met Pro Gly Glu Gln Arg Glu Ala His Ile
                725                 730                 735

Gly Arg Thr Leu Gly Ser Val Ala Pro Ser Met Leu Leu Cys Ser Leu
            740                 745                 750

Ser Glu Ala Ile Cys Phe Phe Leu Gly Ala Leu Thr Pro Met Pro Ala
            755                 760                 765

Val Arg Thr Phe Ala Leu Thr Ser Gly Leu Ala Ile Ile Leu Asp Phe
        770                 775                 780

Leu Leu Gln Met Thr Ala Phe Val Ala Leu Leu Ser Leu Asp Ser Lys
785                 790                 795                 800

Arg Gln Glu Ala Ser Arg Pro Asp Val Leu Cys Cys Phe Ser Thr Arg
                805                 810                 815

Lys Leu Pro Pro Pro Lys Glu Lys Glu Gly Leu Leu Leu Arg Phe Phe
            820                 825                 830

Arg Lys Ile Tyr Ala Pro Phe Leu Leu His Arg Phe Ile Arg Pro Val
            835                 840                 845
```

-continued

```
Val Met Leu Leu Phe Leu Thr Leu Phe Gly Ala Asn Leu Tyr Leu Met
    850                 855                 860
Cys Asn Ile Asn Val Gly Leu Asp Gln Glu Leu Ala Leu Pro Lys Asp
865                 870                 875                 880
Ser Tyr Leu Ile Asp Tyr Phe Leu Phe Leu Asn Arg Tyr Leu Glu Val
                    885                 890                 895
Gly Pro Pro Val Tyr Phe Val Thr Thr Ser Gly Phe Asn Phe Ser Ser
                900                 905                 910
Glu Ala Gly Met Asn Ala Thr Cys Ser Ser Ala Gly Cys Lys Ser Phe
                915                 920                 925
Ser Leu Thr Gln Lys Ile Gln Tyr Ala Ser Glu Phe Pro Asp Gln Ser
    930                 935                 940
Tyr Val Ala Ile Ala Ala Ser Ser Trp Val Asp Asp Phe Ile Asp Trp
945                 950                 955                 960
Leu Thr Pro Ser Ser Cys Cys Arg Leu Tyr Ile Arg Gly Pro His
                    965                 970                 975
Lys Asp Glu Phe Cys Pro Ser Thr Asp Thr Ser Phe Asn Cys Leu Lys
                980                 985                 990
Asn Cys Met Asn Arg Thr Leu Gly Pro Val Arg Pro Thr Ala Glu Gln
            995                 1000                1005
Phe His Lys Tyr Leu Pro Trp Phe Leu Asn Asp Pro Pro Asn Ile
    1010                1015                1020
Arg Cys Pro Lys Gly Gly Leu Ala Ala Tyr Arg Thr Ser Val Asn
    1025                1030                1035
Leu Ser Ser Asp Gly Gln Val Ile Ala Ser Gln Phe Met Ala Tyr
    1040                1045                1050
His Lys Pro Leu Arg Asn Ser Gln Asp Phe Thr Glu Ala Leu Arg
    1055                1060                1065
Ala Ser Arg Leu Leu Ala Ala Asn Ile Thr Ala Asp Leu Arg Lys
    1070                1075                1080
Val Pro Gly Thr Asp Pro Asn Phe Glu Val Phe Pro Tyr Thr Ile
    1085                1090                1095
Ser Asn Val Phe Tyr Gln Gln Tyr Leu Thr Val Leu Pro Glu Gly
    1100                1105                1110
Ile Phe Thr Leu Ala Leu Cys Phe Val Pro Thr Phe Val Val Cys
    1115                1120                1125
Tyr Leu Leu Leu Gly Leu Asp Met Cys Ser Gly Ile Leu Asn Leu
    1130                1135                1140
Leu Ser Ile Ile Met Ile Leu Val Asp Thr Ile Gly Leu Met Ala
    1145                1150                1155
Val Trp Gly Ile Ser Tyr Asn Ala Val Ser Leu Ile Asn Leu Val
    1160                1165                1170
Thr Ala Val Gly Met Ser Val Glu Phe Val Ser His Ile Thr Arg
    1175                1180                1185
Ser Phe Ala Val Ser Thr Lys Pro Thr Arg Leu Glu Arg Ala Lys
    1190                1195                1200
Asp Ala Thr Val Phe Met Gly Ser Ala Val Phe Ala Gly Val Ala
    1205                1210                1215
Met Thr Asn Phe Pro Gly Ile Leu Ile Leu Gly Phe Ala Gln Ala
    1220                1225                1230
Gln Leu Ile Gln Ile Phe Phe Arg Leu Asn Leu Leu Ile Thr
    1235                1240                1245
Leu Leu Gly Leu Leu His Gly Leu Val Phe Leu Pro Val Val Leu
```

```
                       1250                 1255                 1260
Ser Tyr Leu Gly Pro Asp Val Asn Gln Ala Leu Val Gln Glu Glu
        1265                 1270                 1275

Lys Leu Ala Ser Glu Ala Ala Val Ala Pro Glu Pro Ser Cys Pro
        1280                 1285                 1290

Gln Tyr Pro Ser Pro Ala Asp Ala Asp Ala Asn Val Asn Tyr Gly
        1295                 1300                 1305

Phe Ala Pro Glu Leu Ala His Gly Ala Asn Ala Ala Arg Ser Ser
        1310                 1315                 1320

Leu Pro Lys Ser Asp Gln Lys Phe
        1325                 1330

<210> SEQ ID NO 3
<211> LENGTH: 3999
<212> TYPE: DNA
<213> ORGANISM: Homo sapiens
<220> FEATURE:
<221> NAME/KEY: CDS
<222> LOCATION: (1)..(3999)
<223> OTHER INFORMATION:

<400> SEQUENCE: 3 atg gcg gag gcc ggc ctg agg ggc tgg ctg ctg tgg gcc ctg ctc ctg      48
Met Ala Glu Ala Gly Leu Arg Gly Trp Leu Leu Trp Ala Leu Leu Leu
1               5                   10                  15 cgc ttg gcc cag agt gag cct tac aca acc atc cac cag cct ggc tac      96
Arg Leu Ala Gln Ser Glu Pro Tyr Thr Thr Ile His Gln Pro Gly Tyr
            20                  25                  30 tgc gcc ttc tat gac gaa tgt ggg aag aac cca gag ctg tct gga agc     144
Cys Ala Phe Tyr Asp Glu Cys Gly Lys Asn Pro Glu Leu Ser Gly Ser
        35                  40                  45 ctc atg aca ctc tcc aac gtg tcc tgc ctg tcc aac acg ccg gcc cgc     192
Leu Met Thr Leu Ser Asn Val Ser Cys Leu Ser Asn Thr Pro Ala Arg
    50                  55                  60 aag atc aca ggt gat cac ctg atc cta tta cag aag atc tgc ccc cgc     240
Lys Ile Thr Gly Asp His Leu Ile Leu Leu Gln Lys Ile Cys Pro Arg
65                  70                  75                  80 ctc tac acc ggc ccc aac acc caa gcc tgc tgc tcc gcc aag cag ctg     288
Leu Tyr Thr Gly Pro Asn Thr Gln Ala Cys Cys Ser Ala Lys Gln Leu
                85                  90                  95 gta tca ctg gaa gcg agt ctg tcg atc acc aag gcc ctc ctc acc cgc     336
Val Ser Leu Glu Ala Ser Leu Ser Ile Thr Lys Ala Leu Leu Thr Arg
            100                 105                 110 tgc cca gcc tgc tct gac aat ttt gtg aac ctg cac tgc cac aac acg     384
Cys Pro Ala Cys Ser Asp Asn Phe Val Asn Leu His Cys His Asn Thr
        115                 120                 125 tgc agc ccc aat cag agc ctc ttc atc aat gtg acc cgc gtg gcc cag     432
Cys Ser Pro Asn Gln Ser Leu Phe Ile Asn Val Thr Arg Val Ala Gln
    130                 135                 140 cta ggg gct gga caa ctc cca gct gtg gtg gcc tat gag gcc ttc tac     480
Leu Gly Ala Gly Gln Leu Pro Ala Val Val Ala Tyr Glu Ala Phe Tyr
145                 150                 155                 160 cag cat agc ttt gcc gag cag agc tat gac tcc tgc agc cgt gtg cgc     528
Gln His Ser Phe Ala Glu Gln Ser Tyr Asp Ser Cys Ser Arg Val Arg
                165                 170                 175 gtc cct gca gct gcc acg ctg gct gtg ggc acc atg tgt ggc gtg tat     576
Val Pro Ala Ala Ala Thr Leu Ala Val Gly Thr Met Cys Gly Val Tyr
            180                 185                 190 ggc tct gcc ctt tgc aat gcc cag cgc tgg ctc aac ttc cag gga gac     624
Gly Ser Ala Leu Cys Asn Ala Gln Arg Trp Leu Asn Phe Gln Gly Asp
```

```
              195                 200                 205
aca ggc aat ggt ctg gcc cca ctg gac atc acc ttc cac ctc ttg gag        672
Thr Gly Asn Gly Leu Ala Pro Leu Asp Ile Thr Phe His Leu Leu Glu
    210                 215                 220 cct ggc cag gcc gtg ggg agt ggg att cag cct ctg aat gag ggg gtt        720
Pro Gly Gln Ala Val Gly Ser Gly Ile Gln Pro Leu Asn Glu Gly Val
225                 230                 235                 240 gca cgt tgc aat gag tcc caa ggt gac gac gtg gcg acc tgc tcc tgc        768
Ala Arg Cys Asn Glu Ser Gln Gly Asp Asp Val Ala Thr Cys Ser Cys
                245                 250                 255 caa gac tgt gct gca tcc tgt cct gcc ata gcc cgc ccc cag gcc ctc        816
Gln Asp Cys Ala Ala Ser Cys Pro Ala Ile Ala Arg Pro Gln Ala Leu
            260                 265                 270 gac tcc acc ttc tac ctg ggc cag atg ccg ggc agt ctg gtc ctc atc        864
Asp Ser Thr Phe Tyr Leu Gly Gln Met Pro Gly Ser Leu Val Leu Ile
        275                 280                 285 atc atc ctc tgc tct gtc ttc gct gtg gtc acc atc ctg ctt gtg gga        912
Ile Ile Leu Cys Ser Val Phe Ala Val Val Thr Ile Leu Leu Val Gly
    290                 295                 300 ttc cgt gtg gcc ccc gcc agg gac aaa agc aag atg gtg gac ccc aag        960
Phe Arg Val Ala Pro Ala Arg Asp Lys Ser Lys Met Val Asp Pro Lys
305                 310                 315                 320 aag ggc acc agc ctc tct gac aag ctc agc ttc tcc acc cac acc ctc       1008
Lys Gly Thr Ser Leu Ser Asp Lys Leu Ser Phe Ser Thr His Thr Leu
                325                 330                 335 ctt ggc cag ttc ttc cag ggc tgg ggc acg tgg gtg gct tcg tgg cct       1056
Leu Gly Gln Phe Phe Gln Gly Trp Gly Thr Trp Val Ala Ser Trp Pro
            340                 345                 350 ctg acc atc ttg gtg cta tct gtc atc ccg gtg gtg gcc ttg gca gcg       1104
Leu Thr Ile Leu Val Leu Ser Val Ile Pro Val Val Ala Leu Ala Ala
        355                 360                 365 ggc ctg gtc ttt aca gaa ctc act acg gac ccc gtg gag ctg tgg tcg       1152
Gly Leu Val Phe Thr Glu Leu Thr Thr Asp Pro Val Glu Leu Trp Ser
    370                 375                 380 gcc ccc aac agc caa gcc cgg agt gag aaa gct ttc cat gac cag cat       1200
Ala Pro Asn Ser Gln Ala Arg Ser Glu Lys Ala Phe His Asp Gln His
385                 390                 395                 400 ttc ggc ccc ttc ttc cga acc aac cag gtg atc ctg acg gct cct aac       1248
Phe Gly Pro Phe Phe Arg Thr Asn Gln Val Ile Leu Thr Ala Pro Asn
                405                 410                 415 cgg tcc agc tac agg tat gac tct ctg ctg ctg ggg ccc aag aac ttc       1296
Arg Ser Ser Tyr Arg Tyr Asp Ser Leu Leu Leu Gly Pro Lys Asn Phe
            420                 425                 430 agc gga atc ctg gac ctg gac ttg ctg ctg gag ctg cta gag ctg cag       1344
Ser Gly Ile Leu Asp Leu Asp Leu Leu Leu Glu Leu Leu Glu Leu Gln
        435                 440                 445 gag agg ctg cgg cac ctc cag gta tgg tcg ccc gaa gca cag cgc aac       1392
Glu Arg Leu Arg His Leu Gln Val Trp Ser Pro Glu Ala Gln Arg Asn
    450                 455                 460 atc tcc ctg cag gac atc tgc tac gcc ccc ctc aat ccg gac aat acc       1440
Ile Ser Leu Gln Asp Ile Cys Tyr Ala Pro Leu Asn Pro Asp Asn Thr
465                 470                 475                 480 agt ctc tac gac tgc tgc atc aac agc ctc ctg cag tat ttc cag aac       1488
Ser Leu Tyr Asp Cys Cys Ile Asn Ser Leu Leu Gln Tyr Phe Gln Asn
                485                 490                 495 aac cgc acg ctc ctg ctg ctc aca gcc aac cag aca ctg atg ggg cag       1536
Asn Arg Thr Leu Leu Leu Leu Thr Ala Asn Gln Thr Leu Met Gly Gln
            500                 505                 510 acc tcc caa gtc gac tgg aag gac cat ttt ctg tac tgt gcc aat gcc       1584
```

-continued

| | | |
|---|---|---|
| Thr Ser Gln Val Asp Trp Lys Asp His Phe Leu Tyr Cys Ala Asn Ala<br>515                 520                 525 | | |
| ccg ctc acc ttc aag gat ggc aca gcc ctg gcc ctg agc tgc atg gct<br>Pro Leu Thr Phe Lys Asp Gly Thr Ala Leu Ala Leu Ser Cys Met Ala<br>530                 535                 540 | 1632 | |
| gac tac ggg gcc cct gtc ttc ccc ttc ctt gcc att ggg ggg tac aaa<br>Asp Tyr Gly Ala Pro Val Phe Pro Phe Leu Ala Ile Gly Gly Tyr Lys<br>545                 550                 555                 560 | 1680 | |
| gga aag gac tat tct gag gca gag gcc ctg atc atg acg ttc tcc ctc<br>Gly Lys Asp Tyr Ser Glu Ala Glu Ala Leu Ile Met Thr Phe Ser Leu<br>                565                 570                 575 | 1728 | |
| aac aat tac cct gcc ggg gac ccc cgt ctg gcc cag gcc aag ctg tgg<br>Asn Asn Tyr Pro Ala Gly Asp Pro Arg Leu Ala Gln Ala Lys Leu Trp<br>                580                 585                 590 | 1776 | |
| gag gag gcc ttc tta gag gaa atg cga gcc ttc cag cgt cgg atg gct<br>Glu Glu Ala Phe Leu Glu Glu Met Arg Ala Phe Gln Arg Arg Met Ala<br>                595                 600                 605 | 1824 | |
| ggc atg ttc cag gtc acg ttc acg gct gag cgc tct ctg gaa gac gag<br>Gly Met Phe Gln Val Thr Phe Thr Ala Glu Arg Ser Leu Glu Asp Glu<br>                610                 615                 620 | 1872 | |
| atc aat cgc acc aca gct gaa gac ctg ccc atc ttt gcc acc agc tac<br>Ile Asn Arg Thr Thr Ala Glu Asp Leu Pro Ile Phe Ala Thr Ser Tyr<br>625                 630                 635                 640 | 1920 | |
| att gtc ata ttc ctg tac atc tct ctg gcc ctg ggc agc tat tcc agc<br>Ile Val Ile Phe Leu Tyr Ile Ser Leu Ala Leu Gly Ser Tyr Ser Ser<br>                645                 650                 655 | 1968 | |
| tgg agc cga gtg atg gtg gac tcc aag gcc acg ctg ggc ctc ggc ggg<br>Trp Ser Arg Val Met Val Asp Ser Lys Ala Thr Leu Gly Leu Gly Gly<br>                660                 665                 670 | 2016 | |
| gtg gcc gtg gtc ctg gga gca gtc atg gct gcc atg ggc ttc ttc tcc<br>Val Ala Val Val Leu Gly Ala Val Met Ala Ala Met Gly Phe Phe Ser<br>                675                 680                 685 | 2064 | |
| tac ttg ggt atc cgc tcc tcc ctg gtc atc ctg caa gtg gtt cct ttc<br>Tyr Leu Gly Ile Arg Ser Ser Leu Val Ile Leu Gln Val Val Pro Phe<br>                690                 695                 700 | 2112 | |
| ctg gtg ctg tcc gtg ggg gct gat aac atc ttc atc ttt gtt ctc gag<br>Leu Val Leu Ser Val Gly Ala Asp Asn Ile Phe Ile Phe Val Leu Glu<br>705                 710                 715                 720 | 2160 | |
| tac cag agg ctg ccc cgg agg cct ggg gag cca cga gag gtc cac att<br>Tyr Gln Arg Leu Pro Arg Arg Pro Gly Glu Pro Arg Glu Val His Ile<br>                725                 730                 735 | 2208 | |
| ggg cga gcc cta ggc agg gtg gct ccc agc atg ctg ttg tgc agc ctc<br>Gly Arg Ala Leu Gly Arg Val Ala Pro Ser Met Leu Leu Cys Ser Leu<br>                740                 745                 750 | 2256 | |
| tct gag gcc atc tgc ttc ttc cta ggg gcc ctg acc ccc atg cca gct<br>Ser Glu Ala Ile Cys Phe Phe Leu Gly Ala Leu Thr Pro Met Pro Ala<br>                755                 760                 765 | 2304 | |
| gtg cgg acc ttt gcc ctg acc tct ggc ctt gca gtg atc ctt gac ttc<br>Val Arg Thr Phe Ala Leu Thr Ser Gly Leu Ala Val Ile Leu Asp Phe<br>                770                 775                 780 | 2352 | |
| ctc ctg cag atg tca gcc ttt gtg gcc ctg ctc tcc ctg gac agc aag<br>Leu Leu Gln Met Ser Ala Phe Val Ala Leu Leu Ser Leu Asp Ser Lys<br>785                 790                 795                 800 | 2400 | |
| agg cag gag gcc tcc cgg ttg gac gtc tgc tgc tgt gtc aag ccc cag<br>Arg Gln Glu Ala Ser Arg Leu Asp Val Cys Cys Cys Val Lys Pro Gln<br>                805                 810                 815 | 2448 | |
| gag ctg ccc ccg cct ggc cag gga gag ggg ctc ctg ctt ggc ttc ttc<br>Glu Leu Pro Pro Pro Gly Gln Gly Glu Gly Leu Leu Leu Gly Phe Phe<br>                820                 825                 830 | 2496 | |

```
caa aag gct tat gcc ccc ttc ctg ctg cac tgg atc act cga ggt gtt    2544
Gln Lys Ala Tyr Ala Pro Phe Leu Leu His Trp Ile Thr Arg Gly Val
            835                 840                 845 gtg ctg ctg ctg ttt ctc gcc ctg ttc gga gtg agc ctc tac tcc atg    2592
Val Leu Leu Leu Phe Leu Ala Leu Phe Gly Val Ser Leu Tyr Ser Met
    850                 855                 860 tgc cac atc agc gtg gga ctg gac cag gag ctg gcc ctg ccc aag gac    2640
Cys His Ile Ser Val Gly Leu Asp Gln Glu Leu Ala Leu Pro Lys Asp
865                 870                 875                 880 tcg tac ctg ctt gac tat ttc ctc ttt ctg aac cgc tac ttc gag gtg    2688
Ser Tyr Leu Leu Asp Tyr Phe Leu Phe Leu Asn Arg Tyr Phe Glu Val
                885                 890                 895 ggg gcc ccg gtg tac ttt gtt acc acc ttg ggc tac aac ttc tcc agc    2736
Gly Ala Pro Val Tyr Phe Val Thr Thr Leu Gly Tyr Asn Phe Ser Ser
            900                 905                 910 gag gct ggg atg aat gcc atc tgc tcc agt gca ggc tgc aac aac ttc    2784
Glu Ala Gly Met Asn Ala Ile Cys Ser Ser Ala Gly Cys Asn Asn Phe
        915                 920                 925 tcc ttc acc cag aag atc cag tat gcc aca gag ttc cct gag cag tct    2832
Ser Phe Thr Gln Lys Ile Gln Tyr Ala Thr Glu Phe Pro Glu Gln Ser
930                 935                 940 tac ctg gcc atc cct gcc tcc tcc tgg gtg gat gac ttc att gac tgg    2880
Tyr Leu Ala Ile Pro Ala Ser Ser Trp Val Asp Asp Phe Ile Asp Trp
945                 950                 955                 960 ctg acc ccg tcc tcc tgc tgc cgc ctt tat ata tct ggc ccc aat aag    2928
Leu Thr Pro Ser Ser Cys Cys Arg Leu Tyr Ile Ser Gly Pro Asn Lys
                965                 970                 975 gac aag ttc tgc ccc tcg acc gtc aac tct ctg aac tgc cta aag aac    2976
Asp Lys Phe Cys Pro Ser Thr Val Asn Ser Leu Asn Cys Leu Lys Asn
            980                 985                 990 tgc atg agc atc acg atg ggc tct gtg agg ccc tcg gtg gag cag ttc    3024
Cys Met Ser Ile Thr Met Gly Ser Val Arg Pro Ser Val Glu Gln Phe
        995                 1000                1005 cat aag tat ctt ccc tgg ttc ctg aac gac cgg ccc aac atc aaa       3069
His Lys Tyr Leu Pro Trp Phe Leu Asn Asp Arg Pro Asn Ile Lys
1010                1015                1020 tgt ccc aaa ggc ggc ctg gca gca tac agc acc tct gtg aac ttg       3114
Cys Pro Lys Gly Gly Leu Ala Ala Tyr Ser Thr Ser Val Asn Leu
    1025                1030                1035 act tca gat ggc cag gtt tta gcc tcc agg ttc atg gcc tat cac       3159
Thr Ser Asp Gly Gln Val Leu Ala Ser Arg Phe Met Ala Tyr His
1040                1045                1050 aag ccc ctg aaa aac tca cag gat tac aca gaa gct ctg cgg gca       3204
Lys Pro Leu Lys Asn Ser Gln Asp Tyr Thr Glu Ala Leu Arg Ala
    1055                1060                1065 gct cga gag ctg gca gcc aac atc act gct gac ctg cgg aaa gtg       3249
Ala Arg Glu Leu Ala Ala Asn Ile Thr Ala Asp Leu Arg Lys Val
1070                1075                1080 cct gga aca gac ccg gct ttt gag gtc ttc ccc tac acg atc acc       3294
Pro Gly Thr Asp Pro Ala Phe Glu Val Phe Pro Tyr Thr Ile Thr
    1085                1090                1095 aat gtg ttt tat gag cag tac ctg acc atc ctc cct gag ggg ctc       3339
Asn Val Phe Tyr Glu Gln Tyr Leu Thr Ile Leu Pro Glu Gly Leu
1100                1105                1110 ttc atg ctc agc ctc tgc ctt gtg ccc acc ttc gct gtc tcc tgc       3384
Phe Met Leu Ser Leu Cys Leu Val Pro Thr Phe Ala Val Ser Cys
    1115                1120                1125 ctc ctg ctg ggc ctg gac ctg cgc tcc ggc ctc ctc aac ctg ctc       3429
Leu Leu Leu Gly Leu Asp Leu Arg Ser Gly Leu Leu Asn Leu Leu
1130                1135                1140
```

| | | | | | | | | | | | | |
|---|---|---|---|---|---|---|---|---|---|---|---|---|
| tcc | att | gtc | atg | atc | ctc | gtg | gac | act | gtc | ggc | ttc | atg gcc ctg | 3474 |
| Ser | Ile | Val | Met | Ile | Leu | Val | Asp | Thr | Val | Gly | Phe | Met Ala Leu | |
| | 1145 | | | | 1150 | | | | | 1155 | | | |
| tgg | gac | atc | agt | tac | aat | gct | gtg | tcc | ctc | atc | aac | ctg gtc tcg | 3519 |
| Trp | Asp | Ile | Ser | Tyr | Asn | Ala | Val | Ser | Leu | Ile | Asn | Leu Val Ser | |
| 1160 | | | | | 1165 | | | | | 1170 | | | |
| gcg | gtg | ggc | atg | tct | gtg | gag | ttt | gtg | tcc | cac | att | acc cgc tcc | 3564 |
| Ala | Val | Gly | Met | Ser | Val | Glu | Phe | Val | Ser | His | Ile | Thr Arg Ser | |
| 1175 | | | | | 1180 | | | | | 1185 | | | |
| ttt | gcc | atc | agc | acc | aag | ccc | acc | tgg | ctg | gag | agg | gcc aaa gag | 3609 |
| Phe | Ala | Ile | Ser | Thr | Lys | Pro | Thr | Trp | Leu | Glu | Arg | Ala Lys Glu | |
| 1190 | | | | | 1195 | | | | | 1200 | | | |
| gcc | acc | atc | tct | atg | gga | agt | gcg | gtg | ttt | gca | ggt | gtg gcc atg | 3654 |
| Ala | Thr | Ile | Ser | Met | Gly | Ser | Ala | Val | Phe | Ala | Gly | Val Ala Met | |
| 1205 | | | | | 1210 | | | | | 1215 | | | |
| acc | aac | ctg | cct | ggc | atc | ctt | gtc | ctg | ggc | ctc | gcc | aag gcc cag | 3699 |
| Thr | Asn | Leu | Pro | Gly | Ile | Leu | Val | Leu | Gly | Leu | Ala | Lys Ala Gln | |
| 1220 | | | | | 1225 | | | | | 1230 | | | |
| ctc | att | cag | atc | ttc | ttc | ttc | cgc | ctc | aac | ctc | ctg | atc act ctg | 3744 |
| Leu | Ile | Gln | Ile | Phe | Phe | Phe | Arg | Leu | Asn | Leu | Leu | Ile Thr Leu | |
| 1235 | | | | | 1240 | | | | | 1245 | | | |
| ctg | ggc | ctg | ctg | cat | ggc | ttg | gtc | ttc | ctg | ccc | gtc | atc ctc agc | 3789 |
| Leu | Gly | Leu | Leu | His | Gly | Leu | Val | Phe | Leu | Pro | Val | Ile Leu Ser | |
| 1250 | | | | | 1255 | | | | | 1260 | | | |
| tac | gtg | ggg | cct | gac | gtt | aac | ccg | gct | ctg | gca | ctg | gag cag aag | 3834 |
| Tyr | Val | Gly | Pro | Asp | Val | Asn | Pro | Ala | Leu | Ala | Leu | Glu Gln Lys | |
| 1265 | | | | | 1270 | | | | | 1275 | | | |
| cgg | gct | gag | gag | gcg | gtg | gca | gca | gtc | atg | gtg | gcc | tct tgc cca | 3879 |
| Arg | Ala | Glu | Glu | Ala | Val | Ala | Ala | Val | Met | Val | Ala | Ser Cys Pro | |
| 1280 | | | | | 1285 | | | | | 1290 | | | |
| aat | cac | ccc | tcc | cga | gtc | tcc | aca | gct | gac | aac | atc | tat gtc aac | 3924 |
| Asn | His | Pro | Ser | Arg | Val | Ser | Thr | Ala | Asp | Asn | Ile | Tyr Val Asn | |
| 1295 | | | | | 1300 | | | | | 1305 | | | |
| cac | agc | ttt | gaa | ggt | tct | atc | aaa | ggt | gct | ggt | gcc | atc agc aac | 3969 |
| His | Ser | Phe | Glu | Gly | Ser | Ile | Lys | Gly | Ala | Gly | Ala | Ile Ser Asn | |
| 1310 | | | | | 1315 | | | | | 1320 | | | |
| ttc | ttg | ccc | aac | aat | ggg | cgg | cag | ttc | tga | | | | 3999 |
| Phe | Leu | Pro | Asn | Asn | Gly | Arg | Gln | Phe | | | | | |
| 1325 | | | | | 1330 | | | | | | | | |

<210> SEQ ID NO 4
<211> LENGTH: 1332
<212> TYPE: PRT
<213> ORGANISM: Homo sapiens

<400> SEQUENCE: 4

Met Ala Glu Ala Gly Leu Arg Gly Trp Leu Leu Trp Ala Leu Leu Leu
1               5                   10                  15

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
        35                  40                  45

Leu Met Thr Leu Ser Asn Val Ser Cys Leu Ser Asn Thr Pro Ala Arg
    50                  55                  60

Lys Ile Thr Gly Asp His Leu Ile Leu Leu Gln Lys Ile Cys Pro Arg
65                  70                  75                  80

Leu Tyr Thr Gly Pro Asn Thr Gln Ala Cys Cys Ser Ala Lys Gln Leu
                85                  90                  95

```
Val Ser Leu Glu Ala Ser Leu Ser Ile Thr Lys Ala Leu Leu Thr Arg
            100                 105                 110

Cys Pro Ala Cys Ser Asp Asn Phe Val Asn Leu His Cys His Asn Thr
            115                 120                 125

Cys Ser Pro Asn Gln Ser Leu Phe Ile Asn Val Thr Arg Val Ala Gln
130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val Arg
                165                 170                 175

Val Pro Ala Ala Ala Thr Leu Ala Val Gly Thr Met Cys Gly Val Tyr
            180                 185                 190

Gly Ser Ala Leu Cys Asn Ala Gln Arg Trp Leu Asn Phe Gln Gly Asp
            195                 200                 205

Thr Gly Asn Gly Leu Ala Pro Leu Asp Ile Thr Phe His Leu Leu Glu
    210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Asp Val Ala Thr Cys Ser Cys
                245                 250                 255

Gln Asp Cys Ala Ala Ser Cys Pro Ala Ile Ala Arg Pro Gln Ala Leu
            260                 265                 270

Asp Ser Thr Phe Tyr Leu Gly Gln Met Pro Gly Ser Leu Val Leu Ile
            275                 280                 285

Ile Ile Leu Cys Ser Val Phe Ala Val Val Thr Ile Leu Leu Val Gly
    290                 295                 300

Phe Arg Val Ala Pro Ala Arg Asp Lys Ser Lys Met Val Asp Pro Lys
305                 310                 315                 320

Lys Gly Thr Ser Leu Ser Asp Lys Leu Ser Phe Ser Thr His Thr Leu
                325                 330                 335

Leu Gly Gln Phe Phe Gln Gly Trp Gly Thr Trp Val Ala Ser Trp Pro
            340                 345                 350

Leu Thr Ile Leu Val Leu Ser Val Ile Pro Val Val Ala Leu Ala Ala
            355                 360                 365

Gly Leu Val Phe Thr Glu Leu Thr Thr Asp Pro Val Glu Leu Trp Ser
    370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Gly Pro Lys Asn Phe
            420                 425                 430

Ser Gly Ile Leu Asp Leu Asp Leu Leu Glu Leu Glu Leu Gln
            435                 440                 445

Glu Arg Leu Arg His Leu Gln Val Trp Ser Pro Glu Ala Gln Arg Asn
    450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Lys Asp His Phe Leu Tyr Cys Ala Asn Ala
```

```
                515                 520                 525
Pro Leu Thr Phe Lys Asp Gly Thr Ala Leu Ala Leu Ser Cys Met Ala
    530                 535                 540
Asp Tyr Gly Ala Pro Val Phe Pro Phe Leu Ala Ile Gly Gly Tyr Lys
545                 550                 555                 560
Gly Lys Asp Tyr Ser Glu Ala Glu Ala Leu Ile Met Thr Phe Ser Leu
                565                 570                 575
Asn Asn Tyr Pro Ala Gly Asp Pro Arg Leu Ala Gln Ala Lys Leu Trp
            580                 585                 590
Glu Glu Ala Phe Leu Glu Met Arg Ala Phe Gln Arg Arg Met Ala
    595                 600                 605
Gly Met Phe Gln Val Thr Phe Thr Ala Glu Arg Ser Leu Glu Asp Glu
    610                 615                 620
Ile Asn Arg Thr Thr Ala Glu Asp Leu Pro Ile Phe Ala Thr Ser Tyr
625                 630                 635                 640
Ile Val Ile Phe Leu Tyr Ile Ser Leu Ala Leu Gly Ser Tyr Ser Ser
                645                 650                 655
Trp Ser Arg Val Met Val Asp Ser Lys Ala Thr Leu Gly Leu Gly Gly
            660                 665                 670
Val Ala Val Leu Gly Ala Val Met Ala Ala Met Gly Phe Phe Ser
    675                 680                 685
Tyr Leu Gly Ile Arg Ser Ser Leu Val Ile Leu Gln Val Val Pro Phe
    690                 695                 700
Leu Val Leu Ser Val Gly Ala Asp Asn Ile Phe Ile Phe Val Leu Glu
705                 710                 715                 720
Tyr Gln Arg Leu Pro Arg Arg Pro Gly Glu Pro Arg Glu Val His Ile
            725                 730                 735
Gly Arg Ala Leu Gly Arg Val Ala Pro Ser Met Leu Leu Cys Ser Leu
            740                 745                 750
Ser Glu Ala Ile Cys Phe Phe Leu Gly Ala Leu Thr Pro Met Pro Ala
        755                 760                 765
Val Arg Thr Phe Ala Leu Thr Ser Gly Leu Ala Val Ile Leu Asp Phe
    770                 775                 780
Leu Leu Gln Met Ser Ala Phe Val Ala Leu Leu Ser Leu Asp Ser Lys
785                 790                 795                 800
Arg Gln Glu Ala Ser Arg Leu Asp Val Cys Cys Val Lys Pro Gln
            805                 810                 815
Glu Leu Pro Pro Pro Gly Gln Gly Glu Gly Leu Leu Leu Gly Phe Phe
            820                 825                 830
Gln Lys Ala Tyr Ala Pro Phe Leu Leu His Trp Ile Thr Arg Gly Val
        835                 840                 845
Val Leu Leu Leu Phe Leu Ala Leu Phe Gly Val Ser Leu Tyr Ser Met
    850                 855                 860
Cys His Ile Ser Val Gly Leu Asp Gln Glu Leu Ala Leu Pro Lys Asp
865                 870                 875                 880
Ser Tyr Leu Leu Asp Tyr Phe Leu Phe Leu Asn Arg Tyr Phe Glu Val
                885                 890                 895
Gly Ala Pro Val Tyr Phe Val Thr Thr Leu Gly Tyr Asn Phe Ser Ser
            900                 905                 910
Glu Ala Gly Met Asn Ala Ile Cys Ser Ser Ala Gly Cys Asn Asn Phe
        915                 920                 925
Ser Phe Thr Gln Lys Ile Gln Tyr Ala Thr Glu Phe Pro Glu Gln Ser
    930                 935                 940
```

-continued

```
Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
                965                 970                 975

Asp Lys Phe Cys Pro Ser Thr Val Asn Ser Leu Asn Cys Leu Lys Asn
                980                 985                 990

Cys Met Ser Ile Thr Met Gly Ser Val Arg Pro Ser Val Glu Gln Phe
            995                 1000                1005

His Lys Tyr Leu Pro Trp Phe Leu Asn Asp Arg Pro Asn Ile Lys
        1010                1015                1020

Cys Pro Lys Gly Gly Leu Ala Ala Tyr Ser Thr Ser Val Asn Leu
        1025                1030                1035

Thr Ser Asp Gly Gln Val Leu Ala Ser Arg Phe Met Ala Tyr His
        1040                1045                1050

Lys Pro Leu Lys Asn Ser Gln Asp Tyr Thr Glu Ala Leu Arg Ala
        1055                1060                1065

Ala Arg Glu Leu Ala Ala Asn Ile Thr Ala Asp Leu Arg Lys Val
        1070                1075                1080

Pro Gly Thr Asp Pro Ala Phe Glu Val Phe Pro Tyr Thr Ile Thr
        1085                1090                1095

Asn Val Phe Tyr Glu Gln Tyr Leu Thr Ile Leu Pro Glu Gly Leu
        1100                1105                1110

Phe Met Leu Ser Leu Cys Leu Val Pro Thr Phe Ala Val Ser Cys
        1115                1120                1125

Leu Leu Leu Gly Leu Asp Leu Arg Ser Gly Leu Leu Asn Leu Leu
        1130                1135                1140

Ser Ile Val Met Ile Leu Val Asp Thr Val Gly Phe Met Ala Leu
        1145                1150                1155

Trp Asp Ile Ser Tyr Asn Ala Val Ser Leu Ile Asn Leu Val Ser
        1160                1165                1170

Ala Val Gly Met Ser Val Glu Phe Val Ser His Ile Thr Arg Ser
        1175                1180                1185

Phe Ala Ile Ser Thr Lys Pro Thr Trp Leu Glu Arg Ala Lys Glu
        1190                1195                1200

Ala Thr Ile Ser Met Gly Ser Ala Val Phe Ala Gly Val Ala Met
        1205                1210                1215

Thr Asn Leu Pro Gly Ile Leu Val Leu Gly Leu Ala Lys Ala Gln
        1220                1225                1230

Leu Ile Gln Ile Phe Phe Phe Arg Leu Asn Leu Leu Ile Thr Leu
        1235                1240                1245

Leu Gly Leu Leu His Gly Leu Val Phe Leu Pro Val Ile Leu Ser
        1250                1255                1260

Tyr Val Gly Pro Asp Val Asn Pro Ala Leu Ala Leu Glu Gln Lys
        1265                1270                1275

Arg Ala Glu Glu Ala Val Ala Ala Val Met Val Ala Ser Cys Pro
        1280                1285                1290

Asn His Pro Ser Arg Val Ser Thr Ala Asp Asn Ile Tyr Val Asn
        1295                1300                1305

His Ser Phe Glu Gly Ser Ile Lys Gly Ala Gly Ala Ile Ser Asn
        1310                1315                1320

Phe Leu Pro Asn Asn Gly Arg Gln Phe
        1325                1330
```

<210> SEQ ID NO 5
<211> LENGTH: 885
<212> TYPE: DNA
<213> ORGANISM: Rattus sp.

<400> SEQUENCE: 5

| | | | | | |
|---|---|---|---|---|---|
| ccacgcgtcc | gcacctgcaa | gtgtggtccc | ctgaggcaga | gcgcaacatc | tccctccagg | 60 |
| acatctgcta | tgccccctc | aacccatata | acaccagcct | ctccgactgc | tgtgtcaaca | 120 |
| gcctccttca | gtacttccag | aacaaccgca | ccctcctgat | gctcacggcc | aaccagactc | 180 |
| tgaatggcca | gacctccctg | gtggactgga | aggaccattt | cctctactgt | gcaaatgccc | 240 |
| ctctcacgtt | caaagatggc | acgtctctgg | ccctgagctg | catggctgac | tacggggctc | 300 |
| ctgtcttccc | cttccttgct | gttggggat | accaaggcac | ggactattcc | gaggcagaag | 360 |
| cgctgatcat | aaccttctct | ctcaataact | accccgctga | tgatccccgc | atggcccagg | 420 |
| ccaagctctg | ggaggaggct | ttcttgaagg | aaatggaatc | cttccagagg | aacacaagtg | 480 |
| acaagttcca | ggttgcgttc | tcagctgagc | gctctctgga | ggatgagatc | aaccgcacca | 540 |
| ccatccagga | cctgcctgtc | tttgccgtca | gctacattat | cgtcttcctg | tacatctccc | 600 |
| tggccctggg | cagctactcc | agatgcagcc | gagtagcggt | ggagtccaag | gctactctgg | 660 |
| gcctaggtgg | ggtgatagtg | tgctgggagc | agttctggct | tgcatggggc | ttctaactcc | 720 |
| tacctgggtg | tcccctcttc | tctggttatc | atccaagtgg | tacctttcct | ggtgcttaag | 780 |
| ctgtgggagc | tggacacatc | tacatcctag | acttgagtac | cagaggtacc | taggaagccg | 840 |
| cggaacagcg | aaaaggacac | attgggcgca | ccctgggcat | gtggc | | 885 |

<210> SEQ ID NO 6
<211> LENGTH: 458
<212> TYPE: DNA
<213> ORGANISM: Rattus sp.

<400> SEQUENCE: 6

| | | | | | |
|---|---|---|---|---|---|
| gaccagatgt | taaccaagct | ctggtacagg | aggagaaact | agccagcgag | gcagcagtgg | 60 |
| ccccagagcc | ttcttgccca | cagtacccct | ccctgctga | tgcggatgcc | aatgttaact | 120 |
| acggctttgc | cccagaactt | gcccacggag | ctaatgctgc | tagaagctct | ttgcccaaaa | 180 |
| gtgaccaaaa | gttctaatgg | agtaggagct | tgtccatgct | tctgctgatg | agggatcatg | 240 |
| aaggtcttcc | ctctggttgt | cctcaaggcc | tgggggagg | ttgttcagag | aaaaatggct | 300 |
| ggcattcctg | ccacgaggca | accggcagct | tggcactgac | tccttggtct | cataggtccc | 360 |
| taaggcttgg | tcagattact | cctcatggag | agactatctt | aagtatctaa | gctatcgatt | 420 |
| gggatgcatc | gctgttcatt | aaaaaggcta | tggctatg | | | 458 |

<210> SEQ ID NO 7
<211> LENGTH: 896
<212> TYPE: DNA
<213> ORGANISM: Rattus sp.

<400> SEQUENCE: 7

| | | | | | |
|---|---|---|---|---|---|
| ccacgcgtcc | gcagtttcat | aagtacctgc | cctggttcct | gaatgatccg | cccaatatca | 60 |
| gatgtcccaa | aggggtcta | gcagcgtata | gaacgtctgt | gaatttgagc | tcagatggcc | 120 |
| aggttatagc | ctcccagttc | atggcctacc | acaagccctt | aaggaactca | caggacttca | 180 |
| cagaagctct | ccgggcgtcc | cggttgctag | cagccaacat | cacagctgac | ctacggaagg | 240 |
| tgcctgggac | agatccaaac | tttgaggtct | tcccttacac | gatctccaac | gtgttctacc | 300 |

```
agcaatacct gacggtcctt cctgagggaa tcttcaccct tgctctttgc tttgtgccca    360
cctttgttgt ctgctacctc ctactgggcc tggacatgtg ctcagggatc ctcaacctac    420
tctccatcat tatgattctc gtggacacca ttggcctcat ggctgtgtgg ggtatcagct    480
ataatgcggt atccctcatc aaccttgtca cggcagtggg catgtctgtg gagtttgtgt    540
cccacatcac tcggtccttt gcttgtaagc accaagccta cccggctgga gagggctaaa    600
agatgctact gtcttcatgg gcagtgcggt gtttgctgga gtggccatga ccaacttccc    660
aggcatcctc atcttggggg ctttgcccca agcccaggct tattcagatc ttcttcttcc    720
gcctcaacct tctgatcacc tttgctgggg tctgctgcat ggctggtctt cctgcccggt    780
ttgtcctcag ctatctggga ccagatgtaa ccaaggctct gctacccgga ggagaaacta    840
gccagcgagg gcagcagtgg ccccagagac ttcttgccca caagtaccct tccctg        896

<210> SEQ ID NO 8
<211> LENGTH: 3124
<212> TYPE: DNA
<213> ORGANISM: Rattus sp.

<400> SEQUENCE: 8
tgcaagtgtg gtcccctgag gcagagcgca acatctccct ccaggacatc tgctatgccc     60
ccctcaaccc atataacacc agcctctccg actgctgtgt caacagcctc cttcagtact    120
tccagaacaa ccgcaccctc ctgatgctca cggccaacca gactctgaat ggccagacct    180
ccctggtgga ctggaaggac catttcctct actgtgcaaa tgcccctctc acgttcaaag    240
atggcacgtc tctggccctg agctgcatgg ctgactacgg ggctcctgtc ttccccttcc    300
ttgctgttgg gggataccaa ggcacggact attccgaggc agaagcgctg atcataacct    360
tctctctcaa taactacccc gctgatgatc cccgcatggc ccaggccaag ctctgggagg    420
aggctttctt gaaggaaatg gaatccttcc agaggaacac aagtgacaag ttccaggttg    480
cgttctcagc tgagcgctct ctggaggatg agatcaaccg caccaccatc caggacctgc    540
ctgtctttgc cgtcagctac attatcgtct cctgtacact ctccctggcc ctgggcagct    600
actccagatg cagccgagta gcggtggagt ccaaggctac tctgggccta ggtggggtga    660
ttgttgtgct gggagcagtt ctggctgcca tgggcttcta ctcctacctg ggtgtccccT    720
cttctctggt tatcatccaa gtggtacctt tcctggtgct agctgtggga gctgacaaca    780
tcttcatctt tgttcttgag taccagaggc tacctaggat gcctggggaa cagcgagagg    840
ctcacattgg ccgcacccTg ggcagtgtgg cccccagcat gctgctgtgc agcctctctg    900
aggccatctg cttctttcta ggggccctga ccccatgcc agctgtgagg accttcgcct    960
tgacctctgg cttagcaatt atcctcgact tcctgctcca gatgactgcc tttgtggccc    1020
tgctctccct ggatagcaag aggcaggagg cctctcgccc ggatgtctta tgctgctttt    1080
caacccggaa gctgccccca cctaaagaaa agaaggcct cttactccgc ttcttccgca    1140
agatatacgc tccttttcctg ctgcacagat tcatccgccc tgttgtgatg ctgctgtttc    1200 tgacccctgtt tggagcaaat ctctacttaa tgtgcaacat caacgtgggg ctagaccagg    1260
agctggctct gccaaggac tcgtacttga tagactactt cctctttctg aaccgatacc    1320
ttgaagtggg gcctccagtg tactttgtca ccacctcggg cttcaacttc tccagcgagg    1380
caggcatgaa cgccacttgc tctagcgcag gctgtaagag cttctcccta acccagaaaa    1440
tccagtatgc cagtgaattc cctgaccagt cttacgtggc tattgctgca tcctcctggg    1500
```

-continued

```
tagatgactt catcgactgg ctgaccccgt cctcctcctg ctgtcgcctt tatatacgtg    1560
gcccccataa ggatgagttc tgtccctcaa cggatacttc cttcaactgc ttaaaaaact    1620
gcatgaaccg cactctgggt cctgtgaggc ccacagcgga acagtttcat aagtacctgc    1680
cctggttcct gaatgatccg cccaatatca gatgtcccaa aggggtcta gcagcgtata     1740 gaacgtctgt gaatttgagc tcagatggca aggttatagc ctcccagttc atggcctacc    1800
acaagcccTt aaggaactca caggacttca cagaagctct ccgggcgtcc cggttgctag    1860
cagccaacat cacagctgac ctacggaagg tgcctgggac agatccaaac tttgaggtct    1920
tcccttacac gatctccaac gtgttctacc agcaatacct gacggtcctt cctgagggaa    1980
tcttcaccct tgctctttgc tttgtgccca cctttgttgt ctgctacctc ctactgggcc    2040
tggacatgtg ctcagggatc ctcaacctac tctccatcat tatgattctc gtggacacca    2100
ttggcctcat ggctgtgtgg ggtatcagct ataatgcggt atccctcatc aaccttgtca    2160
cggcagtggg catgtctgtg gagtttgtgt cccacatcac tcggtccttt gctgtaagca    2220
ccaagcctac ccggctggag agggctaaag atgctactgt cttcatgggc agtgcggtgt    2280
ttgctggagt ggccatgacc aacttcccag gcatcctcat cttgggcttt gcccaagccc    2340
agcttattca gatcttcttc ttccgcctca accttctgat caccttgctg ggtctgctgc    2400
atggcctggt cttcctgccg gttgtcctca gctatctggg accagatgtt aaccaagctc    2460
tggtacagga ggagaaacta gccagcgagg cagcagtggc cccagagcct tcttgcccac    2520 agtaccctc ccctgctgat gcggatgcca atgttaacta cggctttgcc ccagaacttg     2580
cccacggagc taatgctgct agaagctctt tgcccaaaag tgaccaaaag ttctaatgga    2640
gtaggagctt gtccatgctt cttgctgatg agggatcatg aagtcttcc ctctggttgt     2700 cctcaaggcc tgggggagg ttgtttcaga gaaaaatggc tggcattcct gccacgaggc     2760
aaccggcagc attggcactg acctccttgc tctcataggt ccctaaggcc ttggtcagat    2820
tacctcctcc atggagagac tatcttaagt atcttaagta tcgtatggga tgcatcgcct    2880
gtcaattaaa aaggctatgg cctatggctc aggcagggcc atccggaaga agagaggatt    2940
ctgggataaa gccaggtggg agattcgcct ggggaaaatg tgacaatggt tcctgagcat    3000
gggcaatcag ccatgtggca gaatgtaaat taatataaat gggttgtctt aagttatgat    3060
tctagctggg gaggagccta gctgtgtagc caagatattt gtaaatataa aaaaaaaaaa    3120
aaaa                                                                 3124
```

<210> SEQ ID NO 9
<211> LENGTH: 4484
<212> TYPE: DNA
<213> ORGANISM: Rattus sp.

<400> SEQUENCE: 9

```
atggcagctg cctggctggg atggctgctc tgggccctgc cctgagcgc ggcccagggt       60 gagctataca cacccaaaca cgaagctggg gtctgcacct tttacgaaga gtgcgggaaa    120
aacccagagc tctctggagg cctcacgtca ctatccaatg tatcctgcct gtctaacacc    180
ccggcccgcc acgtcacggg tgaacacctg gctcttctcc agcgcatctg tccccgcctg    240
tacaacggcc ccaataccac ttttgcctgt tgctctacca gcagctgct gtccttagaa     300 agcagcatgt ccatcaccaa ggcccttctc acgcgctgcc cggcctgctc tgacaatttt    360
gtgagcttac actgccacaa cacttgcagc cctgaccaga gcctcttcat caacgtcacc    420
cgggtggttg agcggggcgc tggagagcct cctgccgtgg tggcctatga ggccttttat    480
```

```
cagcgcagct tgctgagaa ggcctatgag tcctgcagcc aggtgcgcat ccctgcggcc    540
gcttccttgg ccgtgggcag catgtgtgga gtgtatggct ccgccctctg caatgctcag    600
cgctggctca acttccaagg agacacaggg aatggcctgg ctccgctgga tatcaccttc    660
cacctcttgg agcctggcca ggccctaccg gatgggatcc agccactgaa tgggaagatc    720
gcaccctgca acgagtctca gggtgatgac tcagcagtct gctcctgcca ggactgtgcg    780
gcgtcctgcc ctgtcatccc tccgcccgag gccttgcgcc cttccttcta catgggtcgc    840
atgccaggct ggctggccct catcatcatc ttcactgctg tctttgtgtt gctctctgca    900
gtccttgtgc gtctccgagt ggtttccaac aggaacaaga acaaggcaga aggcccccag    960
gaagccccca actccctcta taagcacaaa ctctcacccc ataccatcct gggccggttc   1020
ttccagaact ggggcacaag ggtggcctcg tggccactca ccgtcttagc actgtccttc   1080
atcgttgtga tagccttagc agcaggcctg acctttattg aactcaccac agaccctgtg   1140
gaactgtggt cggcccccaa gagccaggcc cggaaagaga agtctttcca tgatgagcat   1200
ttcggcccct tctttcgaac caaccagatt ttcgtgacag ctcggaacag gtccagctac   1260
aagtacgact ccctactgct agggtccaag aacttcagtg gatcctgtc cctggacttc   1320
ctgctggagc tgctggagct tcaggagagg cttcgacacc tgcaagtgtg gtcccctgag   1380
gcagagcgca acatctccct ccaggacatc tgctatgccc ccctcaaccc atataacacc   1440
agcctctccg actgctgtgt caacagcctc cttcagtact ccagaacaa ccgcaccctc   1500
ctgatgctca cggccaacca gactctgaat ggccagacct ccctggtgga ctggaaggac   1560
catttcctct actgtgcaaa tgcccctctc acgttcaaag atggcacgtc tctggccctg   1620
agctgcatgg ctgactacgg ggctcctgtc ttccccttcc ttgctgttgg gggataccaa   1680
ggcacggact attccgaggc agaagcgctg atcataacct tctctctcaa taactacccc   1740
gctgatgatc cccgcatggc ccaggccaag ctctgggagg aggctttctt gaaggaaatg   1800
gaatccttcc agaggaacac aagtgacaag ttccaggttg cgttctcagc tgagcgctct   1860
ctggaggatg agatcaaccg caccaccatc caggacctgc ctgtctttgc cgtcagctac   1920
attatcgtct tcctgtacat ctccctggcc ctgggcagct actccagatg cagccgagta   1980
gcggtggagt ccaaggctac tctgggccta ggtggggtga ttgttgtgct gggagcagtt   2040
ctggctgcca tgggcttcta ctcctacctg ggtgtcccct cttctctggt tatcatccaa   2100
gtggtacctt tcctggtgct agctgtggga ctgacaacaa tcttcatctt tgttcttgag   2160
taccagaggc tacctaggat gcctggggaa cagcgagagg ctcacattgg ccgcacccgg   2220
ggcagtgtgg ccccagcat gctgctgtgc agcctctctg aggccatctg cttctttcta   2280
ggggccctga ccccatgcc agctgtgagg accttcgcct tgacctctgg cttagcaatt   2340
atcctcgact tcctgctcca gatgactgcc tttgtggccc tgctctccct ggatagcaag   2400
aggcaggagg cctctcgccc ggatgtctta tgctgctttt caacccggaa gctgccccca   2460
cctaaagaaa aagaaggcct cttactccgc ttcttccgca agatatacgc tcctttcctg   2520
ctgcacagat tcatccgccc tgttgtgatg ctgctgtttc tgacctgtt tggagcaaat   2580
ctctacttaa tgtgcaacat caacgtgggg ctagaccagg agctggctct gcccaaggac   2640
tcgtacttga tagactactt cctctttctg aaccgatacc ttgaagtggg gcctccagtg   2700
tactttgtca ccacctcggg cttcaacttc ccagcgagg caggcatgaa cgccacttgc   2760
tctagcgcag gctgtaagag cttctcccta acccagaaaa tccagtatgc cagtgaattc   2820
```

```
cctgaccagt cttacgtggc tattgctgca tcctcctggg tagatgactt catcgactgg      2880
ctgaccccgt cctcctcctg ctgtcgcctt tatatacgtg gcccccataa ggatgagttc      2940
tgtccctcaa cggatacttc cttcaactgc ttaaaaaact gcatgaaccg cactctgggt      3000
cctgtgaggc ccacagcgga acagtttcat aagtacctgc cctggttcct gaatgatccg      3060
cccaatatca gatgtcccaa aggggtctca gcagcgtata aacgtctgt gaatttgagc       3120 tcagatggcc aggttatagc ctcccagttc atggcctacc acaagccctt aaggaactca      3180
caggacttca cagaagctct ccgggcgtcc cggttgctag cagccaacat cacagctgac      3240
ctacggaagg tgcctgggac agatccaaac tttgaggtct tcccttacac gatctccaac      3300
gtgttctacc agcaatacct gacggtcctt cctgagggaa tcttcaccct tgctctttgc      3360
tttgtgccca cctttgttgt ctgctacctc ctactgggcc tggacatgtg ctcagggatc      3420
ctcaacctac tctccatcat tatgattctc gtggacacca ttggcctcat ggctgtgtgg      3480
ggtatcagct ataatgcggt atccctcatc aaccttgtca cggcagtggg catgtctgtg      3540
gagtttgtgt cccacatcac tcggtccttt gctgtaagca ccaagcctac ccggctggag      3600
agggctaaag atgctactgt cttcatgggc agtgcggtgt ttgctggagt ggccatgacc      3660
aacttcccag gcatcctcat cttgggcttt gcccaagccc agcttattca gatcttcttc      3720
ttccgcctca accttctgat caccttgctg ggtctgctgc atggcctggt cttcctgccg      3780
gttgtcctca gctatctggg accagatgtt aaccaagctc tggtacagga ggagaaacta      3840
gccagcgagg cagcagtggc cccagagcct tcttgcccac agtaccccctc ccctgctgat      3900 gcggatgcca atgttaacta cggctttgcc ccagaacttg cccacggagc taatgctgct      3960
agaagctctt tgcccaaaag tgaccaaaag ttctaatgga gtaggagctt gtccatgctt      4020
cttgctgatg agggatcatg aaggtcttcc ctctggttgt cctcaaggcc tgggggagg       4080 ttgtttcaga gaaaaatggc tggcattcct gccacgaggc aaccggcagc attggcactg      4140
acctccttgc tctcataggt ccctaaggcc ttggtcagat tacctcctcc atggagagac      4200
tatcttaagt atcttaagta tcgtatggga tgcatcgcct gtcaattaaa aaggctatgg      4260
cctatggctc aggcagggcc atccggaaga agagaggatt ctgggataaa gccaggtggg      4320
agattcgcct ggggaaaatg tgacaatggt tcctgagcat gggcaatcag ccatgtggca      4380
gaatgtaaat taatataaat gggttgtctt aagttatgat tctagctggg gaggagccta      4440
gctgtgtagc caagatattt gtaaatataa aaaaaaaaa aaaa                       4484
```

<210> SEQ ID NO 10
<211> LENGTH: 3993
<212> TYPE: DNA
<213> ORGANISM: Rattus sp.
<220> FEATURE:
<221> NAME/KEY: misc_feature
<222> LOCATION: (1)..(3993)
<223> OTHER INFORMATION: n is g or a or t or c

<400> SEQUENCE: 10

```
atggcngcng cntggytngg ntggytnytn tgggcnytny tnytnwsngc ngcncarggn       60
garytntaya cnccnaarca ygargcnggn gtntgyacnt tytaygarga rtgyggnaar      120
aayccngary tnwsnggngg nytnacnwsn ytnwsnaayg tnwsntgyyt nwsnaayacn      180
ccngcnmgnc aygtnacngg ngarcayytn gcnytnytnc armgnathtg yccnmgnytn      240
tayaayggnc cnaayacnac nttygcntgy tgywsnacna arcarytnyt nwsnytngar      300
wsnwsnatgw snathacnaa rgcnytnytn acnmgntgyc cngcntgyws ngayaayttty      360
```

-continued

```
gtnwsnytnc aytgycayaa yacntgywsn ccngaycarw snytnttyat haaygtnacn    420
mgngtngtng armgnggngc nggngarccn ccngcngtng tngcntayga rgcnttytay    480
carmgnwsnt tygcngaraa rgcntaygar wsntgywsnc argtnmgnat hccngcngcn    540
gcnwsnytng cngtnggnws natgtgyggn gtntayggnw sngcnytntg yaaygcncar    600
mgntggytna ayttycargg ngayacnggn aayggnytng cnccnytnga yathacntty    660
cayytnytng arccnggnca rgcnytnccn gayggnathc arccnytnaa yggnaarath    720
gcnccntgya aygarwsnca rggngaygay wsngcngtnt gywsntgyca rgaytgygcn    780
gcnwsntgyc cngtnathcc nccnccngar gcnytnmgnc cnwsnttyta yatgggnmgn    840
atgccnggnt ggytngcnyt nathathath ttyacngcng tnttygtnyt nytnwsngcn    900
gtnytngtnm gnytnmgngt ngtnwsnaay mgnaayaara ayaargcnga rggnccncar    960
gargcnccna arytnccnca yaarcayaar ytnwsnccnc ayacnathyt nggnmgntty   1020
ttycaraayt ggggnacnmg ngtngcnwsn tggccnytna cngtnytngc nytnwsntty   1080
athgtngtna thgcnytngc ngcnggnytn acnttyathg arytnacnac ngayccngtn   1140
garytntggw sngcnccnaa rwsncargcn mgnaargara arwsnttyca ygaygarcay   1200
ttyggnccnt tyttymgnac naaycarath ttygtnacng cnmgnaaymg nwsnwsntay   1260
aartaygayw snytnytnyt nggnwsnaar aayttywsng gnathytnws nytngaytty   1320
ytnytngary tnytngaryt ncargarmgn ytnmgncayy tncargtntg gwsnccngar   1380
gcngarmgna ayathwsnyt ncargayath tgytaygcnc cnytnaaycc ntayaayacn   1440
wsnytnwsng aytgytgygt naaywsnytn ytncartayt tycaraayaa ymgnacnytn   1500
ytnatgytna cngcnaayca racnytnaay ggncaracnw snytngtnga ytggaargay   1560
cayttyytnt aytgygcnaa ygcnccnytn acnttyaarg ayggnacnws nytngcnytn   1620
wsntgyatgg cngaytaygg ngcnccngtn ttyccnttyy tngcngtngg nggntaycar   1680
ggnacngayt aywsngargc ngargcnytn athathacnt tywsnytnaa yaaytayccn   1740
gcngaygayc cnmgnatggc ncargcnaar ytntgggarg argcnttyyt naargaratg   1800
garwsnttyc armgnaayac nwsngayaar ttycargtng cnttywsngc ngarmgnwsn   1860
ytngargayg arathaaymg nacnacnath cargayytnc cngtnttygc ngtnwsntay   1920
athathgtnt tyytntayat hwsnytngcn ytnggnwsnt aywsnmgntg ywsnmgngtn   1980
gcngtngarw snaargcnac nytnggnytn ggnggngtna thgtngtnyt nggngcngtn   2040
ytngcngcna tgggnttyta ywsntayytn ggngtnccnw snwsnytngt nathathcar   2100
gtngtnccnt tyytngtnyt ngcngtnggn gcngayaaya thttyathtt ygtnytngar   2160
taycarmgny tnccnmgnat gccnggngar carmgngarg cncayathgg nmgnacnytn   2220
ggnwsngtng cnccnwsnat gytnytntgy wsnytnwsng argcnathtg yttyttyytn   2280
ggngcnytna cnccnatgcc ngcngtnmgn acnttygcny tnacnwsngg nytngcnath   2340
athytngayt tyytnytnca ratgacngcn ttygtngcny tnytnwsnyt ngaywsnaar   2400
mgncargarg cnwsnmgncc ngaygtnytn tgytgyttyw snacnmgnaa rytnccnccn   2460
ccnaargara argarggnyt nytnytnmgn ttyttymgna arathtaygc nccnttyytn   2520
ytncaymgnt tyathmgncc ngtngtnatg ytnytnttyy tnacnytntt yggngcnaay   2580
ytntayytna tgtgyaayat haaygtnggn ytngaycarg arytngcnyt nccnaargay   2640
wsntayytna thgaytaytt yytnttyytn aaymgntayy tngargtngg nccnccngtn   2700
```

-continued tayttygtna cnacnwsngg nttyaaytty wsnwsngarg cnggnatgaa ygcnacntgy 2760
wsnwsngcng gntgyaarws nttywsnytn acncaraara thcartaygc nwsngartty 2820
ccngaycarw sntaygtngc nathgcngcn wsnwsntggg tngaygaytt yathgaytgg 2880
ytnacnccnw snwsnwsntg ytgymgnytn tayathmgng gnccncayaa rgaygartty 2940
tgyccnwsna cngayacnws nttyaaytgy ytnaaraayt gyatgaaymg nacnytnggn 3000
ccngtnmgnc cnacngcnga rcarttycay aartayytnc cntggttyyt naaygayccn 3060
ccnaayathm gntgyccnaa rggnggnytn gcngcntaym gnacnwsngt naayytnwsn 3120
wsngayggnc argtnathgc nwsncartty atggcntayc ayaarccnyt nmgnaaywsn 3180
cargayttya cngargcnyt nmgngcnwsn mgnytnytng cngcnaayat hacngcngay 3240
ytnmgnaarg tnccnggnac ngayccnaay ttygargtnt tyccntayac nathwsnaay 3300
gtnttytayc arcartayyt nacngtnytn ccngarggna thttyacnyt ngcnytntgy 3360
ttygtnccna cnttygtngt ntgytayytn ytnytnggny tngayatgtg ywsnggnath 3420
ytnaayytny tnwsnathat hatgathytn gtngayacna thggnytnat ggcngtntgg 3480
ggnathwsnt ayaaygcngt nwsnytnath aayytngtna cngcngtngg natgwsngtn 3540
garttygtnw sncayathac nmgnwsntty gcngtnwsna cnaarccnac nmgnytngar 3600
mgngcnaarg aygcnacngt nttyatgggn wsngcngtnt tygcnggngt ngcnatgacn 3660
aayttyccng gnathytnat hytnggntty gcncargcnc arytnathca rathttytty 3720
ttymgnytna ayytnytnat hacnytnytn ggnytnytnc ayggnytngt nttyytnccn 3780
gtngtnytnw sntayytngg nccngaygtn aaycargcny tngtncarga rgaraarytn 3840
gcnwsngarg cngcngtngc nccngarccn wsntgyccnc artayccnws nccngcngay 3900
gcngaygcna aygtnaayta yggnttygcn ccngarytng cncayggngc naaygcngcn 3960
mgnwsnwsny tnccnaarws ngaycaraar tty 3993

<210> SEQ ID NO 11
<211> LENGTH: 4002
<212> TYPE: DNA
<213> ORGANISM: Mus sp.
<220> FEATURE:
<221> NAME/KEY: CDS
<222> LOCATION: (1)..(4002)
<223> OTHER INFORMATION:

<400> SEQUENCE: 11 atg gca gct gcc tgg cag gga tgg ctg ctc tgg gcc ctg ctc ctg aat 48
Met Ala Ala Ala Trp Gln Gly Trp Leu Leu Trp Ala Leu Leu Leu Asn
1 5 10 15 tcg gcc cag ggt gag ctc tac aca ccc act cac aaa gct ggc ttc tgc 96
Ser Ala Gln Gly Glu Leu Tyr Thr Pro Thr His Lys Ala Gly Phe Cys
20 25 30 acc ttt tat gaa gag tgt ggg aag aac cca gag ctt tct gga ggc ctc 144
Thr Phe Tyr Glu Glu Cys Gly Lys Asn Pro Glu Leu Ser Gly Gly Leu
35 40 45 aca tca cta tcc aat atc tcc tgc ttg tct aat acc cca gcc cgc cat 192
Thr Ser Leu Ser Asn Ile Ser Cys Leu Ser Asn Thr Pro Ala Arg His
50 55 60 gtc aca ggt gac cac ctg gct ctt ctc cag cgc gtc tgt ccc cgc cta 240
Val Thr Gly Asp His Leu Ala Leu Leu Gln Arg Val Cys Pro Arg Leu
65 70 75 80 tac aat ggc ccc aat gac acc tat gcc tgt tgc tct acc aag cag ctg 288
Tyr Asn Gly Pro Asn Asp Thr Tyr Ala Cys Cys Ser Thr Lys Gln Leu
85 90 95

| | |
|---|---|
| gtg tca tta gac agt agc ctg tct atc acc aag gcc ctc ctt aca cgc<br>Val Ser Leu Asp Ser Ser Leu Ser Ile Thr Lys Ala Leu Leu Thr Arg<br>          100                             105                        110 | 336 |
| tgc ccg gca tgc tct gaa aat ttt gtg agc ata cac tgt cat aat acc<br>Cys Pro Ala Cys Ser Glu Asn Phe Val Ser Ile His Cys His Asn Thr<br>          115                             120                        125 | 384 |
| tgc agc cct gac cag agc ctc ttc atc aat gtt act cgc gtg gtt cag<br>Cys Ser Pro Asp Gln Ser Leu Phe Ile Asn Val Thr Arg Val Val Gln<br>130                             135                             140 | 432 |
| cgg gac cct gga cag ctt cct gct gtg gtg gcc tat gag gcc ttt tat<br>Arg Asp Pro Gly Gln Leu Pro Ala Val Val Ala Tyr Glu Ala Phe Tyr<br>145                           150                           155                        160 | 480 |
| caa cgc agt ttt gca gag aag gcc tat gag tcc tgt agc cgg gtg cgc<br>Gln Arg Ser Phe Ala Glu Lys Ala Tyr Glu Ser Cys Ser Arg Val Arg<br>          165                             170                        175 | 528 |
| atc cct gca gct gcc tcg ctg gct gtg ggc agc atg tgt gga gtg tat<br>Ile Pro Ala Ala Ala Ser Leu Ala Val Gly Ser Met Cys Gly Val Tyr<br>               180                             185                        190 | 576 |
| ggc tct gcc ctc tgc aat gct cag cgc tgg ctc aac ttc caa gga gac<br>Gly Ser Ala Leu Cys Asn Ala Gln Arg Trp Leu Asn Phe Gln Gly Asp<br>               195                             200                        205 | 624 |
| aca ggg aat ggc ctg gct ccg ctg gac atc acc ttc cac ctc ttg gag<br>Thr Gly Asn Gly Leu Ala Pro Leu Asp Ile Thr Phe His Leu Leu Glu<br>          210                             215                        220 | 672 |
| cct ggc cag gcc ctg gca gat ggg atg aag cca ctg gat ggg aag atc<br>Pro Gly Gln Ala Leu Ala Asp Gly Met Lys Pro Leu Asp Gly Lys Ile<br>225                           230                           235                        240 | 720 |
| aca ccc tgc aat gag tcc cag ggt gaa gac tcg gca gcc tgt tcc tgc<br>Thr Pro Cys Asn Glu Ser Gln Gly Glu Asp Ser Ala Ala Cys Ser Cys<br>                           245                           250                        255 | 768 |
| cag gac tgt gca gca tcc tgc cct gtc atc cct ccg ccc ccg gcc ctg<br>Gln Asp Cys Ala Ala Ser Cys Pro Val Ile Pro Pro Pro Pro Ala Leu<br>               260                             265                        270 | 816 |
| cgc cct tct ttc tac atg ggt cga atg cca ggc tgg ctg gct ctc atc<br>Arg Pro Ser Phe Tyr Met Gly Arg Met Pro Gly Trp Leu Ala Leu Ile<br>          275                             280                        285 | 864 |
| atc atc ttc act gct gtc ttt gta ttg ctc tct gtt gtc ctt gtg tat<br>Ile Ile Phe Thr Ala Val Phe Val Leu Leu Ser Val Val Leu Val Tyr<br>          290                             295                        300 | 912 |
| ctc cga gtg gct tcc aac agg aac aag aac aag aca gca ggc tcc cag<br>Leu Arg Val Ala Ser Asn Arg Asn Lys Asn Lys Thr Ala Gly Ser Gln<br>305                           310                           315                        320 | 960 |
| gaa gcc ccc aac ctc cct cgt aag cgc aga ttc tca cct cac act gtc<br>Glu Ala Pro Asn Leu Pro Arg Lys Arg Arg Phe Ser Pro His Thr Val<br>               325                             330                        335 | 1008 |
| ctt ggc cgg ttc ttc gag agc tgg gga aca agg gtg gcc tca tgg cca<br>Leu Gly Arg Phe Phe Glu Ser Trp Gly Thr Arg Val Ala Ser Trp Pro<br>                    340                           345                        350 | 1056 |
| ctc act gtc ttg gca ctg tcc ttc ata gtt gtg ata gcc ttg tca gta<br>Leu Thr Val Leu Ala Leu Ser Phe Ile Val Val Ile Ala Leu Ser Val<br>          355                             360                        365 | 1104 |
| ggc ctg acc ttt ata gaa ctc acc aca gac cct gtg gaa ctg tgg tcg<br>Gly Leu Thr Phe Ile Glu Leu Thr Thr Asp Pro Val Glu Leu Trp Ser<br>          370                             375                        380 | 1152 |
| gcc cct aaa agc caa gcc cgg aaa gaa aag gct ttc cat gac gag cat<br>Ala Pro Lys Ser Gln Ala Arg Lys Glu Lys Ala Phe His Asp Glu His<br>385                           390                           395                        400 | 1200 |
| ttt ggc ccc ttc ttc cga acc aac cag att ttt gtg aca gct aag aac<br>Phe Gly Pro Phe Phe Arg Thr Asn Gln Ile Phe Val Thr Ala Lys Asn | 1248 |

-continued

```
                405                 410                 415
agg tcc agc tac aag tac gac tcc ctg cta ggg ccc aag aac ttc    1296
Arg Ser Ser Tyr Lys Tyr Asp Ser Leu Leu Leu Gly Pro Lys Asn Phe
            420                 425                 430 agt ggg atc cta tcc ctg gac ttg ctg cag gag ctg ttg gag cta cag    1344
Ser Gly Ile Leu Ser Leu Asp Leu Leu Gln Glu Leu Leu Glu Leu Gln
                435                 440                 445 gag aga ctt cga cac ctg caa gtg tgg tcc cat gag gca cag cgc aac    1392
Glu Arg Leu Arg His Leu Gln Val Trp Ser His Glu Ala Gln Arg Asn
        450                 455                 460 atc tcc ctc cag gac atc tgc tat gct ccc ctc aac ccg cat aac acc    1440
Ile Ser Leu Gln Asp Ile Cys Tyr Ala Pro Leu Asn Pro His Asn Thr
465                 470                 475                 480 agc ctc act gac tgc tgt gtc aac agc ctc ctt caa tac ttc cag aac    1488
Ser Leu Thr Asp Cys Cys Val Asn Ser Leu Leu Gln Tyr Phe Gln Asn
                485                 490                 495 aac cac aca ctc ctg ctc aca gcc aat cag act ctg aat ggc cag    1536
Asn His Thr Leu Leu Leu Thr Ala Asn Gln Thr Leu Asn Gly Gln
            500                 505                 510 acc tcc ctg gtg gac tgg aag gac cat ttc ctc tac tgt gcc aat gcc    1584
Thr Ser Leu Val Asp Trp Lys Asp His Phe Leu Tyr Cys Ala Asn Ala
        515                 520                 525 cct ctc acg tac aaa gat ggc aca gcc ctg gcc ctg agc tgc ata gct    1632
Pro Leu Thr Tyr Lys Asp Gly Thr Ala Leu Ala Leu Ser Cys Ile Ala
530                 535                 540 gac tac ggg gca cct gtc ttc ccc ttc ctt gct gtt ggc ggc tac caa    1680
Asp Tyr Gly Ala Pro Val Phe Pro Phe Leu Ala Val Gly Gly Tyr Gln
                545                 550                 555                 560 ggg acg gac tac tcg gag gca gaa gcc ctg atc ata acc ttc tct atc    1728
Gly Thr Asp Tyr Ser Glu Ala Glu Ala Leu Ile Ile Thr Phe Ser Ile
                    565                 570                 575 aat aac tac ccc gct gat gat ccc cgc atg gcc cac gcc aag ctc tgg    1776
Asn Asn Tyr Pro Ala Asp Asp Pro Arg Met Ala His Ala Lys Leu Trp
            580                 585                 590 gag gag gct ttc ttg aag gaa atg caa tcc ttc cag aga agc aca gct    1824
Glu Glu Ala Phe Leu Lys Glu Met Gln Ser Phe Gln Arg Ser Thr Ala
        595                 600                 605 gac aag ttc cag att gcg ttc tca gct gag cgt tct ctg gag gac gag    1872
Asp Lys Phe Gln Ile Ala Phe Ser Ala Glu Arg Ser Leu Glu Asp Glu
610                 615                 620 atc aat cgc act acc atc cag gac ctg cct gtc ttt gcc atc agc tac    1920
Ile Asn Arg Thr Thr Ile Gln Asp Leu Pro Val Phe Ala Ile Ser Tyr
625                 630                 635                 640 ctt atc gtc ttc ctg tac atc tcc ctg gcc ctg ggc agc tac tcc aga    1968
Leu Ile Val Phe Leu Tyr Ile Ser Leu Ala Leu Gly Ser Tyr Ser Arg
                645                 650                 655 tgg agc cga gtt gcg gtg gat tcc aag gct act ctg ggc cta ggt ggg    2016
Trp Ser Arg Val Ala Val Asp Ser Lys Ala Thr Leu Gly Leu Gly Gly
            660                 665                 670 gtg gct gtt gtg ctg gga gca gtc gtc gct gcc atg ggc ttc tac tcc    2064
Val Ala Val Val Leu Gly Ala Val Val Ala Ala Met Gly Phe Tyr Ser
        675                 680                 685 tac ctg ggt gtc ccc tcc tct ctg gtc atc att caa gtg gta cct ttc    2112
Tyr Leu Gly Val Pro Ser Ser Leu Val Ile Ile Gln Val Val Pro Phe
            690                 695                 700 ctg gtg ctg gct gtg gga gct gac aac atc ttc atc ttt gtt ctt gag    2160
Leu Val Leu Ala Val Gly Ala Asp Asn Ile Phe Ile Phe Val Leu Glu
705                 710                 715                 720 tac cag agg ctg cct agg atg ccc ggg gag cag cga gag gct cac att    2208
```

```
Tyr Gln Arg Leu Pro Arg Met Pro Gly Glu Gln Arg Glu Ala His Ile
            725                 730                 735 ggc cgc acc ctg ggt agt gtg gcc ccc agc atg ctg ctg tgc agc ctc      2256
Gly Arg Thr Leu Gly Ser Val Ala Pro Ser Met Leu Leu Cys Ser Leu
            740                 745                 750 tct gag gcc atc tgc ttc ttt cta ggg gcc ctg acc tcc atg cca gct      2304
Ser Glu Ala Ile Cys Phe Phe Leu Gly Ala Leu Thr Ser Met Pro Ala
            755                 760                 765 gtg agg acc ttt gcc ttg acc tct ggc tta gca atc atc ttt gac ttc      2352
Val Arg Thr Phe Ala Leu Thr Ser Gly Leu Ala Ile Ile Phe Asp Phe
            770                 775                 780 ctg ctc cag atg aca gcc ttt gtg gcc ctg ctc tcc ctg gat agc aag      2400
Leu Leu Gln Met Thr Ala Phe Val Ala Leu Leu Ser Leu Asp Ser Lys
785                 790                 795                 800 agg cag gag gcc tct cgc ccc gac gtc gtg tgc tgc ttt tca agc cga      2448
Arg Gln Glu Ala Ser Arg Pro Asp Val Val Cys Cys Phe Ser Ser Arg
            805                 810                 815 aat ctg ccc cca ccg aaa caa aaa gaa ggc ctc tta ctt tgc ttc ttc      2496
Asn Leu Pro Pro Pro Lys Gln Lys Glu Gly Leu Leu Leu Cys Phe Phe
            820                 825                 830 cgc aag ata tac act ccc ttc ctg ctg cac aga ttc atc cgc cct gtt      2544
Arg Lys Ile Tyr Thr Pro Phe Leu Leu His Arg Phe Ile Arg Pro Val
            835                 840                 845 gtg ctg ctc ctc ttt ctg gtc ctg ttt gga gca aac ctc tac tta atg      2592
Val Leu Leu Leu Phe Leu Val Leu Phe Gly Ala Asn Leu Tyr Leu Met
            850                 855                 860 tgc aac atc agc gtg ggg ctg gac cag gat ctg gct ctg ccc aag gat      2640
Cys Asn Ile Ser Val Gly Leu Asp Gln Asp Leu Ala Leu Pro Lys Asp
865                 870                 875                 880 tcc tac ctg ata gac tac ttc ctc ttt ctg aac cgg tac ttg gaa gtg      2688
Ser Tyr Leu Ile Asp Tyr Phe Leu Phe Leu Asn Arg Tyr Leu Glu Val
            885                 890                 895 ggg cct cca gtg tac ttt gac acc acc tca ggc tac aac ttt tcc acc      2736
Gly Pro Pro Val Tyr Phe Asp Thr Thr Ser Gly Tyr Asn Phe Ser Thr
            900                 905                 910 gag gca ggc atg aac gcc att tgc tct agt gca ggc tgt gag agc ttc      2784
Glu Ala Gly Met Asn Ala Ile Cys Ser Ser Ala Gly Cys Glu Ser Phe
            915                 920                 925 tcc cta acc cag aaa atc cag tat gcc agt gaa ttc cct aat cag tct      2832
Ser Leu Thr Gln Lys Ile Gln Tyr Ala Ser Glu Phe Pro Asn Gln Ser
            930                 935                 940 tat gtg gct att gct gca tcc tcc tgg gta gat gac ttc atc gac tgg      2880
Tyr Val Ala Ile Ala Ala Ser Ser Trp Val Asp Asp Phe Ile Asp Trp
945                 950                 955                 960 ctg acc cca tcc tcc tcc tgc tgc cgc att tat acc cgt ggc ccc cat      2928
Leu Thr Pro Ser Ser Ser Cys Cys Arg Ile Tyr Thr Arg Gly Pro His
            965                 970                 975 aaa gat gag ttc tgt ccc tca acg gat act tcc ttc aac tgt ctc aaa      2976
Lys Asp Glu Phe Cys Pro Ser Thr Asp Thr Ser Phe Asn Cys Leu Lys
            980                 985                 990 aac tgc atg aac cgc act ctg ggt ccc gtg aga ccc aca aca gaa cag      3024
Asn Cys Met Asn Arg Thr Leu Gly Pro Val Arg Pro Thr Thr Glu Gln
            995                 1000                1005 ttt cat aag tac ctg ccc tgg ttc ctg aat gat acg ccc aac atc          3069
Phe His Lys Tyr Leu Pro Trp Phe Leu Asn Asp Thr Pro Asn Ile
            1010                1015                1020 aga tgt cct aaa ggg ggc cta gca gcg tat aga acc tct gtg aat          3114
Arg Cys Pro Lys Gly Gly Leu Ala Ala Tyr Arg Thr Ser Val Asn
            1025                1030                1035
```

| | | |
|---|---|---|
| ttg agc tca gat ggc cag att ata gcc tcc cag ttc atg gcc tac<br>Leu Ser Ser Asp Gly Gln Ile Ile Ala Ser Gln Phe Met Ala Tyr<br>1040                      1045                      1050 | | 3159 |
| cac aag ccc tta cgg aac tca cag gac ttt aca gaa gct ctc cgg<br>His Lys Pro Leu Arg Asn Ser Gln Asp Phe Thr Glu Ala Leu Arg<br>1055                      1060                      1065 | | 3204 |
| gca tcc cgg ttg cta gca gcc aac atc aca gct gaa cta cgg aag<br>Ala Ser Arg Leu Leu Ala Ala Asn Ile Thr Ala Glu Leu Arg Lys<br>1070                      1075                      1080 | | 3249 |
| gtg cct ggg aca gat ccc aac ttt gag gtc ttc cct tac acg atc<br>Val Pro Gly Thr Asp Pro Asn Phe Glu Val Phe Pro Tyr Thr Ile<br>1085                      1090                      1095 | | 3294 |
| tcc aat gtg ttc tac cag caa tac ctg acg gtt ctc cct gag gga<br>Ser Asn Val Phe Tyr Gln Gln Tyr Leu Thr Val Leu Pro Glu Gly<br>1100                      1105                      1110 | | 3339 |
| atc ttc act ctt gct ctc tgc ttc gtg ccc acc ttt gtg gtc tgc<br>Ile Phe Thr Leu Ala Leu Cys Phe Val Pro Thr Phe Val Val Cys<br>1115                      1120                      1125 | | 3384 |
| tac ctc cta ctg ggc ctg gac ata cgc tca ggc atc ctc aac ctg<br>Tyr Leu Leu Leu Gly Leu Asp Ile Arg Ser Gly Ile Leu Asn Leu<br>1130                      1135                      1140 | | 3429 |
| ctc tcc atc att atg atc ctc gtg gac acc atc ggc ctc atg gct<br>Leu Ser Ile Ile Met Ile Leu Val Asp Thr Ile Gly Leu Met Ala<br>1145                      1150                      1155 | | 3474 |
| gtg tgg ggt atc agc tac aat gct gtg tcc ctc atc aac ctt gtc<br>Val Trp Gly Ile Ser Tyr Asn Ala Val Ser Leu Ile Asn Leu Val<br>1160                      1165                      1170 | | 3519 |
| acg gca gtg ggc atg tct gtg gag ttc gtg tcc cac att acc cgg<br>Thr Ala Val Gly Met Ser Val Glu Phe Val Ser His Ile Thr Arg<br>1175                      1180                      1185 | | 3564 |
| tcc ttt gct gta agc acc aag cct acc cgg ctg gag aga gcc aaa<br>Ser Phe Ala Val Ser Thr Lys Pro Thr Arg Leu Glu Arg Ala Lys<br>1190                      1195                      1200 | | 3609 |
| gat gct act atc ttc atg ggc agt gcg gtg ttt gct gga gtg gcc<br>Asp Ala Thr Ile Phe Met Gly Ser Ala Val Phe Ala Gly Val Ala<br>1205                      1210                      1215 | | 3654 |
| atg acc aac ttc ccg ggc atc ctc atc ctg ggc ttt gct cag gcc<br>Met Thr Asn Phe Pro Gly Ile Leu Ile Leu Gly Phe Ala Gln Ala<br>1220                      1225                      1230 | | 3699 |
| cag ctt atc cag att ttc ttc ttc cgc ctc aac ctc ctg atc acc<br>Gln Leu Ile Gln Ile Phe Phe Phe Arg Leu Asn Leu Leu Ile Thr<br>1235                      1240                      1245 | | 3744 |
| ttg ctg ggt ctg cta cac ggc ctg gtc ttc ctg ccc gtt gtc ctc<br>Leu Leu Gly Leu Leu His Gly Leu Val Phe Leu Pro Val Val Leu<br>1250                      1255                      1260 | | 3789 |
| agc tat ctg ggg cca gat gtt aac caa gct ctg gta ctg gag gag<br>Ser Tyr Leu Gly Pro Asp Val Asn Gln Ala Leu Val Leu Glu Glu<br>1265                      1270                      1275 | | 3834 |
| aaa cta gcc act gag gca gcc atg gtc tca gag cct tct tgc cca<br>Lys Leu Ala Thr Glu Ala Ala Met Val Ser Glu Pro Ser Cys Pro<br>1280                      1285                      1290 | | 3879 |
| cag tac ccc ttc ccg gct gat gca aac acc agt gac tat gtt aac<br>Gln Tyr Pro Phe Pro Ala Asp Ala Asn Thr Ser Asp Tyr Val Asn<br>1295                      1300                      1305 | | 3924 |
| tac ggc ttt aat cca gaa ttt atc cct gaa att aat gct gct agc<br>Tyr Gly Phe Asn Pro Glu Phe Ile Pro Glu Ile Asn Ala Ala Ser<br>1310                      1315                      1320 | | 3969 |
| agc tct ctg ccc aaa agt gac caa aag ttc taa<br>Ser Ser Leu Pro Lys Ser Asp Gln Lys Phe<br>1325                      1330 | | 4002 |

-continued

<210> SEQ ID NO 12
<211> LENGTH: 1333
<212> TYPE: PRT
<213> ORGANISM: Mus sp.

<400> SEQUENCE: 12

Met Ala Ala Ala Trp Gln Gly Trp Leu Leu Trp Ala Leu Leu Leu Asn
1               5                   10                  15

Ser Ala Gln Gly Glu Leu Tyr Thr Pro Thr His Lys Ala Gly Phe Cys
                20                  25                  30

Thr Phe Tyr Glu Glu Cys Gly Lys Asn Pro Glu Leu Ser Gly Gly Leu
            35                  40                  45

Thr Ser Leu Ser Asn Ile Ser Cys Leu Ser Asn Thr Pro Ala Arg His
    50                  55                  60

Val Thr Gly Asp His Leu Ala Leu Leu Gln Arg Val Cys Pro Arg Leu
65                  70                  75                  80

Tyr Asn Gly Pro Asn Asp Thr Tyr Ala Cys Cys Ser Thr Lys Gln Leu
                85                  90                  95

Val Ser Leu Asp Ser Ser Leu Ser Ile Thr Lys Ala Leu Leu Thr Arg
                100                 105                 110

Cys Pro Ala Cys Ser Glu Asn Phe Val Ser Ile His Cys His Asn Thr
            115                 120                 125

Cys Ser Pro Asp Gln Ser Leu Phe Ile Asn Val Thr Arg Val Val Gln
    130                 135                 140

Arg Asp Pro Gly Gln Leu Pro Ala Val Val Ala Tyr Glu Ala Phe Tyr
145                 150                 155                 160

Gln Arg Ser Phe Ala Glu Lys Ala Tyr Glu Ser Cys Ser Arg Val Arg
                165                 170                 175

Ile Pro Ala Ala Ala Ser Leu Ala Val Gly Ser Met Cys Gly Val Tyr
            180                 185                 190

Gly Ser Ala Leu Cys Asn Ala Gln Arg Trp Leu Asn Phe Gln Gly Asp
    195                 200                 205

Thr Gly Asn Gly Leu Ala Pro Leu Asp Ile Thr Phe His Leu Leu Glu
    210                 215                 220

Pro Gly Gln Ala Leu Ala Asp Gly Met Lys Pro Leu Asp Gly Lys Ile
225                 230                 235                 240

Thr Pro Cys Asn Glu Ser Gln Gly Glu Asp Ser Ala Ala Cys Ser Cys
                245                 250                 255

Gln Asp Cys Ala Ala Ser Cys Pro Val Ile Pro Pro Pro Ala Leu
            260                 265                 270

Arg Pro Ser Phe Tyr Met Gly Arg Met Pro Gly Trp Leu Ala Leu Ile
    275                 280                 285

Ile Ile Phe Thr Ala Val Phe Val Leu Leu Ser Val Val Leu Val Tyr
    290                 295                 300

Leu Arg Val Ala Ser Asn Arg Asn Lys Asn Lys Thr Ala Gly Ser Gln
305                 310                 315                 320

Glu Ala Pro Asn Leu Pro Arg Lys Arg Phe Ser Pro His Thr Val
                325                 330                 335

Leu Gly Arg Phe Phe Glu Ser Trp Gly Thr Arg Val Ala Ser Trp Pro
            340                 345                 350

Leu Thr Val Leu Ala Leu Ser Phe Ile Val Val Ile Ala Leu Ser Val
    355                 360                 365

Gly Leu Thr Phe Ile Glu Leu Thr Thr Asp Pro Val Glu Leu Trp Ser

```
                370                 375                 380
Ala Pro Lys Ser Gln Ala Arg Lys Glu Lys Ala Phe His Asp Glu His
385                 390                 395                 400

Phe Gly Pro Phe Phe Arg Thr Asn Gln Ile Phe Val Thr Ala Lys Asn
                405                 410                 415

Arg Ser Ser Tyr Lys Tyr Asp Ser Leu Leu Gly Pro Lys Asn Phe
                420                 425                 430

Ser Gly Ile Leu Ser Leu Asp Leu Leu Gln Glu Leu Glu Leu Gln
            435                 440                 445

Glu Arg Leu Arg His Leu Gln Val Trp Ser His Glu Ala Gln Arg Asn
450                 455                 460

Ile Ser Leu Gln Asp Ile Cys Tyr Ala Pro Leu Asn Pro His Asn Thr
465                 470                 475                 480

Ser Leu Thr Asp Cys Cys Val Asn Ser Leu Leu Gln Tyr Phe Gln Asn
                485                 490                 495

Asn His Thr Leu Leu Leu Thr Ala Asn Gln Thr Leu Asn Gly Gln
                500                 505                 510

Thr Ser Leu Val Asp Trp Lys Asp His Phe Leu Tyr Cys Ala Asn Ala
            515                 520                 525

Pro Leu Thr Tyr Lys Asp Gly Thr Ala Leu Ala Leu Ser Cys Ile Ala
    530                 535                 540

Asp Tyr Gly Ala Pro Val Phe Pro Phe Leu Ala Val Gly Gly Tyr Gln
545                 550                 555                 560

Gly Thr Asp Tyr Ser Glu Ala Glu Ala Leu Ile Ile Thr Phe Ser Ile
                565                 570                 575

Asn Asn Tyr Pro Ala Asp Asp Pro Arg Met Ala His Ala Lys Leu Trp
                580                 585                 590

Glu Glu Ala Phe Leu Lys Glu Met Gln Ser Phe Gln Arg Ser Thr Ala
                595                 600                 605

Asp Lys Phe Gln Ile Ala Phe Ser Ala Glu Arg Ser Leu Glu Asp Glu
                610                 615                 620

Ile Asn Arg Thr Thr Ile Gln Asp Leu Pro Val Phe Ala Ile Ser Tyr
625                 630                 635                 640

Leu Ile Val Phe Leu Tyr Ile Ser Leu Ala Leu Gly Ser Tyr Ser Arg
                645                 650                 655

Trp Ser Arg Val Ala Val Asp Ser Lys Ala Thr Leu Gly Leu Gly Gly
                660                 665                 670

Val Ala Val Val Leu Gly Ala Val Val Ala Ala Met Gly Phe Tyr Ser
            675                 680                 685

Tyr Leu Gly Val Pro Ser Ser Leu Val Ile Ile Gln Val Val Pro Phe
    690                 695                 700

Leu Val Leu Ala Val Gly Ala Asp Asn Ile Phe Ile Phe Val Leu Glu
705                 710                 715                 720

Tyr Gln Arg Leu Pro Arg Met Pro Gly Glu Gln Arg Glu Ala His Ile
                725                 730                 735

Gly Arg Thr Leu Gly Ser Val Ala Pro Ser Met Leu Leu Cys Ser Leu
                740                 745                 750

Ser Glu Ala Ile Cys Phe Phe Leu Gly Ala Leu Thr Ser Met Pro Ala
            755                 760                 765

Val Arg Thr Phe Ala Leu Thr Ser Gly Leu Ala Ile Ile Phe Asp Phe
    770                 775                 780

Leu Leu Gln Met Thr Ala Phe Val Ala Leu Leu Ser Leu Asp Ser Lys
785                 790                 795                 800
```

-continued

```
Arg Gln Glu Ala Ser Arg Pro Asp Val Val Cys Cys Phe Ser Ser Arg
            805                 810                 815
Asn Leu Pro Pro Pro Lys Gln Lys Glu Gly Leu Leu Leu Cys Phe Phe
            820                 825                 830
Arg Lys Ile Tyr Thr Pro Phe Leu Leu His Arg Phe Ile Arg Pro Val
            835                 840                 845
Val Leu Leu Leu Phe Leu Val Leu Phe Gly Ala Asn Leu Tyr Leu Met
            850                 855                 860
Cys Asn Ile Ser Val Gly Leu Asp Gln Asp Leu Ala Leu Pro Lys Asp
865             870                 875                 880
Ser Tyr Leu Ile Asp Tyr Phe Leu Phe Leu Asn Arg Tyr Leu Glu Val
                885                 890                 895
Gly Pro Pro Val Tyr Phe Asp Thr Thr Ser Gly Tyr Asn Phe Ser Thr
                900                 905                 910
Glu Ala Gly Met Asn Ala Ile Cys Ser Ser Ala Gly Cys Glu Ser Phe
                915                 920                 925
Ser Leu Thr Gln Lys Ile Gln Tyr Ala Ser Glu Phe Pro Asn Gln Ser
            930                 935                 940
Tyr Val Ala Ile Ala Ala Ser Ser Trp Val Asp Asp Phe Ile Asp Trp
945                 950                 955                 960
Leu Thr Pro Ser Ser Ser Cys Cys Arg Ile Tyr Thr Arg Gly Pro His
                965                 970                 975
Lys Asp Glu Phe Cys Pro Ser Thr Asp Thr Ser Phe Asn Cys Leu Lys
            980                 985                 990
Asn Cys Met Asn Arg Thr Leu Gly  Pro Val Arg Pro Thr  Thr Glu Gln
            995                  1000                 1005
Phe His  Lys Tyr Leu Pro Trp  Phe Leu Asn Asp Thr  Pro Asn Ile
     1010                 1015                 1020
Arg Cys Pro Lys Gly Gly Leu  Ala Ala Tyr Arg Thr  Ser Val Asn
     1025                 1030                 1035
Leu Ser  Ser Asp Gly Gln Ile  Ile Ala Ser Gln Phe  Met Ala Tyr
     1040                 1045                 1050
His Lys Pro Leu Arg Asn Ser  Gln Asp Phe Thr Glu  Ala Leu Arg
     1055                 1060                 1065
Ala Ser  Arg Leu Leu Ala Ala  Asn Ile Thr Ala Glu  Leu Arg Lys
     1070                 1075                 1080
Val Pro  Gly Thr Asp Pro Asn  Phe Glu Val Phe Pro  Tyr Thr Ile
     1085                 1090                 1095
Ser Asn  Val Phe Tyr Gln Gln  Tyr Leu Thr Val Leu  Pro Glu Gly
     1100                 1105                 1110
Ile Phe  Thr Leu Ala Leu Cys  Phe Val Pro Thr Phe  Val Val Cys
     1115                 1120                 1125
Tyr Leu  Leu Leu Gly Leu Asp  Ile Arg Ser Gly Ile  Leu Asn Leu
     1130                 1135                 1140
Leu Ser  Ile Ile Met Ile Leu  Val Asp Thr Ile Gly  Leu Met Ala
     1145                 1150                 1155
Val Trp  Gly Ile Ser Tyr Asn  Ala Val Ser Leu Ile  Asn Leu Val
     1160                 1165                 1170
Thr Ala  Val Gly Met Ser Val  Glu Phe Val Ser His  Ile Thr Arg
     1175                 1180                 1185
Ser Phe  Ala Val Ser Thr Lys  Pro Thr Arg Leu Glu  Arg Ala Lys
     1190                 1195                 1200
```

-continued

```
Asp Ala Thr Ile Phe Met Gly Ser Ala Val Phe Ala Gly Val Ala
1205                1210                1215

Met Thr Asn Phe Pro Gly Ile Leu Ile Leu Gly Phe Ala Gln Ala
1220                1225                1230

Gln Leu Ile Gln Ile Phe Phe Phe Arg Leu Asn Leu Leu Ile Thr
1235                1240                1245

Leu Leu Gly Leu Leu His Gly Leu Val Phe Leu Pro Val Val Leu
1250                1255                1260

Ser Tyr Leu Gly Pro Asp Val Asn Gln Ala Leu Val Leu Glu Glu
1265                1270                1275

Lys Leu Ala Thr Glu Ala Ala Met Val Ser Glu Pro Ser Cys Pro
1280                1285                1290

Gln Tyr Pro Phe Pro Ala Asp Ala Asn Thr Ser Asp Tyr Val Asn
1295                1300                1305

Tyr Gly Phe Asn Pro Glu Phe Ile Pro Glu Ile Asn Ala Ala Ser
1310                1315                1320

Ser Ser Leu Pro Lys Ser Asp Gln Lys Phe
1325                1330
```

<210> SEQ ID NO 13
<211> LENGTH: 3999
<212> TYPE: DNA
<213> ORGANISM: Mus sp.
<220> FEATURE:
<221> NAME/KEY: misc_feature
<222> LOCATION: (1)..(3999)
<223> OTHER INFORMATION: n is g or a or t or c

<400> SEQUENCE: 13

```
atggcngcng cntggcargg ntggytnytn tgggcnytny tnytnaayws ngcncarggn         60
garytntaya cnccnacnca yaargcnggn ttytgyacnt tytaygarga rtgyggnaar        120
aayccngary tnwsnggngg nytnacnwsn ytnwsnaaya thwsntgyyt nwsnaayacn        180
ccngcnmgnc aygtnacngg ngaycayyta gcnytnytnc armgntgtnt yccnmgnytn        240
tayaayggnc cnaaygayac ntaygcntgy tgywsnacna arcarytngt nwsnytngay        300
wsnwsnytnw snathacnaa rgcnytnytn acnmgntgyc cngcntgyws ngaraayttr        360
gtnwsnathc aytgycayaa yacntgywsn ccngaycarw snytnttyat haaygtnacn        420
mgngtngtnc armgngaycc nggncarytn ccngcngtng tngcntayga rgcnttytay        480
carmgnwsnt tygcngaraa rgcntaygar wsntgywsnm gngtnmgnat hccngcngcn        540
gcnwsnytng cngtnggnws natgtgyggn gtntayggnw sngcnytntg yaaygcncar        600
mgntggytna ayttycargg ngayacnggn aayggnytng cnccnytnga yathacntty        660
cayytnytng arccnggnca rgcnytngcn gayggnatga arccnytnga yggnaarath        720
acnccntgya aygarwsnca rggngargay wsngcngcnt gywsntgyca rgaytgygcn        780
gcnwsntgyc cngtnathcc nccnccnccn gcnytnmgnc cnwsnttyta yatgggnmgn        840
atgccnggnt ggytngcnyt nathathath ttyacngcng tnttygtnyt nytnwsngtn        900
gtnytngtnt ayytnmgngt ngcnwsnaay mgnaayaara ayaaracngc nggnwsncar        960
gargcnccna ayytnccnmg naarmgnmgn ttywsnccnc ayacngtnyt nggnmgntty       1020
ttygarwsnt ggggnacnmg ngtngcnwsn tggccnytna cngtnytngc nytnwsntty       1080
athgtngtna thgcnytnws ngtnggnyta acnttyathg arytnacnac ngaycgntn        1140
garytntggw sngcnccnaa rwsncargcn mgnaargara argcnttyca ygaygarcay       1200
```

-continued

```
ttyggnccnt tyttymgnac naaycarath ttygtnacng cnaaraaymg nwsnwsntay   1260
aartaygayw snytnytnyt nggnccnaar aayttywsng gnathytnws nytngayytn   1320
ytncargary tnytngaryt ncargarmgn ytnmgncayy tncargtntg gwsncaygar   1380
gcncarmgna ayathwsnyt ncargayath tgytaygcnc cnytnaaycc ncayaayacn   1440
wsnytnacng aytgytgygt naaywsnytn ytncartayt tycaraayaa ycayacnytn   1500
ytnytnytna cngcnaayca racnytnaay ggncaracnw snytngtnga ytggaargay   1560
cayttyytnt aytgygcnaa ygcnccnytn acntayaarg ayggnacngc nytngcnytn   1620
wsntgyathg cngaytaygg ngcnccngtn ttyccnttyy tngcngtngg nggntaycar   1680
ggnacngayt aywsngargc ngargcnytn athathacnt tywsnathaa yaaytayccn   1740
gcngaygayc cnmgnatggc ncaygcnaar ytntgggarg argcnttyyt naargaratg   1800
carwsnttyc armgnwsnac ngcngayaar ttycarathg cnttywsngc ngarmgnwsn   1860
ytngargayg arathaaymg nacnacnath cargayytnc cngtnttygc nathwsntay   1920
ytnathgtnt tyytntayat hwsnytngcn ytnggnwsnt aywsnmgntg gwsnmgngtn   1980
gcngtngayw snaargcnac nytnggnytn ggnggngtng cngtngtnyt nggngcngtn   2040
gtngcngcna tgggnttyta ywsntayytn ggngtnccnw snwsnytngt nathathcar   2100
gtngtnccnt tyytngtnyt ngcngtnggn gcngayaaya thttyathtt ygtnytngar   2160
taycarmgny tnccnmgnat gccnggngar carmgngarg cncayathgg nmgnacnytn   2220
ggnwsngtng cnccnwsnat gytnytntgy wsnytnwsng argcnathtg yttyttyytn   2280
ggngcnytna cnwsnatgcc ngcngtnmgn acnttygcny tnacnwsngg nytngcnath   2340
athttygayt tyytnytnca ratgacngcn ttygtngcny tnytnwsnyt ngaywsnaar   2400
mgncargarg cnwsnmgncc ngaygtngtn tgytgyttyw snwsnmgnaa yytnccnccn   2460
ccnaarcara argarggnyt nytnytntgy ttyttymgna arathtayac nccnttyytn   2520
ytncaymgnt tyathmgncc ngtngtnytn ytnytnttyy tngtnytntt yggngcnaay   2580
ytntayytna tgtgyaayat hwsngtnggn ytngaycarg ayytngcnyt nccnaargay   2640
wsntayytna thgaytaytt yytnttyytn aaymgntayy tngargtngg nccnccngtn   2700
tayttygaya cnacnwsngg ntayaaytty wsnacngarg cnggnatgaa ygcnathtgy   2760
wsnwsngcng gntgygarws nttywsnytn acncaraara thcartaygc nwsngartty   2820
ccnaaycarw sntaygtngc nathgcngcn wsnwsntggg tngaygaytt yathgaytgg   2880
ytnacnccnw snwsnwsntg ytgymgnath tayacnmgng gnccncayaa rgaygartty   2940
tgyccnwsna cngayacnws nttyaaytgy ytnaaraayt gyatgaaymg nacnytnggn   3000
ccngtnmgnc cnacnacnga rcarttycay aartayytnc cntggttyyt naaygayacn   3060
ccnaayathm gntgyccnaa rggnggnytn gcngcntaym gnacnwsngt naayytnwsn   3120
wsngayggnc arathathgc nwsncartty atggcntayc ayaarccnyt nmgnaaywsn   3180
cargayttya cngargcnyt nmgngcnwsn mgnytnytng cngcnaayat hacngcngar   3240
ytnmgnaarg tnccnggnac ngayccnaay ttygargtnt tyccntayac nathwsnaay   3300
gtnttytayc arcartayyt nacngtnytn ccngarggna thttyacnyt ngcnytntgy   3360
ttygtnccna cnttygtngt ntgytayytn ytnytnggny tngayathmg nwsnggnath   3420
ytnaayytny tnwsnathat hatgathytn gtngayacna thggnytnat ggcngtntgg   3480
ggnathwsnt ayaaygcngt nwsnytnath aayytngtna cngcngtngg natgwsngtn   3540
garttygtnw sncayathac nmgnwsntty gcngtnwsna cnaarccnac nmgnytngar   3600
```

```
mgngcnaarg aygcnacnat httyatgggn wsngcngtnt tygcnggngt ngcnatgacn      3660
aayttyccng gnathytnat hytnggntty gcncargcnc arytnathca rathttytty      3720
ttymgnytna ayytnytnat hacnytnytn ggnytnytnc ayggnytngt nttyytnccn      3780
gtngtnytnw sntayytngg nccngaygtn aaycargcny tngtnytnga rgaraarytn      3840
gcnacngarg cngcnatggt nwsngarccn wsntgyccnc artayccntt yccngcngay      3900
gcnaayacnw sngaytaygt naaytayggn ttyaaylccng arttyathcc ngarathaay    3960
gcngcnwsnw snwsnytncc naarwsngay caraartty                           3999
```

<210> SEQ ID NO 14
<211> LENGTH: 20
<212> TYPE: DNA
<213> ORGANISM: Artificial sequence
<220> FEATURE:
<223> OTHER INFORMATION: primer

<400> SEQUENCE: 14

```
tcttcaccct tgctctttgc                                                  20
```

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15

```
aatgatggag agtaggttga ggat                                             24
```

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16

```
tgcccacctt tgttgtctgc taccta                                           26
```

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17

```
atcgctgaca ggatgcagaa g                                                21
```

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18

```
tcaggaggag caatgatctt ga                                               22
```

<210> SEQ ID NO 19
<211> LENGTH: 30
<212> TYPE: DNA

<213> ORGANISM: Artificial Sequence
<220> FEATURE:
<223> OTHER INFORMATION: primer

<400> SEQUENCE: 19
agattactgc cctggctcct agcaccatta					30

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
atcctcatcc tgggctttgc					20

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gcaaggtgat caggaggttg a					21

<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22
cccagcttat ccagattttc ttcttccgc					29

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tcttcaccct tgctctttgc					20

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
aatgatggag agtaggttga ggat					24

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
tgcccacctt tgttgtctgc tacc					24

```
<210> SEQ ID NO 26
<211> LENGTH: 23
<212> TYPE: DNA
<213> ORGANISM: Artificial Sequence
<220> FEATURE:
<223> OTHER INFORMATION: primer

<400> SEQUENCE: 26
agcacctgtc cactgaagat ttc                                              23

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
tggacgctga gcttcagttc t                                                21

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
cttctctgcg ctgcctcgat ggaa                                             24

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
agtaaaaagg gctcgcagga t                                                21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
ggcagctggt gacatcagag a                                                21

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
aggaggccat gcaggcctac tctga                                            25

<210> SEQ ID NO 32
<211> LENGTH: 21
<212> TYPE: DNA
<213> ORGANISM: Artificial Sequence
<220> FEATURE:
```

```
<223> OTHER INFORMATION: primer

<400> SEQUENCE: 32
gagtccacgg tcagtccatg t                                              21

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
ttatgaacaa caatgccaag caa                                            23

<210> SEQ ID NO 34
<211> LENGTH: 34
<212> TYPE: DNA
<213> ORGANISM: Artificial Sequence
<220> FEATURE:
<223> OTHER INFORMATION: primer

<400> SEQUENCE: 34
agtccttagg tagtggctta gtccctggaa gctc                                34

<210> SEQ ID NO 35
<211> LENGTH: 52
<212> TYPE: DNA
<213> ORGANISM: Artificial Sequence
<220> FEATURE:
<223> OTHER INFORMATION: probe

<400> SEQUENCE: 35
gtaatacgac tcactatagg gccctgacgg tccttcctga gggaatcttc ac            52

<210> SEQ ID NO 36
<211> LENGTH: 50
<212> TYPE: DNA
<213> ORGANISM: Artificial Sequence
<220> FEATURE:
<223> OTHER INFORMATION: probe

<400> SEQUENCE: 36
gtaatacgac tcactatagg gcctgggaag ttggtcatgg ccactccagc               50

<210> SEQ ID NO 37
<211> LENGTH: 8
<212> TYPE: PRT
<213> ORGANISM: Artificial Sequence
<220> FEATURE:
<223> OTHER INFORMATION: FLAG tag

<400> SEQUENCE: 37

Asp Tyr Lys Asp Asp Asp Asp Lys
1               5

<210> SEQ ID NO 38
<211> LENGTH: 4
<212> TYPE: PRT
<213> ORGANISM: Artificial Sequence
<220> FEATURE:
<223> OTHER INFORMATION: motif

<400> SEQUENCE: 38

Tyr Gln Arg Leu
1
```

<210> SEQ ID NO 39
<211> LENGTH: 19
<212> TYPE: PRT
<213> ORGANISM: Artificial Sequence
<220> FEATURE:
<223> OTHER INFORMATION: antigen

<400> SEQUENCE: 39

Glu Gln Phe His Lys Tyr Leu Pro Trp Phe Leu Asn Asp Pro Pro Asn
1               5                   10                  15
Ile Arg Cys

<210> SEQ ID NO 40
<211> LENGTH: 16
<212> TYPE: PRT
<213> ORGANISM: Artificial Sequence
<220> FEATURE:
<223> OTHER INFORMATION: antigen

<400> SEQUENCE: 40

Glu Ala Phe Tyr Gln Arg Ser Phe Ala Glu Lys Ala Tyr Glu Ser Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: antigen

<400> SEQUENCE: 41

Gly Gln Thr Ser Leu Val Asp Trp Lys Asp His Phe Leu Tyr Cys
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: antigen

<400> SEQUENCE: 42

Cys Ala Asn Ala Pro Leu Thr Phe Lys Asp Gly Thr Ala Leu Ala Leu
1               5                   10                  15
Ser

<210> SEQ ID NO 43
<211> LENGTH: 5092
<212> TYPE: DNA
<213> ORGANISM: Homo sapiens
<220> FEATURE:
<221> NAME/KEY: CDS
<222> LOCATION: (57)..(4136)
<223> OTHER INFORMATION:

<400> SEQUENCE: 43
cttggctgtt cctgaggcct ggcctggctc ccgctgacc ccttcccaga cctggg atg      59
                                                              Met
                                                              1 gcg gag gcc ggc ctg agg ggc tgg ctg ctg tgg gcc ctg ctc ctg cgc      107
Ala Glu Ala Gly Leu Arg Gly Trp Leu Leu Trp Ala Leu Leu Leu Arg
        5                   10                  15 ttg gcc cag agt gag cct tac aca acc atc cac cag cct ggc tac tgc      155
Leu Ala Gln Ser Glu Pro Tyr Thr Thr Ile His Gln Pro Gly Tyr Cys -continued

```
             20                  25                  30
gcc ttc tat gac gaa tgt ggg aag aac cca gag ctg tct gga agc ctc     203
Ala Phe Tyr Asp Glu Cys Gly Lys Asn Pro Glu Leu Ser Gly Ser Leu
 35                  40                  45 atg aca ctc tcc aac gtg tcc tgc ctg tcc aac acg ccg gcc cgc aag     251
Met Thr Leu Ser Asn Val Ser Cys Leu Ser Asn Thr Pro Ala Arg Lys
 50                  55                  60                  65 atc aca ggt gat cac ctg atc cta tta cag aag atc tgc ccc cgc ctc     299
Ile Thr Gly Asp His Leu Ile Leu Leu Gln Lys Ile Cys Pro Arg Leu
                 70                  75                  80 tac acc ggc ccc aac acc caa gcc tgc tgc tcc gcc aag cag ctg gta     347
Tyr Thr Gly Pro Asn Thr Gln Ala Cys Cys Ser Ala Lys Gln Leu Val
             85                  90                  95 tca ctg gaa gcg agt ctg tcg atc acc aag gcc ctc ctc acc cgc tgc     395
Ser Leu Glu Ala Ser Leu Ser Ile Thr Lys Ala Leu Leu Thr Arg Cys
            100                 105                 110 cca gcc tgc tct gac aat ttt gtg aac ctg cac tgc cac aac acg tgc     443
Pro Ala Cys Ser Asp Asn Phe Val Asn Leu His Cys His Asn Thr Cys
        115                 120                 125 agc ccc aat cag agc ctc ttc atc aat gtg acc cgc gtg gcc cag cta     491
Ser Pro Asn Gln Ser Leu Phe Ile Asn Val Thr Arg Val Ala Gln Leu
130                 135                 140                 145 ggg gct gga caa ctc cca gct gtg gtg gcc tat gag gcc ttc tac cag     539
Gly Ala Gly Gln Leu Pro Ala Val Val Ala Tyr Glu Ala Phe Tyr Gln
                150                 155                 160 cat agc ttt gcc gag cag agc tat gac tcc tgc agc cgt gtg cgc gtc     587
His Ser Phe Ala Glu Gln Ser Tyr Asp Ser Cys Ser Arg Val Arg Val
            165                 170                 175 cct gca gct gcc acg ctg gct gtg ggc acc atg tgt ggc gtg tat ggc     635
Pro Ala Ala Ala Thr Leu Ala Val Gly Thr Met Cys Gly Val Tyr Gly
        180                 185                 190 tct gcc ctt tgc aat gcc cag cgc tgg ctc aac ttc cag gga gac aca     683
Ser Ala Leu Cys Asn Ala Gln Arg Trp Leu Asn Phe Gln Gly Asp Thr
    195                 200                 205 ggc aat ggt ctg gcc cca ctg gac atc acc ttc cac ctc ttg gag cct     731
Gly Asn Gly Leu Ala Pro Leu Asp Ile Thr Phe His Leu Leu Glu Pro
210                 215                 220                 225 ggc cag gcc gtg ggg agt ggg att cag cct ctg aat gag ggg gtt gca     779
Gly Gln Ala Val Gly Ser Gly Ile Gln Pro Leu Asn Glu Gly Val Ala
                230                 235                 240 cgt tgc aat gag tcc caa ggt gac gac gtg gcg acc tgc tcc tgc caa     827
Arg Cys Asn Glu Ser Gln Gly Asp Asp Val Ala Thr Cys Ser Cys Gln
            245                 250                 255 gac tgt gct gca tcc tgt cct gcc ata gcc cgc ccc cag gcc ctc gac     875
Asp Cys Ala Ala Ser Cys Pro Ala Ile Ala Arg Pro Gln Ala Leu Asp
        260                 265                 270 tcc acc ttc tac ctg ggc cag atg ccg ggc agt ctg gtc ctc atc atc     923
Ser Thr Phe Tyr Leu Gly Gln Met Pro Gly Ser Leu Val Leu Ile Ile
    275                 280                 285 atc ctc tgc tct gtc ttc gct gtg gtc acc atc ctg ctt gtg gga ttc     971
Ile Leu Cys Ser Val Phe Ala Val Val Thr Ile Leu Leu Val Gly Phe
290                 295                 300                 305 cgt gtg gcc ccc gcc agg gac aaa agc aag atg gtg gac ccc aag aag    1019
Arg Val Ala Pro Ala Arg Asp Lys Ser Lys Met Val Asp Pro Lys Lys
                310                 315                 320 ggc acc agc ctc tct gac aag ctc agc ttc tcc acc cac acc ctc ctt    1067
Gly Thr Ser Leu Ser Asp Lys Leu Ser Phe Ser Thr His Thr Leu Leu
            325                 330                 335 ggc cag ttc ttc cag ggc tgg ggc acg tgg gtg gct tcg tgg cct ctg    1115
```

```
Gly Gln Phe Phe Gln Gly Trp Gly Thr Trp Val Ala Ser Trp Pro Leu
        340                 345                 350 acc atc ttg gtg cta tct gtc atc ccg gtg gtg gcc ttg gca gcg ggc    1163
Thr Ile Leu Val Leu Ser Val Ile Pro Val Val Ala Leu Ala Ala Gly
355                 360                 365 ctg gtc ttt aca gaa ctc act acg gac ccc gtg gag ctg tgg tcg gcc    1211
Leu Val Phe Thr Glu Leu Thr Thr Asp Pro Val Glu Leu Trp Ser Ala
370                 375                 380                 385 ccc aac agc caa gcc cgg agt gag aaa gct ttc cat gac cag cat ttc    1259
Pro Asn Ser Gln Ala Arg Ser Glu Lys Ala Phe His Asp Gln His Phe
                390                 395                 400 ggc ccc ttc ttc cga acc aac cag gtg atc ctg acg gct cct aac cgg    1307
Gly Pro Phe Phe Arg Thr Asn Gln Val Ile Leu Thr Ala Pro Asn Arg
        405                 410                 415 tcc agc tac agg tat gac tct ctg ctg ctg ggg ccc aag aac ttc agc    1355
Ser Ser Tyr Arg Tyr Asp Ser Leu Leu Leu Gly Pro Lys Asn Phe Ser
        420                 425                 430 gga atc ctg gac ctg gac ttg ctg ctg gag cta gag ctg cag gag        1403
Gly Ile Leu Asp Leu Asp Leu Leu Leu Glu Leu Glu Leu Gln Glu
435                 440                 445 agg ctg cgg cac ctc cag gta tgg tcg ccc gaa gca cag cgc aac atc    1451
Arg Leu Arg His Leu Gln Val Trp Ser Pro Glu Ala Gln Arg Asn Ile
450                 455                 460                 465 tcc ctg cag gac atc tgc tac gcc ccc ctc aat ccg gac aat acc agt    1499
Ser Leu Gln Asp Ile Cys Tyr Ala Pro Leu Asn Pro Asp Asn Thr Ser
                470                 475                 480 ctc tac gac tgc tgc atc aac agc ctc ctg cag tat ttc cag aac aac    1547
Leu Tyr Asp Cys Cys Ile Asn Ser Leu Leu Gln Tyr Phe Gln Asn Asn
                485                 490                 495 cgc acg ctc ctg ctc aca gcc aac cag aca ctg atg ggg cag acc        1595
Arg Thr Leu Leu Leu Thr Ala Asn Gln Thr Leu Met Gly Gln Thr
        500                 505                 510 tcc caa gtc gac tgg aag gac cat ttt ctg tac tgt gcc aat gcc ccg    1643
Ser Gln Val Asp Trp Lys Asp His Phe Leu Tyr Cys Ala Asn Ala Pro
515                 520                 525 ctc acc ttc aag gat ggc aca gcc ctg gcc ctg agc tgc atg gct gac    1691
Leu Thr Phe Lys Asp Gly Thr Ala Leu Ala Leu Ser Cys Met Ala Asp
530                 535                 540                 545 tac ggg gcc cct gtc ttc ccc ttc ctt gcc att ggg ggg tac aaa gga    1739
Tyr Gly Ala Pro Val Phe Pro Phe Leu Ala Ile Gly Gly Tyr Lys Gly
                550                 555                 560 aag gac tat tct gag gca gag gcc ctg atc atg acg ttc tcc ctc aac    1787
Lys Asp Tyr Ser Glu Ala Glu Ala Leu Ile Met Thr Phe Ser Leu Asn
                565                 570                 575 aat tac cct gcc ggg gac ccc cgt ctg gcc cag gcc aag ctg tgg gag    1835
Asn Tyr Pro Ala Gly Asp Pro Arg Leu Ala Gln Ala Lys Leu Trp Glu
                580                 585                 590 gag gcc ttc tta gag gaa atg cga gcc ttc cag cgt cgg atg gct ggc    1883
Glu Ala Phe Leu Glu Glu Met Arg Ala Phe Gln Arg Arg Met Ala Gly
        595                 600                 605 atg ttc cag gtc acg ttc atg gct gag cgc tct ctg gaa gac gag atc    1931
Met Phe Gln Val Thr Phe Met Ala Glu Arg Ser Leu Glu Asp Glu Ile
610                 615                 620                 625 aat cgc acc aca gct gaa gac ctg ccc atc ttt gcc acc agc tac att    1979
Asn Arg Thr Thr Ala Glu Asp Leu Pro Ile Phe Ala Thr Ser Tyr Ile
                630                 635                 640 gtc ata ttc ctg tac atc tct ctg gcc ctg ggc agc tat tcc agc tgg    2027
Val Ile Phe Leu Tyr Ile Ser Leu Ala Leu Gly Ser Tyr Ser Ser Trp
        645                 650                 655
```

```
                                                      -continued
agc cga gtg atg gtg gac tcc aag gcc acg ctg ggc ctc ggc ggg gtg      2075
Ser Arg Val Met Val Asp Ser Lys Ala Thr Leu Gly Leu Gly Gly Val
        660                 665                 670 gcc gtg gtc ctg gga gca gtc atg gct gcc atg ggc ttc ttc tcc tac      2123
Ala Val Val Leu Gly Ala Val Met Ala Ala Met Gly Phe Phe Ser Tyr
675                 680                 685 ttg ggt atc cgc tcc tcc ctg gtc atc ctg caa gtg gtt cct ttc ctg      2171
Leu Gly Ile Arg Ser Ser Leu Val Ile Leu Gln Val Val Pro Phe Leu
690                 695                 700                 705 gtg ctg tcc gtg ggg gct gat aac atc ttc atc ttt gtt ctc gag tac      2219
Val Leu Ser Val Gly Ala Asp Asn Ile Phe Ile Phe Val Leu Glu Tyr
            710                 715                 720 cag agg ctg ccc cgg agg cct ggg gag cca cga gag gtc cac att ggg      2267
Gln Arg Leu Pro Arg Arg Pro Gly Glu Pro Arg Glu Val His Ile Gly
        725                 730                 735 cga gcc cta ggc agg gtg gct ccc agc atg ctg ttg tgc agc ctc tct      2315
Arg Ala Leu Gly Arg Val Ala Pro Ser Met Leu Leu Cys Ser Leu Ser
    740                 745                 750 gag gcc atc tgc ttc ttc cta ggg gcc ctg acc ccc atg cca gct gtg      2363
Glu Ala Ile Cys Phe Phe Leu Gly Ala Leu Thr Pro Met Pro Ala Val
755                 760                 765 cgg acc ttt gcc ctg acc tct ggc ctt gca gtg atc ctt gac ttc ctc      2411
Arg Thr Phe Ala Leu Thr Ser Gly Leu Ala Val Ile Leu Asp Phe Leu
770                 775                 780                 785 ctg cag atg tca gcc ttt gtg gcc ctg ctc tcc ctg gac agc aag agg      2459
Leu Gln Met Ser Ala Phe Val Ala Leu Leu Ser Leu Asp Ser Lys Arg
            790                 795                 800 cag gag gcc tcc cgg ttg gac gtc tgc tgc tgt gtc aag ccc cag gag      2507
Gln Glu Ala Ser Arg Leu Asp Val Cys Cys Cys Val Lys Pro Gln Glu
        805                 810                 815 ctg ccc ccg cct ggc cag gga gag ggg ctc ctg ctt ggc ttc ttc caa      2555
Leu Pro Pro Pro Gly Gln Gly Glu Gly Leu Leu Leu Gly Phe Phe Gln
    820                 825                 830 aag gct tat gcc ccc ttc ctg ctg cac tgg atc act cga ggt gtt gtg      2603
Lys Ala Tyr Ala Pro Phe Leu Leu His Trp Ile Thr Arg Gly Val Val
835                 840                 845 ctg ctg ctg ttt ctc gcc ctg ttc gga gtg agc ctc tac tcc atg tgc      2651
Leu Leu Leu Phe Leu Ala Leu Phe Gly Val Ser Leu Tyr Ser Met Cys
850                 855                 860                 865 cac atc agc gtg gga ctg gac cag gag ctg gcc ctg ccc aag gac tcg      2699
His Ile Ser Val Gly Leu Asp Gln Glu Leu Ala Leu Pro Lys Asp Ser
            870                 875                 880 tac ctg ctt gac tat ttc ctc ttt ctg aac cgc tac ttc gag gtg ggg      2747
Tyr Leu Leu Asp Tyr Phe Leu Phe Leu Asn Arg Tyr Phe Glu Val Gly
        885                 890                 895 gcc ccg gtg tac ttt gtt acc acc ttg ggc tac aac ttc tcc agc gag      2795
Ala Pro Val Tyr Phe Val Thr Thr Leu Gly Tyr Asn Phe Ser Ser Glu
    900                 905                 910 gct ggg atg aat gcc atc tgc tcc agt gca ggc tgc aac aac ttc tcc      2843
Ala Gly Met Asn Ala Ile Cys Ser Ser Ala Gly Cys Asn Asn Phe Ser
915                 920                 925 ttc acc cag aag atc cag tat gcc aca gag ttc cct gag cag tct tac      2891
Phe Thr Gln Lys Ile Gln Tyr Ala Thr Glu Phe Pro Glu Gln Ser Tyr
930                 935                 940                 945 ctg gcc atc cct gcc tcc tcc tgg gtg gat gac ttc att gac tgg ctg      2939
Leu Ala Ile Pro Ala Ser Ser Trp Val Asp Asp Phe Ile Asp Trp Leu
            950                 955                 960 acc ccg tcc tcc tgc tgc cgc ctt tat ata tct ggc ccc aat aag gac      2987
Thr Pro Ser Ser Cys Cys Arg Leu Tyr Ile Ser Gly Pro Asn Lys Asp
        965                 970                 975
```

| | | |
|---|---|---|
| aag ttc tgc ccc tcg acc gtc aac tct ctg aac tgc cta aag aac tgc<br>Lys Phe Cys Pro Ser Thr Val Asn Ser Leu Asn Cys Leu Lys Asn Cys<br>980                 985                 990 | | 3035 |
| atg agc atc acg atg ggc tct gtg agg ccc tcg gtg gag cag ttc cat<br>Met Ser Ile Thr Met Gly Ser Val Arg Pro Ser Val Glu Gln Phe His<br>995                 1000               1005 | | 3083 |
| aag tat ctt ccc tgg ttc ctg aac gac cgg ccc aac atc aaa tgt<br>Lys Tyr Leu Pro Trp Phe Leu Asn Asp Arg Pro Asn Ile Lys Cys<br>1010               1015             1020 | | 3128 |
| ccc aaa ggc ggc ctg gca gca tac agc acc tct gtg aac ttg act<br>Pro Lys Gly Gly Leu Ala Ala Tyr Ser Thr Ser Val Asn Leu Thr<br>1025               1030             1035 | | 3173 |
| tca gat ggc cag gtt tta gac aca gtt gcc att ctg tca ccc agg<br>Ser Asp Gly Gln Val Leu Asp Thr Val Ala Ile Leu Ser Pro Arg<br>1040               1045             1050 | | 3218 |
| ctg gag tac agt ggc aca atc tcg gct cac tgc aac ctc tac ctc<br>Leu Glu Tyr Ser Gly Thr Ile Ser Ala His Cys Asn Leu Tyr Leu<br>1055               1060             1065 | | 3263 |
| ctg gat tca gcc tcc agg ttc atg gcc tat cac aag ccc ctg aaa<br>Leu Asp Ser Ala Ser Arg Phe Met Ala Tyr His Lys Pro Leu Lys<br>1070               1075             1080 | | 3308 |
| aac tca cag gat tac aca gaa gct ctg cgg gca gct cga gag ctg<br>Asn Ser Gln Asp Tyr Thr Glu Ala Leu Arg Ala Ala Arg Glu Leu<br>1085               1090             1095 | | 3353 |
| gca gcc aac atc act gct gac ctg cgg aaa gtg cct gga aca gac<br>Ala Ala Asn Ile Thr Ala Asp Leu Arg Lys Val Pro Gly Thr Asp<br>1100               1105             1110 | | 3398 |
| ccg gct ttt gag gtc ttc ccc tac acg atc acc aat gtg ttt tat<br>Pro Ala Phe Glu Val Phe Pro Tyr Thr Ile Thr Asn Val Phe Tyr<br>1115               1120             1125 | | 3443 |
| gag cag tac ctg acc atc ctc cct gag ggg ctc ttc atg ctc agc<br>Glu Gln Tyr Leu Thr Ile Leu Pro Glu Gly Leu Phe Met Leu Ser<br>1130               1135             1140 | | 3488 |
| ctc tgc ctt gtg ccc acc ttc gct gtc tcc tgc ctc ctg ctg ggc<br>Leu Cys Leu Val Pro Thr Phe Ala Val Ser Cys Leu Leu Leu Gly<br>1145               1150             1155 | | 3533 |
| ctg gac ctg cgc tcc ggc ctc ctc aac ctg ctc tcc att gtc atg<br>Leu Asp Leu Arg Ser Gly Leu Leu Asn Leu Leu Ser Ile Val Met<br>1160               1165             1170 | | 3578 |
| atc ctc gtg gac act gtc ggc ttc atg gcc ctg tgg ggc atc agt<br>Ile Leu Val Asp Thr Val Gly Phe Met Ala Leu Trp Gly Ile Ser<br>1175               1180             1185 | | 3623 |
| tac aat gct gtg tcc ctc atc aac ctg gtc tcg gcg gtg ggc atg<br>Tyr Asn Ala Val Ser Leu Ile Asn Leu Val Ser Ala Val Gly Met<br>1190               1195             1200 | | 3668 |
| tct gtg gag ttt gtg tcc cac att acc cgc tcc ttt gcc atc agc<br>Ser Val Glu Phe Val Ser His Ile Thr Arg Ser Phe Ala Ile Ser<br>1205               1210             1215 | | 3713 |
| acc aag ccc acc tgg ctg gag agg gcc aaa gag gcc acc atc tct<br>Thr Lys Pro Thr Trp Leu Glu Arg Ala Lys Glu Ala Thr Ile Ser<br>1220               1225             1230 | | 3758 |
| atg gga agt gcg gtg ttt gca ggt gtg gcc atg acc aac ctg cct<br>Met Gly Ser Ala Val Phe Ala Gly Val Ala Met Thr Asn Leu Pro<br>1235               1240             1245 | | 3803 |
| ggc atc ctt gtc ctg ggc ctc gcc aag gcc cag ctc att cag atc<br>Gly Ile Leu Val Leu Gly Leu Ala Lys Ala Gln Leu Ile Gln Ile<br>1250               1255             1260 | | 3848 |
| ttc ttc ttc cgc ctc aac ctc ctg atc act ctg ctg ggc ctg ctg<br>Phe Phe Phe Arg Leu Asn Leu Leu Ile Thr Leu Leu Gly Leu Leu | | 3893 |

| | |
|---|---|
| 1265 1270 1275 | |
| cat ggc ttg gtc ttc ctg ccc gtc atc ctc agc tac gtg ggg cct<br>His Gly Leu Val Phe Leu Pro Val Ile Leu Ser Tyr Val Gly Pro<br>1280          1285                1290 | 3938 |
| gac gtt aac ccg gct ctg gca ctg gag cag aag cgg gct gag gag<br>Asp Val Asn Pro Ala Leu Ala Leu Glu Gln Lys Arg Ala Glu Glu<br>1295          1300                1305 | 3983 |
| gcg gtg gca gca gtc atg gtg gcc tct tgc cca aat cac ccc tcc<br>Ala Val Ala Ala Val Met Val Ala Ser Cys Pro Asn His Pro Ser<br>1310          1315                1320 | 4028 |
| cga gtc tcc aca gct gac aac atc tat gtc aac cac agc ttt gaa<br>Arg Val Ser Thr Ala Asp Asn Ile Tyr Val Asn His Ser Phe Glu<br>1325          1330                1335 | 4073 |
| ggt tct atc aaa ggt gct ggt gcc atc agc aac ttc ttg ccc aac<br>Gly Ser Ile Lys Gly Ala Gly Ala Ile Ser Asn Phe Leu Pro Asn<br>1340          1345                1350 | 4118 |
| aat ggg cgg cag ttc tga tacagccaga ggccctgtct aggctctatg<br>Asn Gly Arg Gln Phe<br>1355 | 4166 |
| gccctgaacc aaagggttat ggggatcttc cttgtgactg ccccttgaca cacgccctcc | 4226 |
| tcaaatccta ggggaggcca ttcccatgag actgcctgtc actggaggat ggcctgctct | 4286 |
| tgaggtatcc aggcagcacc actgatggct cctctgctcc catagtgggt ccccagtttc | 4346 |
| caagtcacct aggccttggg cagtgcctcc tcctgggcct gggtctggaa gttggcagga | 4406 |
| acagacacac tccatgtttg tcccacactc actcactttc ctaggagccc acttctcatc | 4466 |
| caacttttcc cttctcagtt cctctctcga aagtcttaat tctgtgtcag taagtcttta | 4526 |
| acacgtagca gtgtccctga gaacacagac aatgaccact accctgggtg tgatatcaca | 4586 |
| ggaggccaga gagaggcaaa ggctcaggcc aagagccaac gctgtgggag gccggtcggc | 4646 |
| agccactccc tccagggcgc acctgcaggt ctgccatcca cggccttttc tggcaagaga | 4706 |
| agggcccagg aaggatgctc tcataaggcc caggaaggat gctctcataa gcaccttggt | 4766 |
| catggattag cccctcctgg aaaatggtgt tgggtttggt ctccagctcc aatacttatt | 4826 |
| aaggctgttg ctgccagtca aggccaccca ggagtctgaa ggctgggagc tcttggggct | 4886 |
| gggctggtcc tcccatcttc acctcgggcc tggatcccag gcctcaaacc agcccaaccc | 4946 |
| gagcttttgg acagctctcc agaagcatga actgcagtgg agatgaagat cctggctctg | 5006 |
| tgctgtgcac ataggtgttt aataaacatt tgttggcaga aaaaaaaaa aaaaaaaaa | 5066 |
| aaaaaaaaa aaaaaaaaa aaaaa | 5092 |

<210> SEQ ID NO 44
<211> LENGTH: 1359
<212> TYPE: PRT
<213> ORGANISM: Homo sapiens

<400> SEQUENCE: 44

Met Ala Glu Ala Gly Leu Arg Gly Trp Leu Leu Trp Ala Leu Leu Leu
1               5                   10                  15

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
        35                  40                  45

Leu Met Thr Leu Ser Asn Val Ser Cys Leu Ser Asn Thr Pro Ala Arg
    50                  55                  60

Lys Ile Thr Gly Asp His Leu Ile Leu Leu Gln Lys Ile Cys Pro Arg

```
              65                  70                  75                  80
Leu Tyr Thr Gly Pro Asn Thr Gln Ala Cys Cys Ser Ala Lys Gln Leu
                    85                  90                  95
Val Ser Leu Glu Ala Ser Leu Ser Ile Thr Lys Ala Leu Leu Thr Arg
                    100                 105                 110
Cys Pro Ala Cys Ser Asp Asn Phe Val Asn Leu His Cys His Asn Thr
                    115                 120                 125
Cys Ser Pro Asn Gln Ser Leu Phe Ile Asn Val Thr Arg Val Ala Gln
                    130                 135                 140
Leu Gly Ala Gly Gln Leu Pro Ala Val Val Ala Tyr Glu Ala Phe Tyr
145                 150                 155                 160
Gln His Ser Phe Ala Glu Gln Ser Tyr Asp Ser Cys Ser Arg Val Arg
                    165                 170                 175
Val Pro Ala Ala Ala Thr Leu Ala Val Gly Thr Met Cys Gly Val Tyr
                    180                 185                 190
Gly Ser Ala Leu Cys Asn Ala Gln Arg Trp Leu Asn Phe Gln Gly Asp
                    195                 200                 205
Thr Gly Asn Gly Leu Ala Pro Leu Asp Ile Thr Phe His Leu Leu Glu
                    210                 215                 220
Pro Gly Gln Ala Val Gly Ser Gly Ile Gln Pro Leu Asn Glu Gly Val
225                 230                 235                 240
Ala Arg Cys Asn Glu Ser Gln Gly Asp Asp Val Ala Thr Cys Ser Cys
                    245                 250                 255
Gln Asp Cys Ala Ala Ser Cys Pro Ala Ile Ala Arg Pro Gln Ala Leu
                    260                 265                 270
Asp Ser Thr Phe Tyr Leu Gly Gln Met Pro Gly Ser Leu Val Leu Ile
                    275                 280                 285
Ile Ile Leu Cys Ser Val Phe Ala Val Val Thr Ile Leu Leu Val Gly
                    290                 295                 300
Phe Arg Val Ala Pro Ala Arg Asp Lys Ser Lys Met Val Asp Pro Lys
305                 310                 315                 320
Lys Gly Thr Ser Leu Ser Asp Lys Leu Ser Phe Ser Thr His Thr Leu
                    325                 330                 335
Leu Gly Gln Phe Phe Gln Gly Trp Gly Thr Trp Val Ala Ser Trp Pro
                    340                 345                 350
Leu Thr Ile Leu Val Leu Ser Val Ile Pro Val Val Ala Leu Ala Ala
                    355                 360                 365
Gly Leu Val Phe Thr Glu Leu Thr Thr Asp Pro Val Glu Leu Trp Ser
                    370                 375                 380
Ala Pro Asn Ser Gln Ala Arg Ser Glu Lys Ala Phe His Asp Gln His
385                 390                 395                 400
Phe Gly Pro Phe Phe Arg Thr Asn Gln Val Ile Leu Thr Ala Pro Asn
                    405                 410                 415
Arg Ser Ser Tyr Arg Tyr Asp Ser Leu Leu Gly Pro Lys Asn Phe
                    420                 425                 430
Ser Gly Ile Leu Asp Leu Asp Leu Leu Glu Leu Leu Glu Leu Gln
                    435                 440                 445
Glu Arg Leu Arg His Leu Gln Val Trp Ser Pro Glu Ala Gln Arg Asn
                    450                 455                 460
Ile Ser Leu Gln Asp Ile Cys Tyr Ala Pro Leu Asn Pro Asp Asn Thr
465                 470                 475                 480
Ser Leu Tyr Asp Cys Cys Ile Asn Ser Leu Leu Gln Tyr Phe Gln Asn
                    485                 490                 495
```

-continued

```
Asn Arg Thr Leu Leu Leu Thr Ala Asn Gln Thr Leu Met Gly Gln
        500                 505                 510
Thr Ser Gln Val Asp Trp Lys Asp His Phe Leu Tyr Cys Ala Asn Ala
        515                 520                 525
Pro Leu Thr Phe Lys Asp Gly Thr Ala Leu Ala Leu Ser Cys Met Ala
        530                 535                 540
Asp Tyr Gly Ala Pro Val Phe Pro Phe Leu Ala Ile Gly Gly Tyr Lys
545                 550                 555                 560
Gly Lys Asp Tyr Ser Glu Ala Glu Ala Leu Ile Met Thr Phe Ser Leu
                565                 570                 575
Asn Asn Tyr Pro Ala Gly Asp Pro Arg Leu Ala Gln Ala Lys Leu Trp
                580                 585                 590
Glu Glu Ala Phe Leu Glu Glu Met Arg Ala Phe Gln Arg Arg Met Ala
                595                 600                 605
Gly Met Phe Gln Val Thr Phe Met Ala Glu Arg Ser Leu Glu Asp Glu
                610                 615                 620
Ile Asn Arg Thr Thr Ala Glu Asp Leu Pro Ile Phe Ala Thr Ser Tyr
625                 630                 635                 640
Ile Val Ile Phe Leu Tyr Ile Ser Leu Ala Leu Gly Ser Tyr Ser Ser
                645                 650                 655
Trp Ser Arg Val Met Val Asp Ser Lys Ala Thr Leu Gly Leu Gly Gly
                660                 665                 670
Val Ala Val Leu Gly Ala Val Met Ala Ala Met Gly Phe Phe Ser
                675                 680                 685
Tyr Leu Gly Ile Arg Ser Ser Leu Val Ile Leu Gln Val Val Pro Phe
                690                 695                 700
Leu Val Leu Ser Val Gly Ala Asp Asn Ile Phe Ile Phe Val Leu Glu
705                 710                 715                 720
Tyr Gln Arg Leu Pro Arg Arg Pro Gly Glu Pro Arg Glu Val His Ile
                725                 730                 735
Gly Arg Ala Leu Gly Arg Val Ala Pro Ser Met Leu Leu Cys Ser Leu
                740                 745                 750
Ser Glu Ala Ile Cys Phe Phe Leu Gly Ala Leu Thr Pro Met Pro Ala
                755                 760                 765
Val Arg Thr Phe Ala Leu Thr Ser Gly Leu Ala Val Ile Leu Asp Phe
                770                 775                 780
Leu Leu Gln Met Ser Ala Phe Val Ala Leu Leu Ser Leu Asp Ser Lys
785                 790                 795                 800
Arg Gln Glu Ala Ser Arg Leu Asp Val Cys Cys Val Lys Pro Gln
                805                 810                 815
Glu Leu Pro Pro Pro Gly Gln Gly Glu Gly Leu Leu Leu Gly Phe Phe
                820                 825                 830
Gln Lys Ala Tyr Ala Pro Phe Leu Leu His Trp Ile Thr Arg Gly Val
                835                 840                 845
Val Leu Leu Leu Phe Leu Ala Leu Phe Gly Val Ser Leu Tyr Ser Met
                850                 855                 860
Cys His Ile Ser Val Gly Leu Asp Gln Glu Leu Ala Leu Pro Lys Asp
865                 870                 875                 880
Ser Tyr Leu Leu Asp Tyr Phe Leu Phe Leu Asn Arg Tyr Phe Glu Val
                885                 890                 895
Gly Ala Pro Val Tyr Phe Val Thr Thr Leu Gly Tyr Asn Phe Ser Ser
                900                 905                 910
```

```
Glu Ala Gly Met Asn Ala Ile Cys Ser Ser Ala Gly Cys Asn Asn Phe
        915                 920                 925

Ser Phe Thr Gln Lys Ile Gln Tyr Ala Thr Glu Phe Pro Glu Gln Ser
        930                 935                 940

Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
                965                 970                 975

Asp Lys Phe Cys Pro Ser Thr Val Asn Ser Leu Asn Cys Leu Lys Asn
                980                 985                 990

Cys Met Ser Ile Thr Met Gly Ser  Val Arg Pro Ser Val  Glu Gln Phe
        995                 1000                1005

His Lys  Tyr Leu Pro Trp Phe  Leu Asn Asp Arg Pro  Asn Ile Lys
    1010                1015                1020

Cys Pro  Lys Gly Gly Leu Ala  Ala Tyr Ser Thr Ser  Val Asn Leu
    1025                1030                1035

Thr Ser  Asp Gly Gln Val Leu  Asp Thr Val Ala Ile  Leu Ser Pro
    1040                1045                1050

Arg Leu  Glu Tyr Ser Gly Thr  Ile Ser Ala His Cys  Asn Leu Tyr
    1055                1060                1065

Leu Leu  Asp Ser Ala Ser Arg  Phe Met Ala Tyr His  Lys Pro Leu
    1070                1075                1080

Lys Asn  Ser Gln Asp Tyr Thr  Glu Ala Leu Arg Ala  Ala Arg Glu
    1085                1090                1095

Leu Ala  Ala Asn Ile Thr Ala  Asp Leu Arg Lys Val  Pro Gly Thr
    1100                1105                1110

Asp Pro  Ala Phe Glu Val Phe  Pro Tyr Thr Ile Thr  Asn Val Phe
    1115                1120                1125

Tyr Glu  Gln Tyr Leu Thr Ile  Leu Pro Glu Gly Leu  Phe Met Leu
    1130                1135                1140

Ser Leu  Cys Leu Val Pro Thr  Phe Ala Val Ser Cys  Leu Leu Leu
    1145                1150                1155

Gly Leu  Asp Leu Arg Ser Gly  Leu Leu Asn Leu Leu  Ser Ile Val
    1160                1165                1170

Met Ile  Leu Val Asp Thr Val  Gly Phe Met Ala Leu  Trp Gly Ile
    1175                1180                1185

Ser Tyr  Asn Ala Val Ser Leu  Ile Asn Leu Val Ser  Ala Val Gly
    1190                1195                1200

Met Ser  Val Glu Phe Val Ser  His Ile Thr Arg Ser  Phe Ala Ile
    1205                1210                1215

Ser Thr  Lys Pro Thr Trp Leu  Glu Arg Ala Lys Glu  Ala Thr Ile
    1220                1225                1230

Ser Met  Gly Ser Ala Val Phe  Ala Gly Val Ala Met  Thr Asn Leu
    1235                1240                1245

Pro Gly  Ile Leu Val Leu Gly  Leu Ala Lys Ala Gln  Leu Ile Gln
    1250                1255                1260

Ile Phe  Phe Phe Arg Leu Asn  Leu Leu Ile Thr Leu  Leu Gly Leu
    1265                1270                1275

Leu His  Gly Leu Val Phe Leu  Pro Val Ile Leu Ser  Tyr Val Gly
    1280                1285                1290

Pro Asp  Val Asn Pro Ala Leu  Ala Leu Glu Gln Lys  Arg Ala Glu
    1295                1300                1305

Glu Ala  Val Ala Ala Val Met  Val Ala Ser Cys Pro  Asn His Pro
```

|  | 1310 |  |  |  | 1315 |  |  |  | 1320 |  |  |
|---|---|---|---|---|---|---|---|---|---|---|---|

Ser Arg Val Ser Thr Ala Asp Asn Ile Tyr Val Asn His Ser Phe
    1325                           1330                           1335

Glu Gly Ser Ile Lys Gly Ala Gly Ala Ile Ser Asn Phe Leu Pro
    1340                           1345                           1350

Asn Asn Gly Arg Gln Phe
    1355

<210> SEQ ID NO 45
<211> LENGTH: 4471
<212> TYPE: DNA
<213> ORGANISM: Mus musculus

<400> SEQUENCE: 45

```
ggatcacttc ctggctctgg gatggcagct gcctggcagg gatggctgct ctgggccctg      60
ctcctgaatt cggcccaggg tgagctctac acacccactc acaaagctgg cttctgcacc     120
ttttatgaag agtgtgggaa gaacccagag ctttctggag gcctcacatc actatccaat     180
atctcctgct tgtctaatac cccagccccg ccatgtcaca ggtgaccacc tggctcttct     240
ccagcgcgtc tgtccccgcc tatacaatgg ccccaatgac acctatgcct gttgctctac     300
caagcagctg gtgtcattag acagtagcct gtctatcacc aaggccctcc ttacacgctg     360
cccggcatgc tctgaaaatt ttgtgagcat acactgtcat aatacctgca gccctgacca     420
gagcctcttc atcaatgtta ctcgcgtggt tcagcgggac cctggacagc ttcctgctgt     480
ggtggcctat gaggcctttt atcaacgcag ttttgcagag aaggcctatg agtcctgtag     540
ccgggtgcgc atccctgcag ctgcctcgct ggctgtgggc agcatgtgtg gagtgtatgg     600
ctctgccctc tgcaatgctc agcgcctggc tcaacttcca aggagacaca gggaatggcc     660
tggctccgct ggacatcacc ttccacctct tggagcctgg ccaggccctg gcagatggga     720
tgaagccact ggatgggaag atcaaaccct gcaatgagtc ccagggtgaa gactcggcag     780
cctgttcctg ccaggactgt gcagcatcct gccctgtcat ccctccgccc ccggccctgc     840
gcccttcttt ctacatgggt cgaatgccag gctggctggc tctcatcatc atcttcactg     900
ctgtctttgt attgctctct gttgtccttg tgtatctccg agtggcttcc aacaggaaca     960
agaacaagac agcaggctcc caggaagccc ccaacctccc tcgtaagcgc agattctcac    1020
ctcacactgt ccttggccgg ttcttcgaga gctggggaac aatggtggcc tcatggccac    1080
tcactgtctt ggcactgtcc ttcatagttg tgatagcctt gtcagtaggc ctgacctta    1140
tagaactcac cacagaccct gtggaactgt ggtcggcccc taaaagccaa gcccggaaag    1200
aaaaggcttt ccatgacgag catttggcc ccttcttccg aaccaaccag attttgtga    1260
cagctaagaa caggtccagc tacaagtacg actccctgct gctagggccc aagaacttca    1320
gtgggatcct atccctggac ttgctgcagg agctgttgga gctacaggag agacttcgac    1380
acctgcaagt gtggtcccat gaggcacagc gcaacatctc cctccaggac atctgctatg    1440
ctcccctcaa accgcataac accagcctca ctgactgctg tgtcaacagc tccttcaat    1500
acttccagaa caaccacaca ctcctgctgc tcacagccaa ccagactctg aatgccaga    1560
cctcctggt ggactggaag gaccatttcc tctactgtgc caatgcccct ctcacgtaca    1620
aagatggcac agccctggcc ctgagctgca tagctgacta cgggcgcct gtcttcccct    1680
tccttgctgt tgggggctac caagggacgg actactcgga ggcagaagcc ctgatcataa    1740
ccttctctat caataactac cccgctgatg atccccgcat ggcccacgcc aagctctggg    1800
```

```
aggaggcttt cttgaaggaa atgcaatcct tccagagaag cacagctgac aagttccaga   1860
ttgcgttctc agctgagcgt tctctggagg acgagatcaa tcgcactacc atccaggacc   1920
tgcctgtctt tgccatcagc taccttatcg tcttcctgta catctccctg gccctgggca   1980
gctactccag atggagccga gttgcggtgg attccaaggc tactctgggc ctaggtgggg   2040
tggctgttgt gctgggagca gtcgtggctg ccatgggctt ctactcctac ctgggtgtcc   2100
cctcctctct ggtcatcatt caagtggtac cttcctggt gctggctgtg ggagctgaca    2160
acatcttcat ctttgttctt gagtaccaga ggctgcctag gatgcccggg gagcagcgag   2220
aggctcacat tggccgcacc ctgggtagtg tggcccccag catgctgctg tgcagcctct   2280
ctgaggccat ctgcttcttt ctaggggccc tgacctccat gccagctgtg aggacctttg   2340
ccttgacctc tggcttagca atcatctttg acttcctgct ccagatgaca gcctttgtgg   2400
ccctgctctc cctggatagc aagaggcagg aggcctctcg ccccgacgtc gtgtgctgct   2460
tttcaagccg aaatctgccc ccaccgaaac aaaagaagg cctcttactt tgcttcttcc     2520
gcaagatata cactcccttc ctgctgcaca gattcatccg ccctgttgtg ctgctgctct   2580
ttctggtcct gtttggagca aacctctact taatgtgcaa catcagcgtg gggctggacc   2640
aggatctggc tctgcccaag gattcctacc tgatagacta cttcctcttt ctgaaccggt   2700
acttggaagt ggggcctcca gtgtactttg acaccacctc aggctacaac ttttccaccg   2760
aggcaggcat gaacgccatt tgctctagtg caggctgtga gagcttctcc ctaacccaga   2820
aaatccagta tgccagtgaa ttccctaatc agtcttatgt ggctattgct gcatcctcct   2880
gggtagatga cttcatcgac tggctgaccc catcctcctc ctgctgccgc atttataccc   2940 gtggcccccca taaagatgag ttctgtccct caacggatac ttccttcaac tgtctcaaaa   3000
actgcatgaa ccgcactctg ggtcccgtga gacccacaac agaacagtttt cataagtacc   3060 tgccctggtt cctgaatgat acgcccaaca tcagatgtct taaaggggggc ctagcagcgt   3120 atagaaccctc tgtgaatttg atctcagatg ccagattat agcctcccag ttcatggcct    3180
accacaagcc cttacggaac tcacaggact ttacagaagc tctccgggca tcccggttgc   3240
tagcagccaa catcacagct gaactacgga aggtgcctgg gacagatccc aactttgagg   3300 tcttcccctta cacgatctcc aatgtgttct accagcaata cctgacggtt ctccctgagg   3360
gaatcttcac tcttgctctc tgcttcgtgc ccaccttttgt ggtctgctac ctcctactgg   3420
gcctggacat acgctcaggc atcctcaacc tgctctccat cattatgatc ctcgtggaca   3480
ccatcggcct catggctgtg tggggtatca gctacaatgc tgtgtccctc atcaaccttg   3540
tcacggcagt gggcatgtct gtggagttcg tgtcccacat tacccggtcc tttgctgtaa   3600
gcaccaagcc tacccggctg gagagagcca aagatgctac tatcttcatg ggcagtgcgg   3660
tgtttgctgg agtggccatg accaacttcc cgggcatcct catcctgggc tttgctcagg   3720
cccagcttat ccagatttc ttcttccgcc tcaacctcct gatcacctg ctgggtctgc      3780 tacacggcct ggtcttcctg cccgttgtcc tcagctatct ggggccagat gttaaccaag   3840
ctctggtact ggaggagaaa ctagccactg aggcagccat ggtctcagag ccttcttgcc   3900
cacagtaccc cttcccggct gatgcaaaca ccagtgacct atgttaacta aggctttaat   3960
ccagaattta tccctgaaat taatgctgct agcagctctc tgcccaaaag tgaccaaaag   4020
ttctaatgga gtaggagctt gtccaggctc catggttctt gctgataagg ggccacgagg   4080
gtcttccctc tggttgtttc caaggcctgg ggaaagttgt tccagaaaaa aattgctggc   4140
attcttgtcc tgaggcagcc agcactggcc actttgttgt cataggtccc cgaggccatg   4200
```

```
atcagattac ctcctctgta aagagaatat cttgagtatt gtatgggatg tatcacatgt    4260
caattaaaaa ggccatggcc tatggcttag gcaggaaata gggtgtggaa catccaggag    4320
aagaaaggat tctgggataa aggacacttg ggaacgtgtg gcagtggtac ctgagcacag    4380
gtaattagcc atgtggcgaa atgtagatta atataaatgc atatctaagt tatgattcta    4440
gtctagctat atggccaagg tatttataaa t                                   4471
```

<210> SEQ ID NO 46
<211> LENGTH: 25
<212> TYPE: DNA
<213> ORGANISM: Artificial sequence
<220> FEATURE:
<223> OTHER INFORMATION: primer

<400> SEQUENCE: 46
atgttaggtg agtctgaacc taccc                                          25

<210> SEQ ID NO 47
<211> LENGTH: 25
<212> TYPE: DNA
<213> ORGANISM: Artificial sequence
<220> FEATURE:
<223> OTHER INFORMATION: primer

<400> SEQUENCE: 47
ggattgcatt tccttcaaga aagcc                                          25

<210> SEQ ID NO 48
<211> LENGTH: 25
<212> TYPE: DNA
<213> ORGANISM: Artificial sequence
<220> FEATURE:
<223> OTHER INFORMATION: primer

<400> SEQUENCE: 48
tatggctctg ccctctgcaa tgctc                                          25

<210> SEQ ID NO 49
<211> LENGTH: 28
<212> TYPE: DNA
<213> ORGANISM: Artificial sequence
<220> FEATURE:
<223> OTHER INFORMATION: primer

<400> SEQUENCE: 49
tcagcagcct ctgttccaca tacacttc                                       28

<210> SEQ ID NO 50
<211> LENGTH: 25
<212> TYPE: DNA
<213> ORGANISM: Artificial sequence
<220> FEATURE:
<223> OTHER INFORMATION: primer

<400> SEQUENCE: 50
gttccacagg gtctgtggtg agttc                                          25

<210> SEQ ID NO 51
<211> LENGTH: 3996
<212> TYPE: DNA
<213> ORGANISM: Homo sapiens
<220> FEATURE:
<221> NAME/KEY: misc_feature
<222> LOCATION: (1)..(3996)

-continued

<223> OTHER INFORMATION: n is g or a or t or c

<400> SEQUENCE: 51
atggcngarg cnggnytnmg nggntggytn ytntgggcny tnytnytnmg nytngcncar 60
wsngarccnt ayacnacnat hcaycarccn ggntaytgyg cnttytayga ygartgyggn 120
aaraayccng arytnwsngg nwsnytnatg acnytnwsna aygtnwsntg yytnwsnaay 180
acnccngcnm gnaarathac nggngaycay ytnathytny tncaraarat htgyccnmgn 240
ytntayacng gnccnaayac ncargcntgy tgywsngcna arcarytngt nwsnytngar 300
gcnwsnytnw snathacnaa rgcnytnytn acnmgntgyc cngcntgyws ngayaaytty 360
gtnaayytnc aytgycayaa yacntgywsn ccnaaycarw snytnttyat haaygtnacn 420
mgngtngcnc arytnggngc nggncarytn ccngcngtng tngcntayga rgcnttytay 480
carcaywsnt tygcngarca rwsntaygay wsntgywsnm gngtnmgngt nccngcngcn 540
gcnacnytng cngtnggnac natgtgyggn gtntayggnw sngcnytntg yaaygcncar 600
mgntggytna ayttycargg ngayacnggn aayggnytng cnccnytnga yathacntty 660
cayytnytng arccnggnca rgcngtnggn wsnggnathc arccnytnaa ygarggngtn 720
gcnmgntgya aygarwsnca rggngaygay gtngcnacnt gywsntgyca rgaytgygcn 780
gcnwsntgyc cngcnathgc nmgnccncar gcnytngayw snacnttyta yytnggncar 840
atgccnggnw snytngtnyt nathathath ytntgywsng tnttygcngt ngtnacnath 900
ytnytngtng gnttymgngt ngcnccngcn mgngayaarw snaaratggt ngayccnaar 960
aarggnacnw snytnwsnga yaarytnwsn ttywsnacnc ayacnytnyt nggncartty 1020
ttycarggnt ggggnacntg ggtngcnwsn tggccnytna cnathytngt nytnwsngtn 1080
athccngtng tngcnytngc ngcnggnytn gtnttyacng arytnacnac ngayccngtn 1140
garytntggw sngcnccnaa ywsncargcn mgnwsngara argcnttyca ygaycarcay 1200
ttyggnccnt tyttymgnac naaycargtn athytnacng cnccnaaymg nwsnwsntay 1260
mgntaygayw snytnytnyt nggnccnaar aayttywsng gnathytnga yytngayytn 1320
ytnytngary tnytngaryt ncargarmgn ytnmgncayy tncargtntg gwsnccngar 1380
gcncarmgna ayathwsnyt ncargayath tgytaygcnc cnytnaaycc ngayaayacn 1440
wsnytntayg aytgytgyat haaywsnytn ytncartayt tycaraayaa ymgnacnytn 1500
ytnytnytna cngcnaayca racnytnatg ggncaracnw sncargtnga ytggaargay 1560
cayttyytnt aytgygcnaa ygcnccnytn acnttyaarg ayggnacngc nytngcnytn 1620
wsntgyatgg cngaytaygg ngcnccngtn ttyccnttyy tngcnathgg nggntayaar 1680
ggnaargayt aywsngargc ngargcnytn athatgacnt tywsnytnaa yaaytayccn 1740
gcnggngayc cnmgnytngc ncargcnaar ytntgggarg argcnttyyt ngargaratg 1800
mgngcnttyc armgnmgnat ggcnggnatg ttycargtna cnttyacngc ngarmgnwsn 1860
ytngargayg arathaaymg nacnacngcn gargayytnc cnathttygc nacnwsntay 1920
athgtnatht tyytntayat hwsnytngcn ytnggnwsnt aywsnwsntg gwsnmgngtn 1980
atggtngayw snaargcnac nytnggnytn ggnggngtng cngtngtnyt nggngcngtn 2040

-continued atggcngcna tgggnttytt ywsntayytn ggnathmgnw snwsnytngt nathytncar 2100
gtngtnccnt tyytngtnyt nwsngtnggn gcngayaaya thttyathtt ygtnytngar 2160
taycarmgny tnccnmgnmg nccnggngar ccnmgngarg tncayathgg nmgngcnytn 2220
ggnmgngtng cnccnwsnat gytnytntgy wsnytnwsng argcnathtg yttyttyytn 2280
ggngcnytna cnccnatgcc ngcngtnmgn acnttygcny tnacnwsngg nytngcngtn 2340
athytngayt tyytnytnca ratgwsngcn ttygtngcny tnytnwsnyt ngaywsnaar 2400
mgncargarg cnwsnmgnyt ngaygtntgy tgytgygtna arccncarga rytnccnccn 2460
ccnggncarg gngarggnyt nytnytnggn ttyttycara argcntaygc nccnttyytn 2520
ytncaytgga thacnmgngg ngtngtnytn ytnytnttyy tngcnytntt yggngtnwsn 2580
ytntaywsna tgtgycayat hwsngtnggn ytngaycarg arytngcnyt nccnaargay 2640
wsntayytny tngaytaytt yytnttyytn aaymgntayt tygargtngg ngcnccngtn 2700
tayttygtna cnacnytngg ntayaaytty wsnwsngarg cnggnatgaa ygcnathtgy 2760
wsnwsngcng gntgyaayaa yttywsntty acncaraara thcartaygc nacngartty 2820
ccngarcarw sntayytngc nathccngcn wsnwsntggg tngaygaytt yathgaytgg 2880
ytnacnccnw snwsntgytg ymgnytntay athwsnggnc cnaayaarga yaarttytgy 2940
ccnwsnacng tnaaywsnyt naaytgyytn aaraaytgya tgwsnathac natgggnwsn 3000
gtnmgnccnw sngtngarca rttycayaar tayytnccnt ggttyytnaa ygaymgnccn 3060
aayathaart gyccnaargg nggnytngcn gcntaywsna cnwsngtnaa yytnacnwsn 3120
gayggncarg tnytngcnws nmgnttyatg gcntaycaya arccnytnaa raaywsncar 3180
gaytayacng argcnytnmg ngcngcnmgn garytngcng cnaayathac ngcngayytn 3240
mgnaargtnc cnggnacnga yccngcntty gargtnttyc cntayacnat hacnaaygtn 3300
ttytaygarc artayytnac nathytnccn garggnytnt tyatgytnws nytntgyytn 3360
gtnccnacnt tygcngtnws ntgyytnytn ytnggnytng ayytnmgnws nggnytnytn 3420
aayytnytnw snathgtnat gathytngtn gayacngtng gnttyatggc nytntgggay 3480
athwsntaya aygcngtnws nytnathaay ytngtnwsng cngtnggnat gwsngtngar 3540
ttygtnwsnc ayathacnmg nwsnttygcn athwsnacna arccnacntg gytngarmgn 3600
gcnaargarg cnacnathws natgggnwsn gcngtnttyg cnggngtngc natgacnaay 3660
ytnccnggna thytngtnyt nggnytngcn aargcncary tnathcarat httyttytty 3720
mgnytnaayy tnytnathac nytnytnggn ytnytncayg gnytngtntt yytnccngtn 3780
athytnwsnt aygtnggncc ngaygtnaay ccngcnytng cnytngarca raarmgngcn 3840
gargargcng tngcngcngt natggtngcn wsntgyccna aycayccnws nmgngtnwsn 3900
acngcngaya ayathtaygt naaycaywsn ttygarggnw snathaargg ngcnggngcn 3960
athwsnaayt tyytnccnaa yaayggnmgn cartty 3996